US010061107B2

(12) United States Patent
Loney et al.

(10) Patent No.: US 10,061,107 B2
(45) Date of Patent: Aug. 28, 2018

(54) METHOD AND DEVICE FOR SLIDE SCANNING

(71) Applicant: Ventana Medical Systems, Inc., Tucson, AZ (US)

(72) Inventors: Gregory C. Loney, Los Altos, CA (US); Glenn Stark, Scott Valley, CA (US); Chris Todd, San Jose, CA (US); Bikash Sabata, San Jose, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 14/619,268

(22) Filed: Feb. 11, 2015

(65) Prior Publication Data

US 2015/0153556 A1    Jun. 4, 2015

Related U.S. Application Data

(60) Division of application No. 13/444,141, filed on Apr. 11, 2012, now Pat. No. 9,036,255, which is a
(Continued)

(51) Int. Cl.
*G02B 21/26* (2006.01)
*G02B 21/00* (2006.01)
(Continued)

(52) U.S. Cl.
CPC ....... *G02B 21/0036* (2013.01); *G02B 21/002* (2013.01); *G02B 21/006* (2013.01);
(Continued)

(58) Field of Classification Search
CPC .. G02B 21/26; B01L 9/52; G01N 2035/00138
See application file for complete search history.

(56) References Cited

U.S. PATENT DOCUMENTS 2,788,485 A    4/1957 Parsons
3,232,165 A    2/1966 Dupuy et al.
(Continued)

FOREIGN PATENT DOCUMENTS

CA    2842721    4/2011
CN    2418493 Y    2/2001
(Continued)

OTHER PUBLICATIONS

Extended European Search Report dated Dec. 21, 2015.
(Continued)

*Primary Examiner* — Thanh Luu
(74) *Attorney, Agent, or Firm* — Muirhead and Saturnelli, LLC

(57) ABSTRACT

Systems and techniques for an optical scanning microscope and/or other appropriate imaging system includes components for scanning and collecting focused images of a tissue sample and/or other object disposed on a slide. The focusing system described herein provides for determining best focus for each snapshot as a snapshot is captured, which may be referred to as "on-the-fly focusing." The devices and techniques provided herein lead to significant reductions in the time required for forming a digital image of an area in a pathology slide and provide for the creation of high quality digital images of a specimen at high throughput.

16 Claims, 45 Drawing Sheets

Related U.S. Application Data continuation of application No. PCT/US2010/002772, filed on Oct. 18, 2010.

(60) Provisional application No. 61/367,341, filed on Jul. 23, 2010, provisional application No. 61/299,231, filed on Jan. 28, 2010, provisional application No. 61/261,251, filed on Nov. 13, 2009, provisional application No. 61/256,228, filed on Oct. 29, 2009, provisional application No. 61/252,995, filed on Oct. 19, 2009.

(51) Int. Cl.
| | | |
|---|---|---|
| *G02B 21/24* | (2006.01) | |
| *G02B 21/36* | (2006.01) | |
| *G01N 1/31* | (2006.01) | |
| *G01N 35/00* | (2006.01) | |
| *G01N 35/04* | (2006.01) | |

(52) U.S. Cl.
CPC .......... *G02B 21/245* (2013.01); *G02B 21/26* (2013.01); *G02B 21/361* (2013.01); *G01N 1/312* (2013.01); *G01N 35/0099* (2013.01); *G01N 2035/00049* (2013.01); *G01N 2035/00138* (2013.01); *G01N 2035/0441* (2013.01); *G01N 2035/0462* (2013.01); *G01N 2035/0493* (2013.01)

(56) References Cited

U.S. PATENT DOCUMENTS

| | | | |
|---|---|---|---|
| 3,233,949 | A | 2/1966 | Rieman et al. |
| 3,848,963 | A | 11/1974 | Peck |
| 4,113,223 | A | 9/1978 | Kakizaki |
| 4,433,235 | A | 2/1984 | Akiyama et al. |
| 4,453,807 | A | 6/1984 | Faulkner et al. |
| 5,075,079 | A | 12/1991 | Kerr et al. |
| 5,367,401 | A | 11/1994 | Saulietis |
| 5,428,690 | A | 6/1995 | Bacus et al. |
| 5,467,153 | A | 11/1995 | Fargeot |
| 5,532,874 | A * | 7/1996 | Stein ............. G02B 21/26 359/368 |
| 5,589,938 | A | 12/1996 | Deck |
| 5,650,840 | A | 7/1997 | Taniguchi |
| 5,768,033 | A | 6/1998 | Brock |
| 5,982,535 | A | 11/1999 | Inoue et al. |
| 6,118,582 | A * | 9/2000 | Del Buono ......... B01L 3/50855 359/391 |
| 7,006,674 | B1 | 2/2006 | Zahniser et al. |
| 7,012,575 | B2 | 3/2006 | Kim et al. |
| 7,012,757 | B2 | 3/2006 | Wallerstein |
| 7,066,004 | B1 | 6/2006 | Kohler et al. |
| 7,202,953 | B1 | 4/2007 | Mueller et al. |
| 7,390,997 | B2 | 6/2008 | Tohma |
| 7,589,892 | B2 | 9/2009 | Tohma et al. |
| 7,697,831 | B1 | 4/2010 | Tsai et al. |
| 2002/0104231 | A1 | 8/2002 | Tominaga et al. |
| 2003/0173509 | A1 | 9/2003 | Ito et al. |
| 2004/0170312 | A1 | 9/2004 | Soenksen |
| 2005/0068614 | A1 | 3/2005 | Yoneyama et al. |
| 2006/0050376 | A1 | 3/2006 | Houston et al. |
| 2007/0057106 | A1 | 3/2007 | Scampini |
| 2008/0020128 | A1 | 1/2008 | van Ryper et al. |
| 2009/0023610 | A1 * | 1/2009 | Peytavi ............. B01L 3/5027 506/39 |
| 2009/0027558 | A1 | 1/2009 | Mantiuk et al. |
| 2009/0141345 | A1 | 6/2009 | Tsuchiya |
| 2009/0195688 | A1 | 8/2009 | Henderson et al. |
| 2011/0190153 | A1 * | 8/2011 | Adey ............... C40B 60/12 506/9 |
| 2013/0271594 | A1 | 10/2013 | Olson et al. |

FOREIGN PATENT DOCUMENTS

| | | |
|---|---|---|
| CN | 101300518 A | 11/2008 |
| CN | 101382649 A | 3/2009 |
| DE | 41 31 360 A1 | 3/1993 |
| EP | 1 367 423 A1 | 12/2003 |
| EP | 2 196 836 A1 | 6/2010 |
| GB | 3092 A | 0/1906 |
| GB | 2 034 913 A | 6/1980 |
| JP | S52-035212 | 3/1977 |
| JP | S52-143848 | 11/1977 |
| JP | S 52-143848 A | 11/1977 |
| JP | S58-002817 | 1/1983 |
| JP | S61-239780 A | 10/1986 |
| JP | S62-35212 A | 2/1987 |
| JP | H4-357460 | 12/1992 |
| JP | H05-4122 | 1/1993 |
| JP | H05-38618 | 5/1993 |
| JP | H08201700 A | 8/1996 |
| JP | H10197802 A | 7/1998 |
| JP | H11-109245 | 4/1999 |
| JP | HEI 11-109245 | 4/1999 |
| JP | 2000 241713 A | 9/2000 |
| JP | 2005 202092 A | 7/2005 |
| JP | 2006-281553 A | 10/2006 |
| JP | H06-281553 | 10/2006 |
| JP | 2007-086559 | 4/2007 |
| JP | 2009-098437 | 5/2009 |
| WO | WO 2004095360 A1 | 11/2004 |
| WO | WO 2009/031477 A1 | 3/2009 |
| WO | WO 2011/049608 A2 | 4/2011 |

OTHER PUBLICATIONS

Chinese Office Action dated Oct. 19, 2015.
European Partial Search Report dated Jan. 7, 2016.
Japanese Office Action dated May 12, 2015.
Canadian Office Action dated May 7, 2015.
Japanese Notice of Allowance dated Feb. 9, 2016.
European Office Action dated Jan. 8, 2016.
Japanese Office Action dated Sep. 1, 2015.
Extended European Search Report dated Apr. 28, 2016.
European Office Action and Partial Extended European Search Report dated Jan. 7, 2016.
Chinese Office Action dated Dec. 29, 2015.
Indian Examination Report dated Aug. 17, 2017.

* cited by examiner

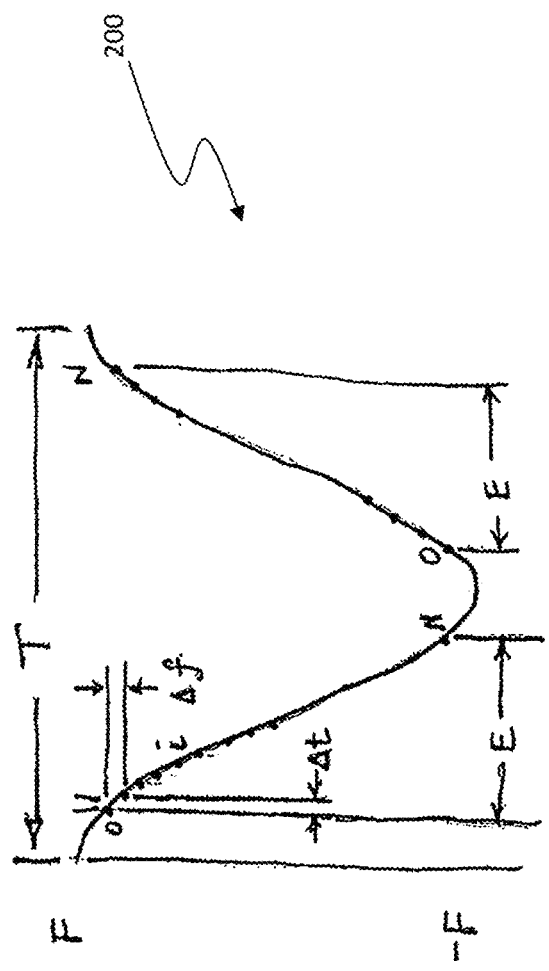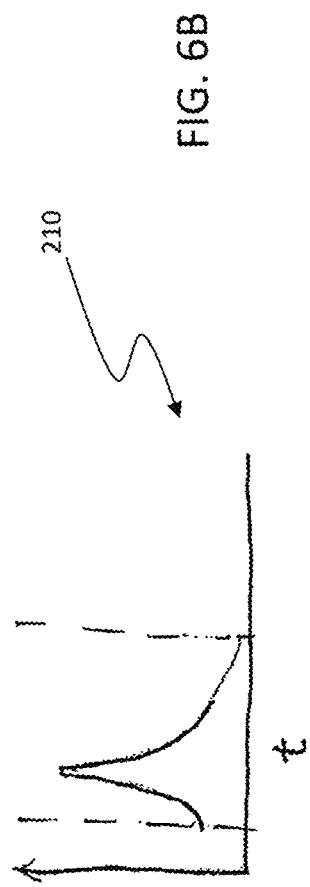
FIG. 6A
FIG. 6B

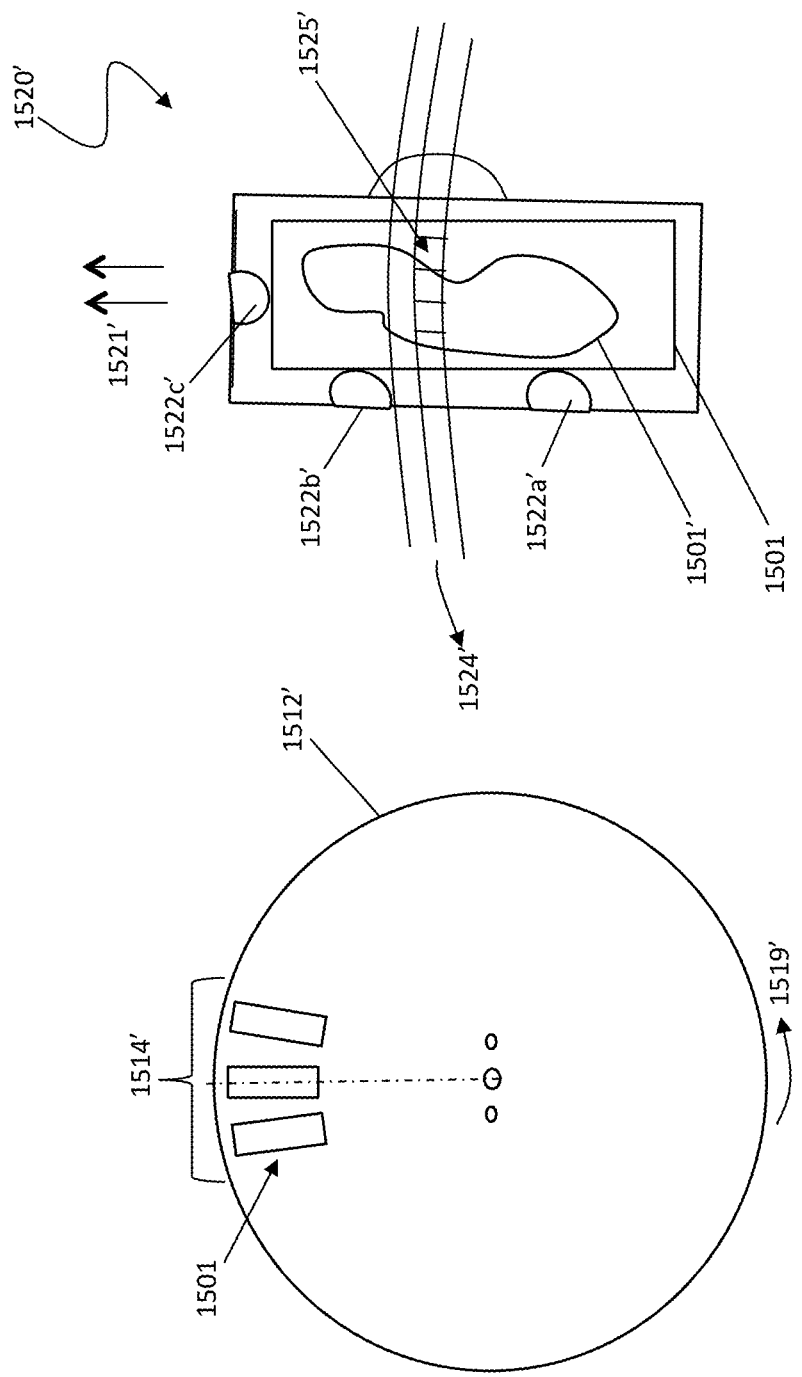

METHOD AND DEVICE FOR SLIDE SCANNING

RELATED APPLICATIONS

This application is a divisional of U.S. application Ser. No. 13/444,141 filed Apr. 11, 2012 (pending), which is a continuation of International Application No. PCT/US2010/002772, filed Oct. 18, 2010, which claims priority to U.S. Provisional App. No. 61/367,341, filed Jul. 23, 2010, entitled "On-the-Fly Focusing Sensor;" U.S. Provisional App. No. 61/299,231, filed Jan. 28, 2010, entitled "Slide Caching in a Slide Scanning Microscope;" U.S. Provisional Application No. 61/261,251, filed Nov. 13, 2009, entitled "Scanning Microscope Slide Stage;" U.S. Provisional App. No. 61/256,228, filed Oct. 29, 2009, entitled "High Speed Slide Scanning System for Digital Pathology;" and to U.S. Provisional App. No. 61/252,995, filed Oct. 19, 2009, entitled "On-the-Fly Focusing Systems and Techniques for Scanning Microscopes," all of which are incorporated herein by reference.

TECHNICAL FIELD

This application relates to the field of imaging and, more particularly, to systems and techniques for obtaining and capturing images.

BACKGROUND OF THE INVENTION

Molecular imaging identification of changes in the cellular structures indicative of disease remains a key to the better understanding in medicinal science. Microscopy applications are applicable to microbiology (e.g., gram staining, etc.), plant tissue culture, animal cell culture (e.g. phase contrast microscopy, etc.), molecular biology, immunology (e.g., ELISA, etc.), cell biology (e.g., immunofluorescence, chromosome analysis, etc.), confocal microscopy, time-lapse and live cell imaging, series and three-dimensional imaging.

There have been advances in confocal microscopy that have unraveled many of the secrets occurring within the cell and the transcriptional and translational level changes can be detected using fluorescence markers. The advantage of the confocal approach results from the capability to image individual optical sections at high resolution in sequence through the specimen. However, there remains a need for systems and methods for digital processing of images of pathological tissue that provide accurate analysis of pathological tissues, at a relatively low cost.

It is a desirable goal in digital pathology to obtain high resolution digital images for viewing in a short period of time. Current manual methods whereby the pathologist views a slide through the ocular lens of a microscope allows a diagnosis upon inspection of cell characteristics or count of stained cells vs. unstained cells. Automated methods are desirable whereby digital images are collected, viewed on high resolution monitors and may be shared and archived for later use. It is advantageous that the digitization process be accomplished efficiently at a high throughput and with high resolution and high quality images.

In conventional virtual microscopy systems, imaging techniques can produce individual images that may be significantly out of focus over much of the image. Conventional imaging systems are restricted to a single focal distance for each individual snapshot taken by a camera, thus, each of these "fields of view" has areas that are out of focus when the subject specimen being scanned does not have a uniform surface. At the high magnification levels employed in virtual microscopy, specimens with a uniform surface are extremely rare.

Conventional systems use a pre-focusing technique to address the high proportion of out-of-focus images that is based on a two step process that includes: 1) determining, in a first pass, the best focus at an array of points, separated by n image frames, arranged on a two-dimensional grid laid on the top of a tissue section; and 2) in another pass, moving to each focus point and acquire an image frame. For points between these best focus points, the focus is interpolated. While this two step process may reduce or even eliminate out-of-focus images, the process results in a significant loss in the speed of acquiring the tiled images.

Accordingly, it would be desirable to provide a system that overcomes the significant problems inherent in conventional imaging systems and efficiently provides focused, high quality images at a high throughput.

SUMMARY OF THE INVENTION

According to the system described herein, a device for obtaining a focused image of a specimen includes an objective lens disposed for examination of the specimen. A slow focusing stage is coupled to the objective lens, and the slow focusing stage controls movement of the objective lens. A dither focus stage including a dither lens, and the dither focus stage moves the dither lens. A focus sensor provides focus information in accordance with light transmitted via the dither lens. At least one electrical component uses the focus information to determine a metric and a first focus position of the objective lens in accordance with the metric, wherein the electrical component sends position information to the slow focusing stage for moving the objective lens into the first focus position. An image sensor captures an image of the specimen after the objective lens is moved into the first focus position. An XY moving stage may be included, the specimen being disposed on the XY moving stage, and in which the electrical component controls movement of the XY moving stage. The movement of the XY moving stage may be phase locked with the motion of the dither lens. The dither focus stage may include a voice-coil actuated flexured assembly that moves the dither lens in a translational motion. The dither lens may be moved at a resonant frequency that is at least 60 Hz, and wherein the electrical component uses the focus information to perform at least 60 focus calculations per second. The focus sensor and the dither focus stage may be set to operate bidirectionally, in which the focus sensor produces the focus information on both an up and down portion of a sinusoid waveform of the motion of the dither lens at the resonant frequency. The metric may include contrast information, sharpness information, and/or chroma information. The focus information may include information for a plurality of zones of a focus window that is used during a focus scan of the specimen. The electrical component may control movement of the XY moving stage, and wherein the information from at least a portion of the plurality of zones is used in determining a speed of the XY moving stage. A field of view of the focus sensor may be tilted in relation to a field of view of the image sensor.

According further to the system described herein, a method for obtaining a focused image of a specimen is provided. The method includes controlling movement of an objective lens disposed for examination of the specimen. Motion of a dither lens is controlled and focus information is provided in accordance with light transmitted via the dither lens. The focus information is used to determine a metric and determine a first focus position of the objective lens in accordance with the metric. Position information is sent that is used to move the objective lens into the first focus position. The first focus position may be determined as a best focus position, and the method may further include capturing an image of the specimen after the objective lens is moved into the best focus position. The dither lens may be moved at a resonant frequency that is at least 60 Hz, and at least 60 focus calculations may be performed per second. The metric may include sharpness information, contrast information and/or chroma information. The focus information may include information for a plurality of zones of a focus window that is used during a focus scan of the specimen. Movement of an XY moving stage on which the specimen is disposed may be controlled, and the information from at least a portion of the plurality of zones may be used in determining a speed of the XY moving stage. The movement of the XY moving stage may be controlled to provide forward and backward translational scanning of the specimen.

According further to the system described herein, a method for obtaining an image of a specimen includes establishing a nominal focus plane. The specimen is positioned at a starting position having associated x and y coordinates. First processing is performed in a single traversal over said specimen. The first processing includes determining, for each of a plurality of points, a focus position using a dither lens, and acquiring, for each of said plurality of points, a frame in accordance with said focus position.

According further to the system described herein, a computer readable medium comprising code stored thereon for obtaining a focused image of a specimen according to any of the above-noted steps. Further, a computer readable medium may comprise code stored thereon for performing any one of more of the processes described below.

According further to the system described herein, a device for a microscope stage includes a moving stage block and a base block that guides the moving stage block. The base block includes a first block being substantially flat and a second block having a triangular shape, wherein the first block and the second block guide the moving stage block in a translational direction. The first block and the second block may be supported on raised bosses on a base plate. The first block and the second block may be made of glass. A plurality of button elements may be disposed on the moving stage block that contact the first block and the second block, and the button elements may permit motion of the moving stage block in only the translational direction. The button elements may be spherically shaped and made of thermoplastic. At least two of the plurality of button elements may be arranged to face each other on each side of the triangular shape of the second block, and wherein at least one button of the plurality of button elements contacts the first block on a flat face thereof. Positions of the plurality of button elements on the moving stage block may form a triangle. Each of the plurality of button elements may bear equal weight during stage motion. The moving stage block may be shaped to have a center of gravity at a centroid of the triangle formed by the positions of the plurality of button elements. A cantilever arm assembly may be provided and a flexural element may be provided having a first end rigidly coupled to the cantilever assembly and a second end coupled to a center of mass location on the moving stage block. The cantilever arm assembly may include a cantilever arm coupled to a bearing block which runs via a recirculating bearing design on a rail. Driving of the bearing block on the rail may cause the flexural element to apply a force to the moving stage block. Bending stiffness of the flexural element may isolate the moving stage block from up and down motions of the cantilever arm assembly. The base block may form another moving stage in a direction perpendicular to the translational direction of the moving stage block. Repeatability in motion may be provided on the order of 150 nanometers. The repeatability in motion may be orthogonal to the moving stage and base block translational directions.

According further to the system described herein, a device for slide caching includes a rack, a buffer, a slide handler that moves a first slide between the rack and the buffer, and an XY stage. The XY stage moves a second slide in connection with a scan of the second slide, and at least one function of the slide handler corresponding to the first slide is performed in parallel with at least one function of the XY stage corresponding to the second slide. The slide handler may move the first slide and the second slide between the rack, the buffer and the XY stage and may move with at least three degrees of freedom. The XY stage may include a slide pickup head that moves slides from the buffer to the XY stage. An imaging device may image the first slide and the second slide, and may include a focusing system and a camera. The focusing system may include a dynamic focusing system. The function of the slide handler performed in parallel with the function of the XY stage may provide a time gain of at least 10%. The slide handler may include a slide pickup head that include a mechanical pickup device and/or a vacuum pickup device. The buffer may include a plurality of buffer positions that accept a plurality of slides. At least one buffer position of the buffer may be a position used to capture a thumbnail image of a slide. The rack may include at least one main tray and a by-pass tray, and a slide disposed in the by-pass tray is processed before any slide disposed in the main tray.

According further to the system described herein, a method for slide caching includes providing a rack and a buffer. A first slide is moved between the rack and the buffer. A second slide is moved into or out of the buffer in connection with a scan of the second slide. Moving the first slide between the rack and the buffer may be performed in parallel with the scan of the second slide. The scan of the second slide may include a focusing operation and an image capture operation. The moving of first slide in parallel with the scan of the second slide may provide a time gain of at least 10%. The scan of the second slide may include a dynamic focusing operation. The buffer may include a plurality of buffer positions that include at least one of: a camera buffer position and a return buffer position. The method may further include capturing a thumbnail image of the first slide and/or the second slide when the first slide and/or the second slide is in the camera buffer position.

According further to the system described herein, a device for slide caching includes a first rack, a second rack, a first XY stage and a second XY stage. The first XY stage moves a first slide into or out of the first rack in connection with a scan of the first slide. The second XY stage moves a second slide into or out of the second rack in connection with a scan of the second slide. At least one function of the first XY stage corresponding to the first slide is performed in parallel with at least one function of the second XY stage corresponding to the second slide. The first rack and the second rack may form parts of a single rack. An imaging device may image the first slide and the second slide. Each of the first XY stage and the second XY stage may include a slide pickup head.

According further to the system described herein, a device for slide scanning includes a rotatable tray and at least one recess disposed in the rotatable tray. The recess is sized to receive a slide, and the recess stabilizes the slide in a scanning position as a result of rotation of the rotatable tray. The recess may include a plurality of protrusions that stabilize the slide and may include a plurality of recesses disposed on a circumferential ring of the rotatable tray. An imaging system may be included, and at least one component of the imaging system moves in a radial direction of the rotatable tray. The component of the imaging system may move incrementally in the radial direction corresponding to one complete rotation of the rotatable tray. The recess may be sized to receive a slide having a length that is greater than a width of the slide, and the length of the slide may be oriented in a radial direction of the rotatable tray. The recess may be sized to receive a slide having a length that is greater than a width of the slide, and the width of the slide may be oriented in a radial direction of the rotatable tray.

According further to the system described herein, a method for scanning a slide includes disposing the slide in at least one recess of a rotatable tray and rotating the rotatable tray. The recess is sized to receive a slide, and the recess stabilizes the slide in a scanning position as a result of rotation of the rotatable tray. The recess may include a plurality of protrusions that stabilize the slide and may include a plurality of recesses disposed on a circumferential ring of the rotatable tray. The method may further include providing an imaging system and moving at least one component of the imaging system in a radial direction of the rotatable tray. The component of the imaging system may be moved incrementally in the radial direction corresponding to one complete rotation of the rotatable tray. The recess may be sized to receive a slide having a length that is greater than a width of the slide, and wherein the length of the slide is oriented in a radial direction of the rotatable tray. The recess may be sized to receive a slide having a length that is greater than a width of the slide, and wherein the width of the slide is oriented in a radial direction of the rotatable tray.

BRIEF DESCRIPTION OF THE DRAWINGS

Embodiments of the system described herein will be explained in more detail herein based on the figures of the drawings, which are briefly described as follows.

FIG. 6A is a schematic illustration of a plot showing the command waveform of the dither focus optics and sharpness determinations according to an embodiment of the system described herein.

FIG. 6B is a schematic illustration showing a plot of calculated sharpness ($Z_s$) values for a portion of the sine wave motion of the dither lens.

FIGS. 35A and 35B are schematic illustrations showing an alternative arrangement of slides on a rotating slide holder according to another embodiment of the system described herein.

DETAILED DESCRIPTION OF VARIOUS EMBODIMENTS

Figure 1:
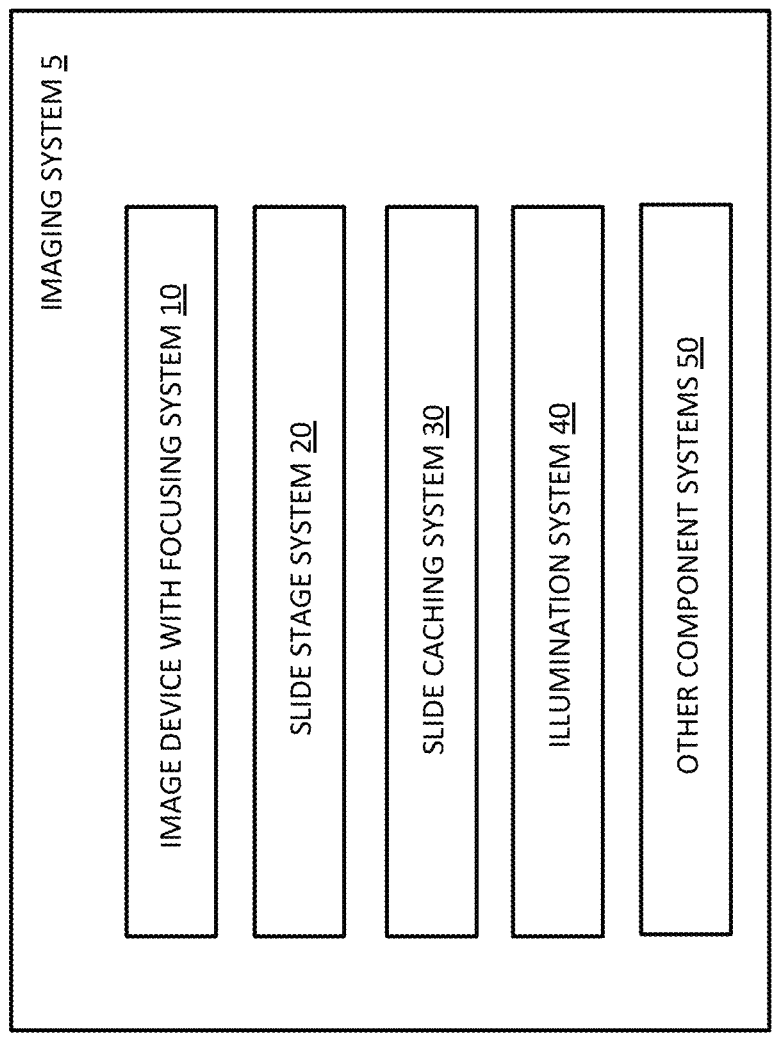
FIG. 1 is a schematic illustration of an imaging system of a scanning microscope and/or other scanning device that may include various component devices used in connection with digital pathology sample scanning and imaging according to various embodiments of the system described herein.

FIG. 1 is a schematic illustration of an imaging system 5 of a scanning microscope and/or other scanning device that may include various component devices used in connection with digital pathology sample scanning and imaging according to various embodiments of the system described herein. The imaging system 5 may include an imaging device with focusing system 10, a slide stage system 20, a slide caching system 30 and an illumination system 40, among other component systems 50, as further discussed in detail elsewhere herein. It is also noted that the system described herein may be used in connection with microscope slide scanning instrument architectures and techniques for image capture, stitching and magnification as described in U.S. Patent App. Pub. No. 2008/0240613 A1 to Dietz et al., entitled "Digital Microscope Slide Scanning System and Methods," which is incorporated herein by reference, including features in connection with reconstituting an image with a magnification without substantial loss of accuracy and displaying or storing the reconstituted image.

Figure 2:
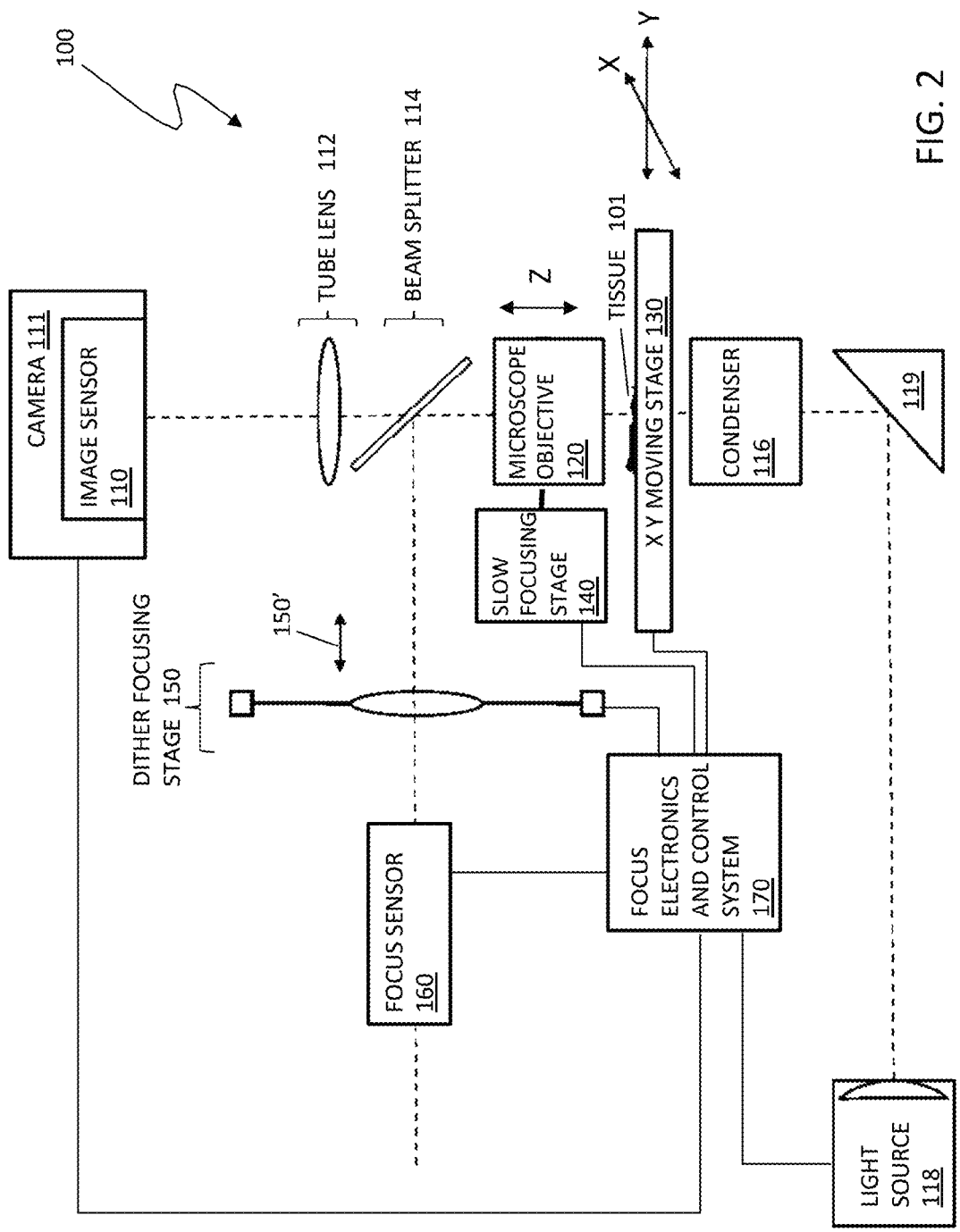
FIG. 2 is a schematic illustration showing an imaging device including a focus system according to an embodiment of the system described herein.

FIG. 2 is a schematic illustration showing an imaging device 100 of an optical scanning microscope and/or other appropriate imaging system that includes components of a focusing system for taking focused images of a tissue sample 101 and/or other object disposed on a slide according to an embodiment of the system described herein. The focusing system described herein provides for determining best focus for each snapshot as a snapshot is captured, which may be referred to as "on-the-fly focusing." The devices and techniques provided herein lead to significant reductions in the time required for forming a digital image of an area in a pathology slide. The system described herein integrates steps of the two-step approach of conventional systems and essentially eliminates the time required for pre-focusing. The system described herein provides creating a digital image of a specimen on a microscope slide using on-the-fly processing for capturing snapshots in which the total time for capturing all the snapshots is less than the time required by a method using a step of predetermining focus points for each snapshot prior to capturing the snapshots.

The imaging device 100 may include an imaging sensor 110, such as a charge-coupled device (CCD) and/or complimentary metal-oxide semiconductor (CMOS) image sensor, that may be part of a camera 111 that captures digital pathology images. The imaging sensor 110 may receive transmitted light from a microscope objective 120 transmitted via a tube lens 112, a beam splitter 114 and including other components of a transmitted light microscope such as a condenser 116 and a light source 118 and/or other appropriate optical components 119. The microscope objective 120 may be infinity-corrected. In one embodiment, the beam splitter 114 may provide for apportioning approximately 70% of the light beam source directed to the image sensor 110 and the remaining portion of approximately 30% directed along a path to the dither focusing stage 150 and focus sensor 160. The tissue sample 101 being imaged may be disposed on an XY moving stage 130 that may be moved in X and Y directions and which may be controlled as further discussed elsewhere herein. A slow focusing stage 140 may control movement of the microscope objective 120 in the Z direction to focus an image of the tissue 101 that is captured by the image sensor 110. The slow focusing stage 140 may include a motor and/or other suitable device for moving the microscope objective 120. A dither focusing stage 150 and a focus sensor 160 are used to provide fine focusing control for the on-fly-focusing according to the system described herein. In various embodiments, the focus sensor 160 may be a CCD and/or CMOS sensor.

The dither focusing stage 150 and the focus sensor 160 provide on-the-fly focusing according to sharpness values and/or other metrics that are rapidly calculated during the imaging process to obtain a best focus for each image snapshot as it is captured. As further discussed in detail elsewhere herein, the dither focusing stage 150 may be moved at a frequency, e.g., in a sinusoidal motion, that is independent of and exceeds the movement frequency practicable for the slower motion of the microscope objective 120. Multiple measurements are taken by the focus sensor 160 of focus information for views of the tissue over the range of motion of the dither focusing stage 150. The focus electronics and control system 170 may include electronics for controlling the focus sensor and dithering focus stage 150, a master clock, electronics for controlling the slow focus stage 140 (Z direction), X-Y moving stage 130, and other components of an embodiment of a system in accordance with techniques herein. The focus electronics and control system 170 may be used to perform sharpness calculations using the information from the dither focusing stage 150 and focus sensor 160. The sharpness values may be calculated over at least a portion of a sinusoidal curve defined by dither movement. The focus electronics and control system 170 may then use the information to determine the position for the best focus image of the tissue and command the slow focus stage 140 to move the microscope objective 120 to a desired position (along the Z-axis, as shown) for obtaining the best focus image during the imaging process. The control system 170 may also use the information to control the speed of the XY moving stage 120, for example, the speed of movement of the stage 130 in the Y direction. In an embodiment, sharpness values may be computed by differencing contrast values of neighboring pixels, squaring them and summing those values together to form one score. Various algorithms for determining sharpness values are further discussed elsewhere herein.

In various embodiments according to the system described herein, and in accordance with components discussed elsewhere herein, a device for creating a digital image of a specimen on a microscope slide includes: a microscope objective that is infinity corrected; a beam splitter; a camera focusing lens; a high-resolution camera; a sensor focus lens group; a dither focusing stage; a focusing sensor; a focusing coarse (slow) stage; and focus electronics. The device may allow for focusing the objective and capturing each snapshot through the camera without the need for predetermining a focus point for all snapshots prior to capturing the snapshots, and wherein the total time for capturing all the snapshots is less than the time required by a system requiring a step of predetermining focus points for each snapshot prior to capturing the snapshots. The system may include computer controls for: i) determining a first focus point on the tissue to establish a nominal focus plane by moving the coarse focus stage through the entire z range and monitoring sharpness values; ii) positioning the tissue in x and y to start at a corner of an area of interest; iii) setting the dither fine focus stage to move, wherein the dither focus stage is synchronized to a master clock which also controls the velocity of the xy stage; iv) commanding the stage to move from frame to adjacent frame, and/or v) producing a trigger signal to acquire a frame on the image sensor and trigger a light source to create a pulse of light.

Further, according to another embodiment, the system described herein may provide computer-implemented method for creating a digital image of a specimen on a microscope slide. The method may include determining a scan area comprising a region of the microscope slide that includes at least a portion of the specimen. The scan area may be divided into a plurality snapshots. The snapshots may be captured using a microscope objective and a camera, in which focusing the objective and microscope and capturing each snapshot through the camera may be conducted for each snapshot without the need for predetermining a focus point for all snapshots prior to capturing the snapshots. The total time for capturing all the snapshots may be less than the time required by a method requiring a step of predetermining focus points for each snapshot prior to capturing the snapshots.

Figure 3B:
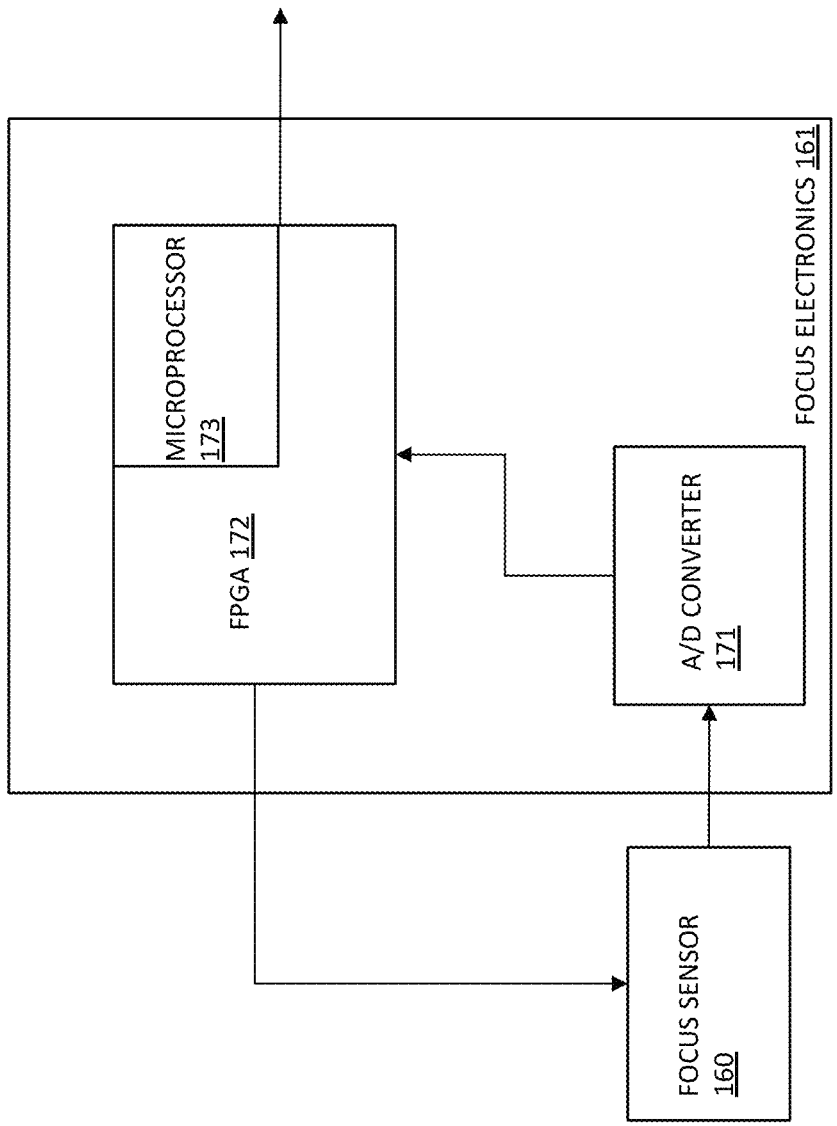
FIGS. 3A and 3B are schematic illustrations of an embodiment of the control system showing that the control system may include appropriate electronics.
Figure 3A:
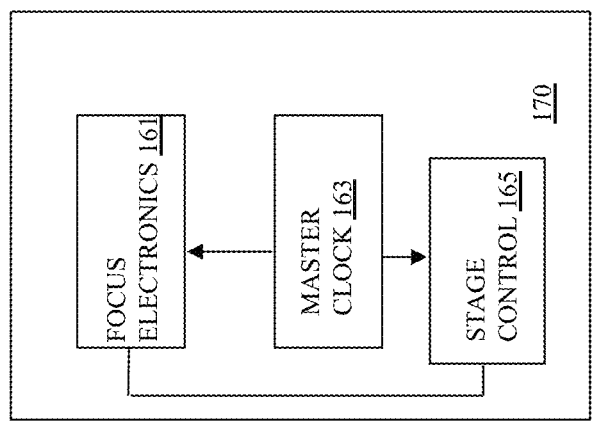

FIG. 3A is a schematic illustration of an embodiment of the focus electronics and control system 170 including focus electronics 161, a master clock 163 and stage control electronics 165. FIG. 3B is a schematic illustration of an embodiment of the focus electronics 161. In the illustrated embodiment, the focus electronics 161 may include appropriate electronics such as a suitably fast A/D converter 171 and a field-programmable gate array (FPGA) 172 with a microprocessor 173 that may be used to make sharpness calculations. The A/D converter 171 may receive information from the focus sensor 160 which is coupled to the FPGA 172 and microprocessor 173 and used to output sharpness information. The master clock included in 170 may supply the master clock signal to the focus electronics 161, stage control electronics 165, and other components of the system. The stage control electronics 165 may generate control signals used to control the slow focus stage 140, X-Y moving stage 130, dither focusing stage 150, and/or other control signals and information, as further discussed elsewhere herein. The FPGA 172 may supply a clock signal to the focus sensor 160, among other information. Measurements in the lab show a sharpness calculation on a 640×32 pixel frame can be made in 18 microseconds, easily fast enough for suitable operation of the system described herein. In an embodiment, the focus sensor 160 may include a monochrome CCD camera windowed to 640×32 strip, as further discussed elsewhere herein.

The scanning microscope may acquire either a 1D or 2D array of pixels including contrast information, and/or intensity information in RGB or some other color space as further discussed elsewhere herein. The system finds best focus points over a large field, for example on a glass slide 25 mm×50 mm. Many commercial systems sample the scene produced by a 20×, 0.75 NA microscope objective with a CCD array. Given the NA of the objective and condenser of 0.75 and wavelength of 500 nm the lateral resolution of the optical system is about 0.5 micron. To sample this resolution element at the Nyquist frequency, the pixel size at the object is about 0.25 micron. For a 4 Mpixel camera (e.g., a Dalsa Falcon 4M30/60), running at 30 fps, with a pixel size of 7.4 micron the magnification from the object to the imaging camera is 7.4/0.25=30×. Therefore, one frame at 2352×1728 may cover an area of 0.588 mm×0.432 mm at the object, which equates to about 910 frames for a typical tissue section defined as 15 mm×15 mm in area. The system described herein is desirably used where tissue spatial variation in the focus dimension is much lower than the frame size at the object. Variations in focus, in practice, occur over greater distances and most of the focus adjustment is made to correct for tilts. These tilts are generally in the range of 0.5-1 micron per frame dimension at the object.

Time to result for current scanning systems (e.g., a BioImagene iScan Coreo system) is about 3.5 minutes for pre-scan and scan of a 20×15 mm×15 mm field and about 15 minutes for a 40× scan on 15 mm×15 mm field. The 15 mm×15 mm field is scanned by running 35 frames in 26 passes. The scans may be done uni-directionally with a 1 sec retrace time. The time to scan using a technique according to the system described herein may be about 5 seconds to find the nominal focus plane, 1.17 seconds per pass (25 passes), for a total of 5+25×(1.17+1)=59.25 seconds (about 1 minute). This is a considerable time savings over conventional approaches. Other embodiments of the systems described herein may allow even faster focus times, but a limitation may occur on the amount of light needed for short illumination times to avoid motion blur on continuous scan. Pulsing or strobing the light source 118, which may be an LED light source as further discussed elsewhere herein, to allow high peak illumination can mitigate this issue. In an embodiment, the pulsing of the light source 118 may be controlled by the focus electronics and control system 170. In addition, running the system bi-directionally would eliminate the retrace time saving about 25 seconds for a 20× scan resulting in a scan time of 35 seconds.

It should be noted that the components used in connection with the focus electronics and control system 170 may also more generally be referred to as electrical components used to perform a variety of different functions in connection with embodiments of the techniques described herein.

Figure 4:
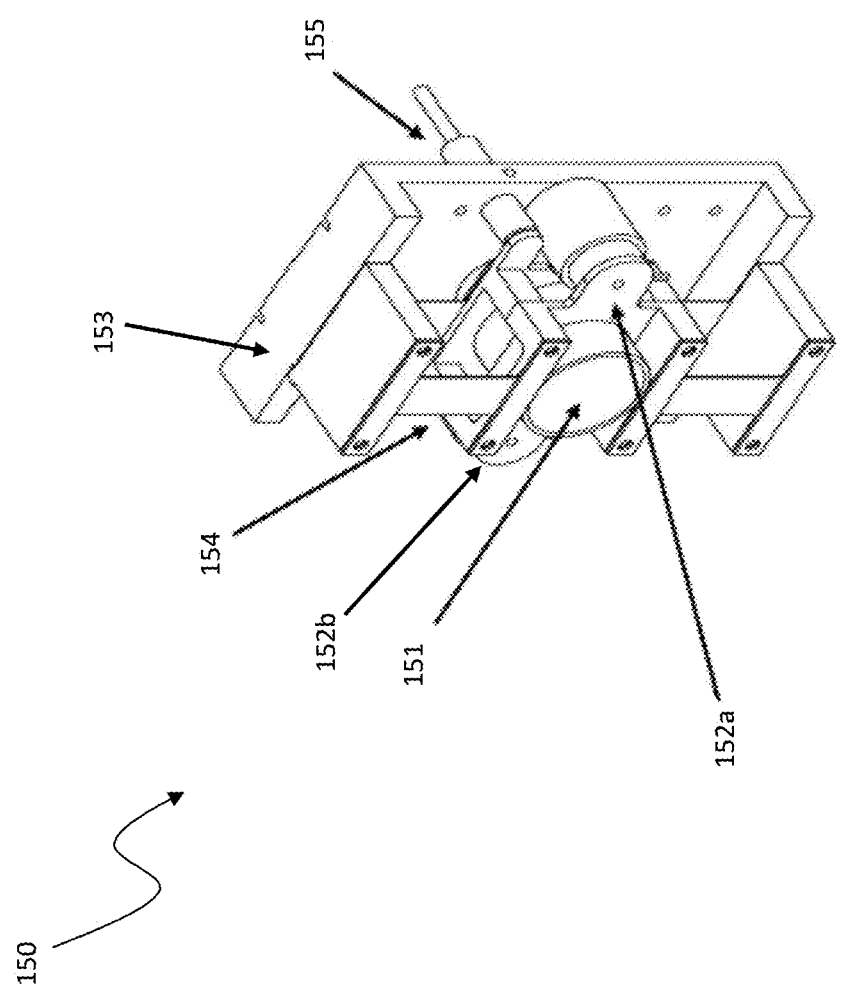
FIG. 4 is a schematic illustration showing the dither focus stage in more detail according to an embodiment of the system described herein.

FIG. 4 is a schematic illustration showing the dither focus stage 150 in more detail according to an embodiment of the system described herein. The dither focus stage 150 may include a dither focusing lens 151 that may be moved by one or more actuators 152a,b, such as voice coil actuators, and which may be mounted into a rigid housing 153. In an embodiment, the lens may be achromatic lens having a 50 mm focal length, as is commercially available, see for example Edmund Scientific, NT32-323. Alternatively, the dither focusing lens 151 may be constructed from plastic, aspheric and shaped such that the weight of the lens is reduced (extremely low-mass). A flexure structure 154 may be attached to the rigid housing 153 and attached to a rigid ground point and may allow only translational motion of the dither focusing lens 151, for example, small distances of about 600-1000 microns. In an embodiment, the flexure structure 154 may be constructed of an appropriate stainless steel sheets, of about 0.010" thick in the bending direction and form a four-bar linkage. The flexure 154 may be designed from a suitable spring steel at a working stress far from its fatigue limit (factor of 5 below) to operate over many cycles.

The moving mass of the dither focusing lens 151 and flexure 154 may be designed to provide about a 60 Hz or more first mechanical resonance. The moving mass may be monitored with a suitable high bandwidth (e.g., >1 kHz) position sensor 155, such as a capacitive sensor or eddy current sensor, to provide feedback to the control system 170 (see FIG. 2). For example, KLA Tencor's ADE division manufactures a capacitive sensor 5 mm 2805 probe with a 1 kHz bandwidth, 1 mm measurement range, and 77 nanometer resolution suitable for this application. The dither focus and control system, such as represented by functionality included in element 170, may keep the amplitude of the dither focusing lens 151 to a prescribed focus range. The dither focus and control system may rely on well known gain-controlled oscillator circuits. When operated in resonance the dither focusing lens 151 may be driven at low current, dissipating low power in the voice coil windings. For example, using a BEI Kimco LAO8-10 (Winding A) actuator the average currents may be less than 180 mA and power dissipated may be less than 0.1 W.

It is noted that other types of motion of the dither lens and other types of actuators 152a,b may be used in connection with various embodiments of the system described herein. For example, piezoelectric actuators may be used as the actuators 152a,b. Further, the motion of the dither lens may be motion at other than resonant frequencies that remains independent of the motion of the microscope objective 120.

The sensor 155, such as the capacitive sensor noted above as may be included in an embodiment in accordance with techniques herein, may provide feedback as to where the dither focusing lens is positioned (e.g. with respect to the sine wave or cycle corresponding to the movements of the lens). As will be described elsewhere herein, a determination may be made as to which image frame obtained using the focus sensor produces the best sharpness value. For this frame, the position of the dither focusing lens may be determined with respect to the sine wave position as indicated by the sensor 155. The position as indicated by the sensor 155 may be used by the control electronics of 170 to determine an appropriate adjustment for the slow focusing stage 140. For example, in one embodiment, the movement of the microscope objective 120 may be controlled by a slow stepper motor of the slow focus stage 140. The position indicated by the sensor 155 may be used to determine a corresponding amount of movement (and corresponding control signal(s)) to position the microscope objective 120 at a best focus position in the Z direction. The control signal(s) may be transmitted to the stepper motor of the slow focus stage 140 to cause any necessary repositioning of the microscope objective 120 at the best focus position.

FIGS. 5A-5E are schematic illustrations showing an iteration of the focusing operations according to the system described herein. The figures show the image sensor 110, the focus sensor 160, the dither focusing stage 150 with a dither lens and the microscope objective 120. The tissue 101 is illustrated moving in the y-axis, i.e. on the XY moving stage 130, while the focus operations are performed. In an example, the dither focusing stage 150 may move the dither lens at a desired frequency, such as 60 Hz or more (e.g., 80 Hz, 100 Hz), although it is noted that, in other embodiments, the system described herein may also operate with the dither lens moving at a lower frequency (e.g., 50 Hz) according to applicable circumstances. The XY moving stage 130 may be commanded to move, e.g., in the Y direction, from frame to adjacent frame. For example, the stage 130 may be commanded to move at a constant of 13 mm/sec which for a 20× objective corresponds to an acquisition rate of about 30 frames/sec. Since the dither focus stage 150 and XY moving stage 130 may be phase locked, the dither focus stage 150 and sensor 160 may make 60 focus calculations per second, or functioning bi-directionally (reading on the up and down motion of the sine wave) 120 focus points per second or 4 focus points per frame. For a frame height of 1728 pixels, this equates to a focus point every 432 pixels or for the 20× objective every 108 microns. Since the XY moving stage 130 is moving, the focus point should be captured in a very short period of time, for example 330 μsec (or less), to keep the variation in the scene minimal.

In various embodiments, as further discussed elsewhere herein, this data may be stored and used to extrapolate the next frame's focus position or, alternatively, extrapolation may not be used and the last focus point is used for the focus position of the active frame. With a dither frequency of 60 Hz and a frame rate of 30 frames per second the focus point is taken at a position no more than ¼ of a frame from the center of the snapped frame. Generally, tissue heights do not change enough in ¼ of a frame to make this focus point inaccurate.

A first focus point may be found on the tissue to establish the nominal focus plane or reference plane 101'. For example, the reference plane 101' may be determined by initially moving the microscope objective 120, using the slow focus stage 140, through the entire Z range say +1/−1 mm and monitoring sharpness values. Once the reference plane 101' is found, the tissue 101 may be positioned in X and Y to start at a corner, and/or other particular location, of the area of interest, and the dither focusing stage 150 is set to move, and/or otherwise movement of the dither focusing stage 150 continues to be monitored, beginning in FIG. 5A.

Figure 5A:
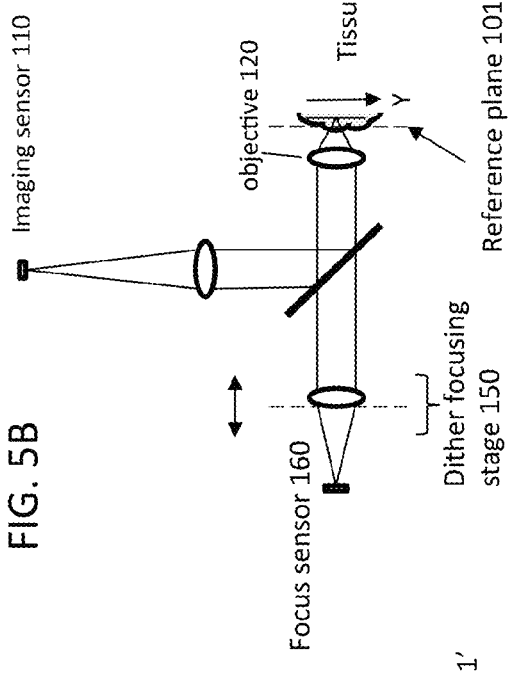
FIGS. 5A-5E are schematic illustrations showing an iteration of the focusing operations according to the system described herein.
Figure 5C:
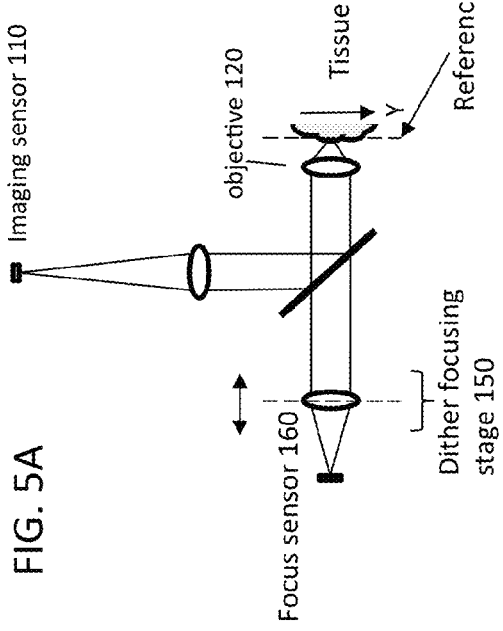
Figure 5B:
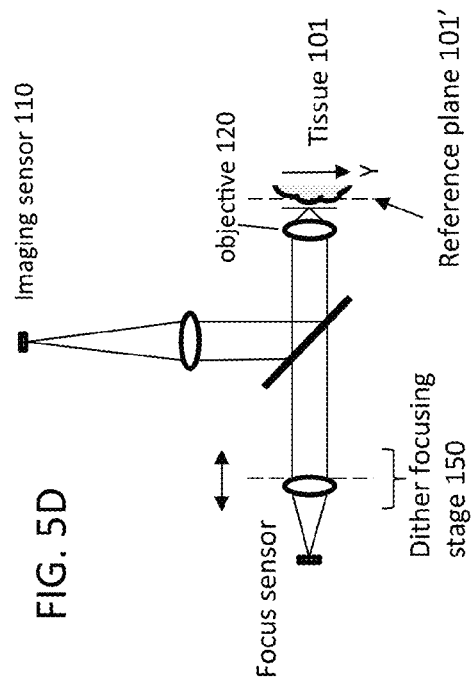
Figure 5D:
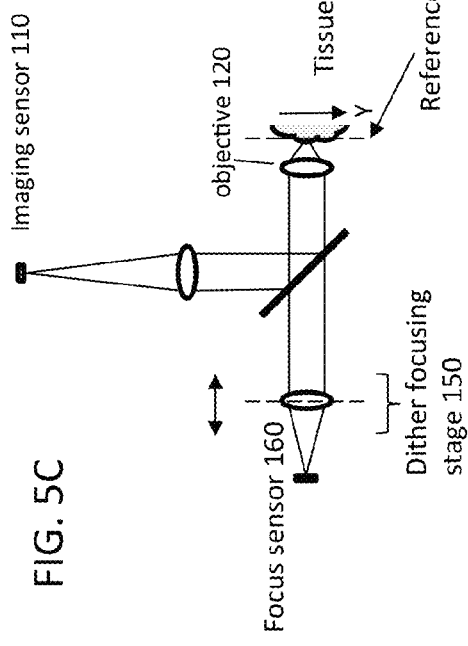
Figure 5E:
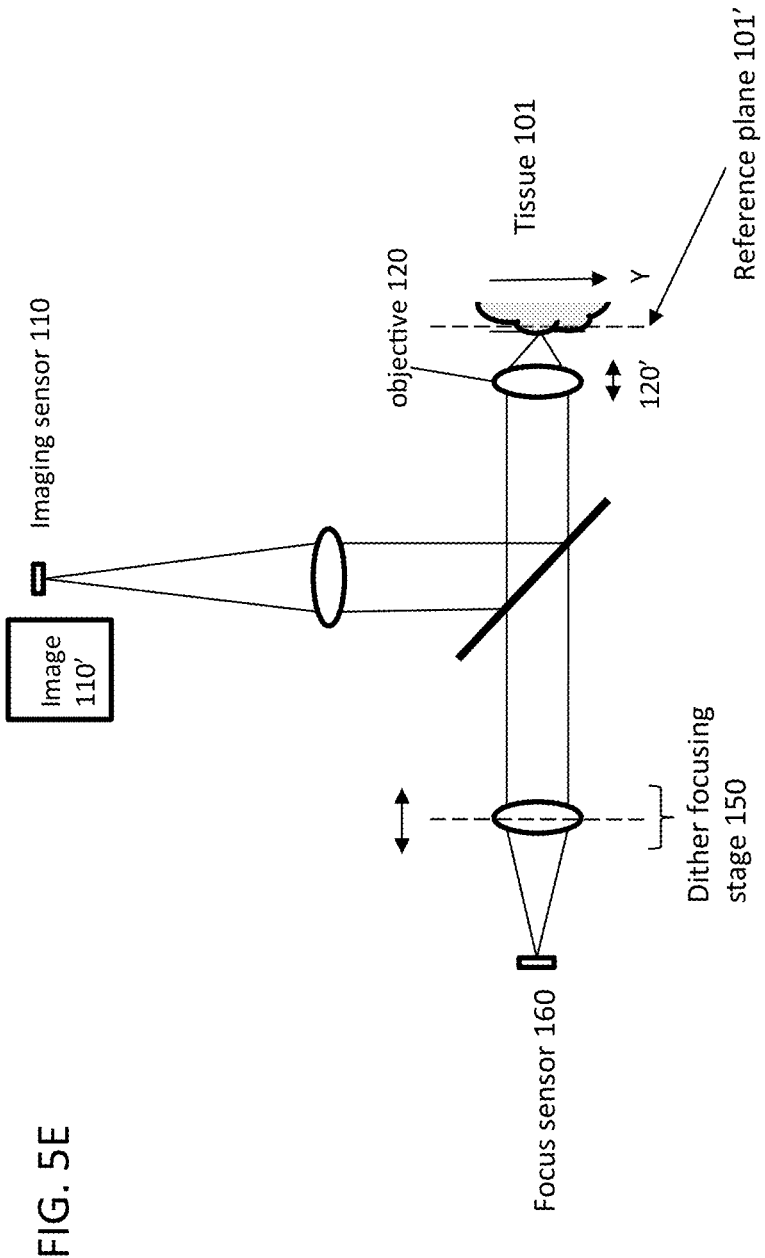

The dither focus stage 150 may be synchronized to a master clock in the control system 170 (see FIG. 2) which may also be used in connection with controlling the velocity of the XY moving stage 130. For example, if the dither focus stage 150 were to move through a 0.6 millimeter p-v (peak to valley) sinusoidal motion at 60 Hertz, assuming an 32% duty cycle to use the sinusoid's more linear range, 8 points could be collected through the focus range over an 2.7 msec period. In FIGS. 5B-5D the dither focusing stage 150 moves the dither lens in a sinusoidal motion and focus samples are taken along through at least a portion of the sinusoidal curve. Focus samples would be taken therefore every 330 µsec or at a rate of 3 kHz. With a magnification of 5.5× between the object and the focus sensor 160, a motion at the dither lens of 0.6 mm p-v equates to a 20 micron p-v motion at the objective lens. This information is used to convey the position at which highest sharpness is computed, i.e. the best focus, to the slower stepper motor of the slow focus stage 140. As shown in FIG. 5E, the slow focus stage 140 is commanded to move the microscope objective 120 to the best focus position (illustrated by motion range 120') in time for the image sensor 110 to capture the best focus image 110' of the area of interest of the tissue 101. In an embodiment, the image sensor 110 may be triggered, e.g. by the control system 170, to snapshot an image after a specific number of cycles of the dither lens motion. The XY moving stage 130 moves to the next frame, the cyclical motion of the dither lens in the dither focus stage 150 continues, and focusing operations of FIGS. 5A-5E are repeated. Sharpness values may be calculated at a rate that does not bottleneck the process, e.g., 3 kHz.

FIG. 6A is a schematic illustration of a plot 200 showing the command waveform of the dither focus optics and sharpness determinations according to an embodiment of the system described herein. In an embodiment based on the times discussed in connection with the example of FIGS. 5A-5E:

T=16.67 msec, /* period of the dither lens sinusoid if the lens resonates at 60 Hz */
F=300 µm, /* positive range of focus values */
N=8, /* number of focus points obtained in the period E */
Δt=330 µsec, /* focus point samples obtained every 330 µsec */
E=2.67 msec, /* the period over which the N focus points are obtained */
Δf=1.06 µm at center of focus travel. /* step size of focus curve */

Therefore with this duty cycle of 32%, 8.48 µm (8×1.06 µm=8.48 µm) is sampled through focus processing.

FIG. 6B is a schematic illustration showing a plot 210 of calculated sharpness ($Z_s$) values for a portion of the sine wave motion of the dither lens shown in the plot 210. The position (z) for each focus plane sampled as a function of each point i is given by EQUATION 1:

$$z = F\cos\left[2\pi\left[\frac{(T-2E)}{4} + \Delta t \cdot i\right]\frac{1}{T}\right] \quad \text{EQUATION 1}$$

Windowing down a CCD camera may provide a high frame rate suitable for the system described herein. For example, the company Dalsa of Waterloo, Ontario, Canada produces the Genie M640-1/3 640×480 Monochrome camera. The Genie M640-1/3 will operate at 3,000 frame/sec at a frame size of 640×32. The pixel size on the CCD array is 7.4 microns. At the 5.5× magnification between the object and focus plane, one focus pixel is equivalent to about 1.3 micron at the object. Though some averaging of about 16 object pixels (4×4) per focus pixel may occur, sufficient high spatial frequency contrast change is preserved to obtain good focus information. In an embodiment, the best focus position may be determined according to the peak value of the sharpness calculations plot 210. In additional embodiments, it is noted that other focus calculations and techniques may be used to determine the best focus position according to other metrics, including the use of a contrast metric, as further discussed elsewhere herein.

Figures 7A, 7B:
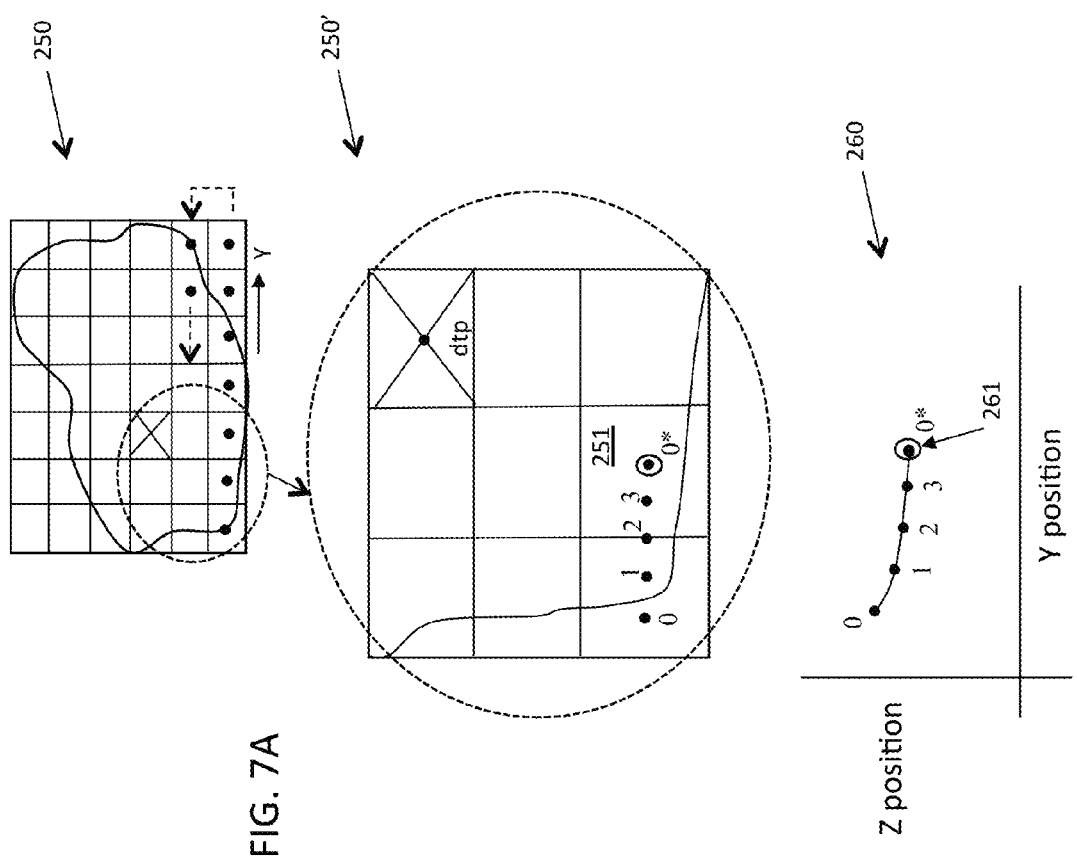
FIGS. 7A and 7B are schematic illustrations showing focusing determinations and adjustments of a specimen (tissue) according to an embodiment of the system described herein.

FIGS. 7A and 7B are schematic illustrations showing focusing determinations and adjustments of a specimen (tissue) according to an embodiment of the system described herein. In FIG. 7A, illustration 250 is a view of the specimen shown in approximate image frames in connection with movement of the specimen along the Y-axis according to movement of the XY moving stage 130 discussed herein. One traversal or pass over the specimen in connection with movement of the specimen along the Y-axis (e.g., according to movement of the XY stage) is illustrated in 250. Illustration 250' is an enlarged version of one portion of the illustration 250. One frame of the illustration 250' is designated dtp, referring to a definite tissue point of the specimen. In the example of illustration 250', a specimen boundary is shown and, during the scan thereover, multiple focus calculations are performed in accordance with the system described herein. In the frame 251, and by way example, there is illustrated that a best focus determination is made after 4 focus calculations (shown as focus positions 1, 2, 3 and 0*) are performed in connection with imaging the specimen, although more focus calculations may be performed in connection with the system described herein. FIG. 7B shows a schematic illustration 260 showing a plot of the Z-axis position of the microscope objective in relation to Y-axis position of the specimen being examined. The illustrated position 261 shows the determined position along the Z-axis for adjusting the microscope objective 120 to achieve best focus according to an embodiment of the system described herein.

It should be noted that the system described herein provides significant advantages over conventional systems, such as those described in U.S. Pat. Nos. 7,576,307 and 7,518,642, which are incorporated herein by reference, in which the entire microscope objective is moved through focus in a sinusoid or triangular pattern. The system provided herein is advantageous in that it is suitable for use with microscope objective and an accompanying stage that are heavy (especially if other objectives are added via a turret) and cannot be moved at the higher frequencies described using the dither optics. The dither lens described herein may have an adjusted mass (e.g., be made lighter, less glass) and the imaging demands on the focus sensor are less than that imposed by the microscope objective. The focus data may be taken at high rates, as described herein, to minimize scene variation when computing sharpness. By minimizing scene variation, the system described herein reduces discontinuities in the sharpness metric as the system moves in and out of focus while the tissue is moving under the microscope objective. In conventional systems, such discontinuities add noise to the best focus calculation.

Figure 8:
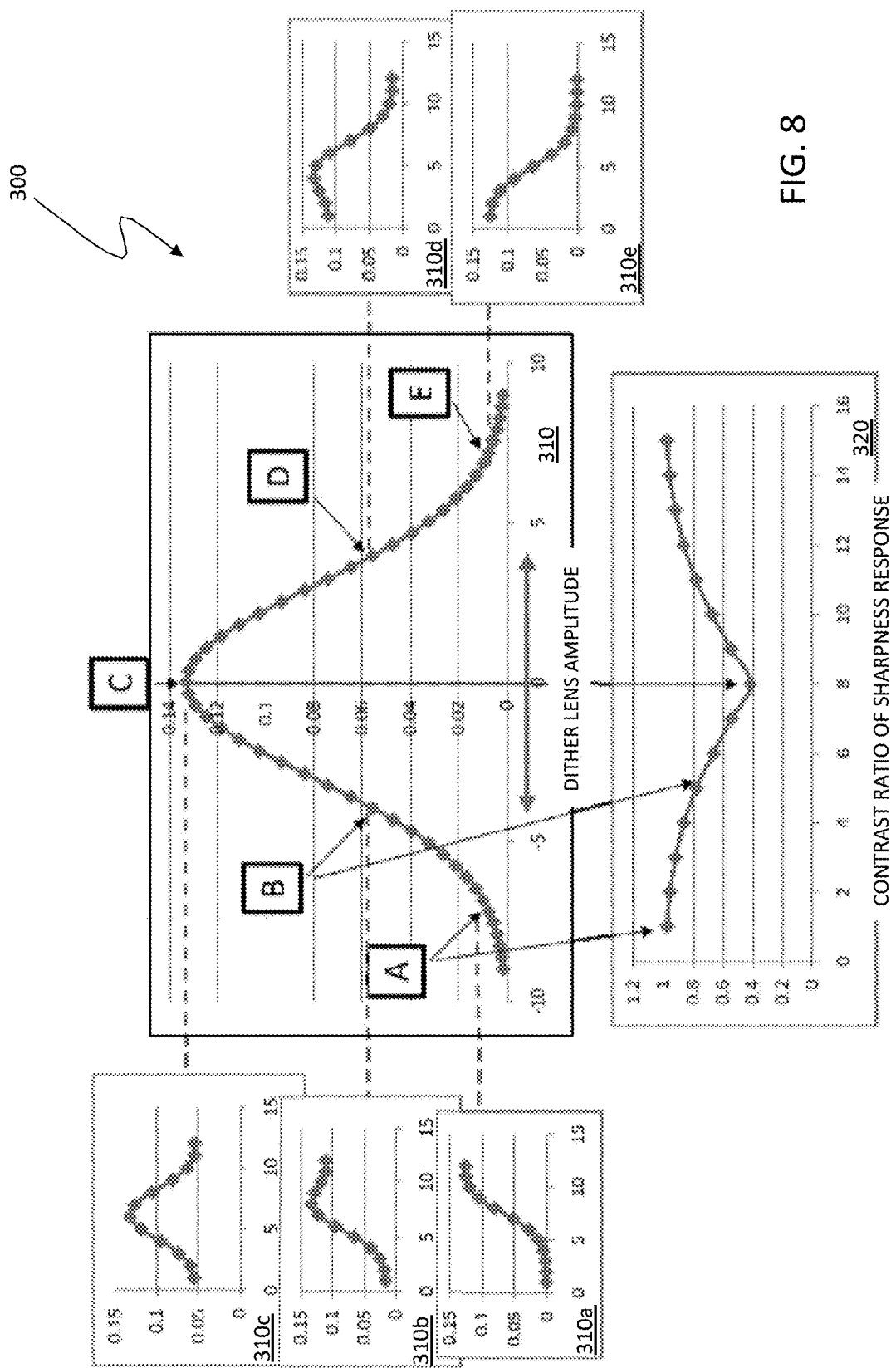
FIG. 8 is a schematic illustration showing an example of a sharpness profile including a sharpness curve and contrast ratio for each sharpness response at multiple points that are sampled by the dither focusing optics according to an embodiment of the system described herein.

FIG. 8 is a schematic illustration 300 showing an example of a sharpness profile, produced from moving through focus positions, including a sharpness curve and contrast ratio for each sharpness response at multiple points that are sampled by the dither focusing optics according to an embodiment of the system described herein. Plot 310 shows dither lens amplitude in micrometers in the x-axis and sharpness units along the y-axis. As illustrated, the dither lens motion may be centered at representative points A, B, C, D and E; however, is it noted that the computations described herein may be applied to each of the points on the sharpness curve. The sharpness response produced from the focus sensor 160, for a half cycle of the dither lens sinusoid, when motion of the dither lens is centered at each of the points A, B, C, D and E is shown, respectively, in the plots 310a-e. Based thereon, a contrast ratio for each of the sharpness responses having a corresponding one of the points A-E is computed according to: Contrast function=(max−min)/(max+min). In connection with the contrast function determined for one of the points A-E (e.g., at which dither lens motion is centered) and the corresponding one of the sharpness response curves 310a-e, max represents the largest sharpness value obtained from the sharpness response curve and min represents the smallest sharpness value obtained from the sharpness response curve. The resulting contrast function plot 320 is shown below the sharpness curve plot 310 and plots contrast ratio values corresponding to movement of the dither lens according to the dither lens amplitude. The minimum of the contrast function in the plot 320 is the best focus position. Based on the contrast function and best focus position determination, a control signal may be generated that is used to control the slow focus stage 140 to move the microscope objective 120 into the best focus position before the image sensor 110 captures the image 110'.

Figure 9:
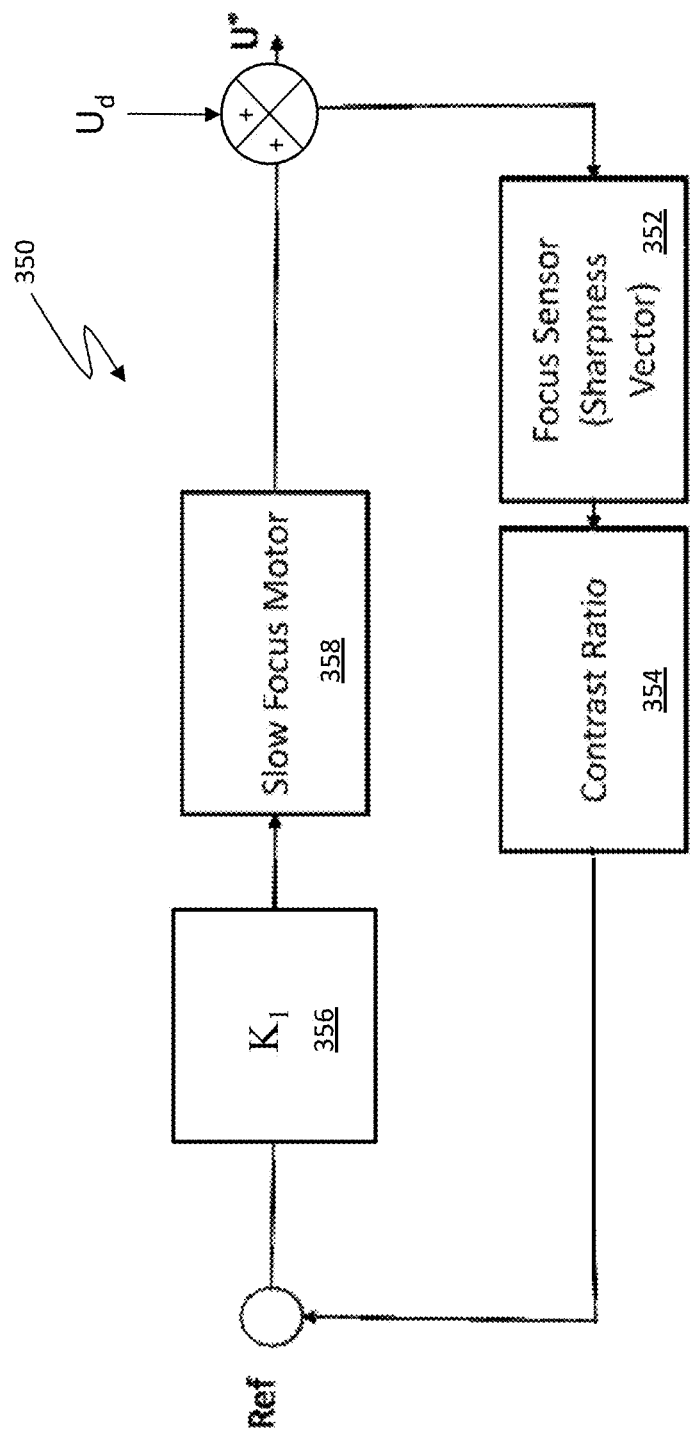
FIG. 9 shows a functional control loop block diagram illustrating use of the contrast function to produce a control signal to control the slow focus stage.

FIG. 9 shows a functional control loop block diagram 350 illustrating use of the contrast function to produce a control signal to control the slow focus stage 140. $U_d$ may be considered as a disturbance to the focus control loop and may represent the slide tilt or changing tissue surface heights, for example. Functional block 352 shows generation of sharpness vector information that may be generated by the focus sensor 160 and communicated to the focus electronics and control system 170. Functional block 354 shows generation of a contrast number (e.g., value of the contrast function) at the point the dither lens is sampling focus. This contrast number is compared to a set point or reference value (Ref) produced at an initial step where best focus was previously established The error signal produced from this comparison with appropriate applied gain $K_1$ (at functional block 356) corrects the slow focus motor which acts (at functional block 358) to keep the scene in focus. It should be noted that an embodiment may adjust the position of the microscope objective 120 in accordance with a minimum or threshold amount of movement. Thus, such an embodiment may avoid making adjustments smaller than the threshold.

Figure 10:
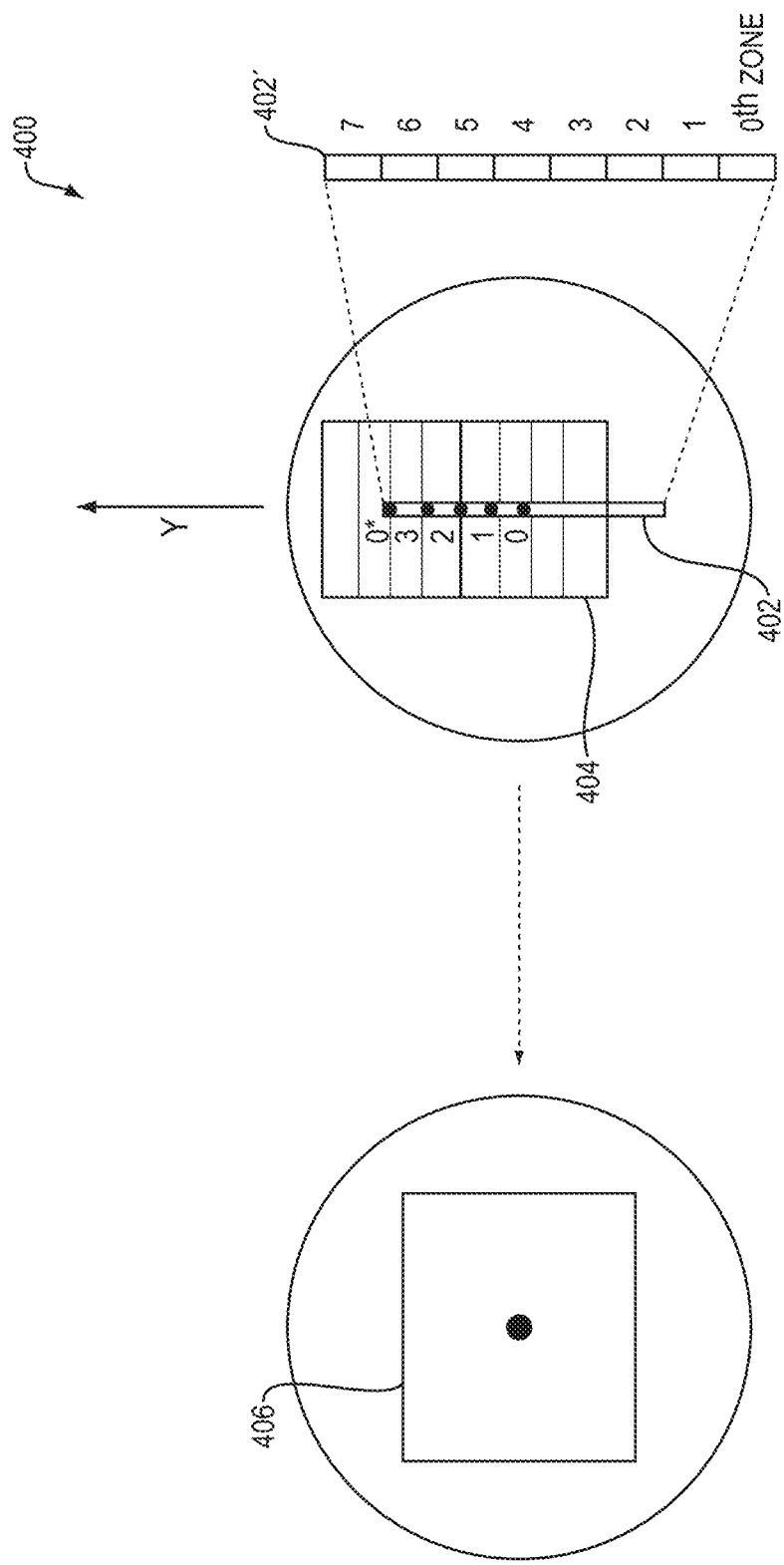
FIG. 10 is a schematic illustration showing the focus window being broken up into zones in connection with focus processing according to an embodiment of the system described herein.

FIG. 10 is a schematic illustration showing the focus window 402 being broken up into zones in connection with focus processing according to an embodiment of the system described herein. In the illustrated embodiment, the focus window is subdivided into 8 zones (402'); however, fewer or more than 8 zones may be used in connection with the system described herein. A first subset of the zones may be within a snapshot n and a second subset of zones is within snapshot n+1. For example, Zones 2, 3, 4, 5 are within the image frame 404 snapped at time t1. Zones 6 and 7 may be completely within the next image frame to be snapped as the XY moving stage 130 traverses from bottom to top in the figure and/or Zones 0 and 1 may be completely within the next image frame to be snapped as the stage 130 traverses from top to bottom of the figure. Focus positions 0, 1, 2, and 3 may be used to extrapolate the best focus position for the next snapped frame at position 0*. Coverage of the tissue may be established, for example, by executing a serpentine pattern traversing the complete area of interest.

The rectangular window 404 of the image sensor may be oriented in the direction of travel of the stage 130, such as a column of frames acquired during imaging is aligned with the rectangular focus window 402. The size of the object in the image frame 406, using, e.g., a Dalsa 4M30/60 CCD camera, is 0.588 mm×0.432 mm using a 30× magnification tube lens. The array size may be (2352×7.4 micron/30)× (1720×.7.4 micron/30). The image frame's 406 wider dimension (0.588 mm) may be oriented perpendicular to the focus window 402 and allows the minimum number of columns traversed over a section of tissue. The focus sensor is 0.05 mm×0.94 mm using a 5× magnification in the focus leg 406. The rectangular window 402 may be (32×.7.4 micron/5.0)×(640×7.4 micron/5.0). Therefore, the frame 402 of the focus sensor may be about 2.2× taller than the frame 404 of the image sensor, and may be advantageously used in connection with a look-ahead focusing technique involving multiple zones, as further discussed elsewhere herein. According to an embodiment of the system described herein, 120 best focus determinations may be made per second, with a sharpness calculation made every 333 μsec, resulting in 8 sharpnesses calculated over 2.67 msec equal to an approximately 32% duty cycle for an 8.3 msec half dither period of the dither lens motion.

A sharpness metric for each zone may be computed and stored. When computing a sharpness metric for a single focus point using multiple zones, the sharpness metric may be determined for each zone and combined, for example, such as by adding all sharpness metrics for all zones considered at such a single point. An example of the sharpness computation per zone is shown in EQUATION 2 (e.g., based on use of a camera windowed to a 640×32 strip). For row i, dimension n up to 32, and column j, dimension m up to 640/z, where z is the number of zones, sharpness for a zone may be represented by EQUATION 2:

$$\text{Sharpness} = \Sigma_{i=0}^{n-1} \Sigma_{j=0}^{m-k-1} [(I_{i,j} - I_{i,j+k})^2] \quad \text{EQUATION 2}$$

where k is an integer between or equal to 1 and 5. Other sharpness metrics and algorithms may also be used in connection with the system described herein. As the XY moving stage 130 is moving along the y-axis, the system acquires sharpness information for all of the Zones 0-7 in the focus window 402. It is desirable as the stage 130 is moving to know how the tissue section heights are varying. By computing a sharpness curve (maximum sharpness being best focus), by varying focus height, Zones 6 and 7, for example, may provide information prior to moving the next frame on where the next best focus plane is positioned. If large focus changes are anticipated by this look-ahead, the stage 130 may be slowed to provide more closely spaced points to better track the height transition.

During the scanning process, it may be advantageous to determine whether the system is transitioning from a white space (no tissue) to a darker space (tissue). By computing sharpness, in Zones 6 and 7, for example, it is possible to predict if this transition is about to occur. While scanning the column, if Zones 6 and 7 show increased sharpness, the XY moving stage 130 may be commanded to slow down to create more closely spaced focus points on the tissue boundary. If on the other hand a movement from high sharpness to low sharpness is detected, then it may be determined that the scanner view is entering a white space, and it may be desirable to slow down the stage 130 to create more closely spaced focus points on the tissue boundary. In areas where these transitions do not occur, the stage 130 may be commanded to move at higher constant speeds to increase the total throughput of slide scanning. This method may allow for advantageously fast scanning tissue. According to the system described herein, snapshots may be taken while focusing data is collected. Furthermore, all focus data may be collected in a first scan and stored and snapshots may be taken at best focus points during a subsequent scan. An embodiment may use contrast ratio or function values in a manner similar to that as described herein with sharpness values to detect changes in focus and accordingly determine transitions into, or out, of areas containing tissue or white space.

For example, for a 15 mm×15 mm 20× scan, at the image frame size of 0.588×0.432 mm, there are 26 columns of data, each column has 35 frames. At an imaging rate of 30 fps each column is traversed in 1.2 seconds or a scan time of about 30 seconds. Since the focus sensor 160 computes 120 (or more) focus points per second, the system described herein may obtain 4 focuses per frame (120 focus/sec divided by 30 fps). At an imaging rate of 60 fps, scan time is 15 seconds and 2 focuses per frame (120 focuses/sec divided by 60 fps).

In another embodiment, a color camera may be used as the focus sensor 160 and a chroma metric may be determined alternatively and/or additionally to the sharpness contrast metric. For example, a Dalsa color version of the 640×480 Genie camera may be suitably used as the focus sensor 140 according to this embodiment. The chroma metric may be described as colorfulness relative to the brightness of a similarly illuminated white. In equation form (EQUATIONS 3A and 3B), chroma (C) may be a linear combination of R, G, B color measures:

$$C_B = -37.797 \times R - 74.203 \times G + 112 \times B \qquad \text{EQUATION 3A}$$

$$C_R = 112 \times R - 93.786 \times G - 18.214 \times B \qquad \text{EQUATION 3B}$$

Note for R=G=B, $C_B = C_R = 0$. A value for C, representing total chroma, may be determined based on $C_B$ and $C_R$. (e.g., such as by adding $C_B$ and $C_R$).

As the XY moving stage 130 is moving along the y axis, the focus sensor 160 may acquire color (R, G, B) information, as in a bright field microscope. It is desirable as the stage is moving to know how the tissue section heights are varying. The use of RGB color information may be used, as with the contrast technique, to determine whether the system is transitioning from a white space (no tissue) to a colorful space (tissue). By computing chroma in Zones 6 and 7, for example, it is possible to predict if this transition is about to occur. If, for example, very little chroma is detected, then C=0 and it may be recognized that no tissue boundaries are approaching. However, while scanning the focus column, if Zones 6 and 7 show increased chroma, then the stage 130 may be commanded to slow down to create more closely spaced focus points on the tissue boundary. If on the other hand a movement from high chroma to low chroma is detected, then it may be determined that the scanner is entering a white space, and it may be desirable to slow down the stage 130 to create more closely spaced focus points on the tissue boundary. In areas where these transitions do not occur, the stage 130 may be commanded to move at higher constant speeds to increase the total throughput of slide scanning.

In connection with use of sharpness values, contrast ratio values, and/or chroma values to determine when the field of view or upcoming frame(s) is entering or exiting a slide area with tissue, processing variations may be made. For example, when entering an area with tissue from white space (e.g., between tissue areas), movement in the Y direction may be decreased and a number of focus points obtained may also increase. When viewing white space or an area between tissue samples, movement in the Y direction may be increased and fewer focus points determined until movement over an area containing tissue is detected (e.g., such as by increased chroma and/or sharpness values).

Figure 11:
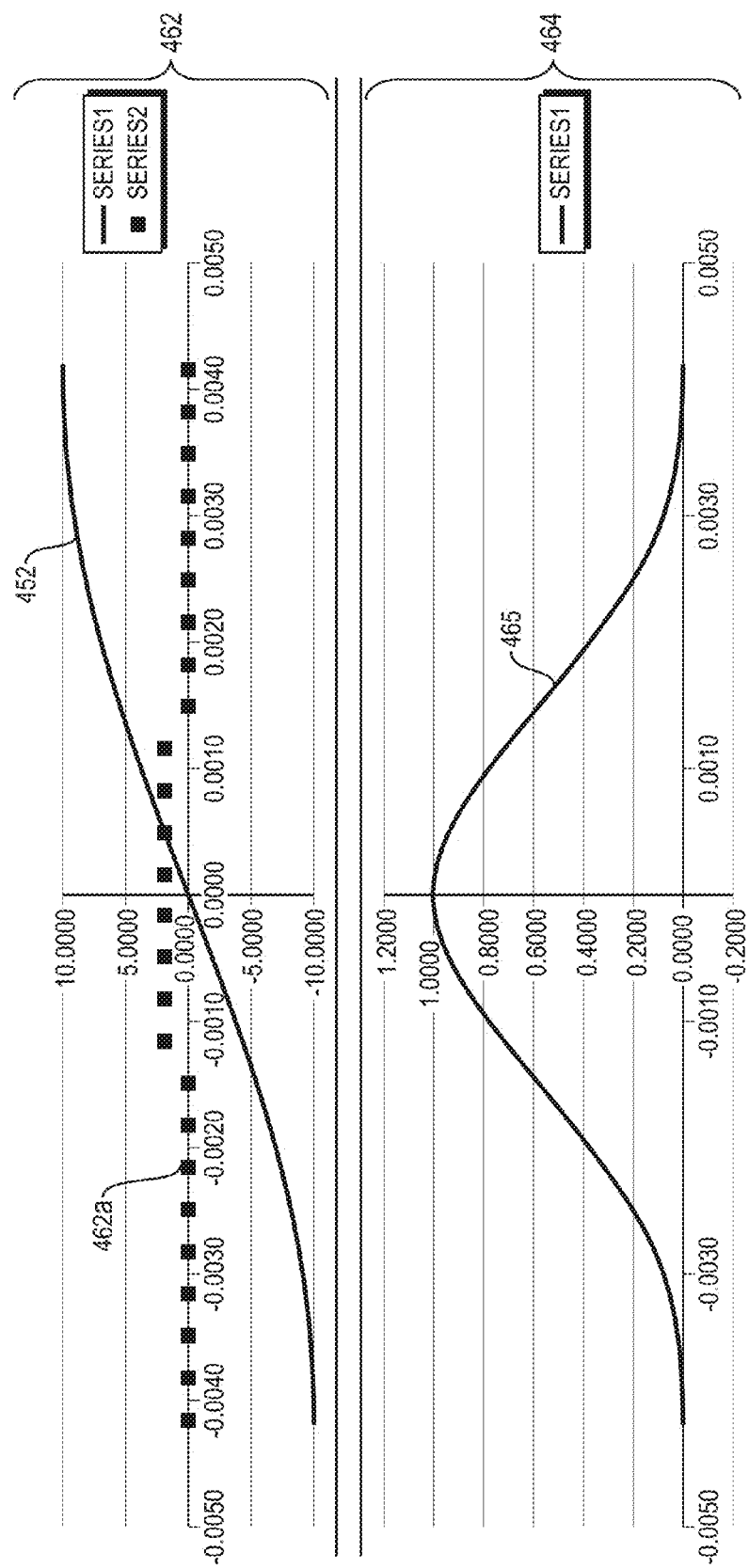
FIG. 11 shows a graphical illustration of different sharpness values that may be obtained at points in time in an embodiment in accordance with techniques herein.

FIG. 11 shows a graphical illustration of different sharpness values that may be obtained at points in time in an embodiment in accordance with techniques herein. The top portion 462 includes a curve 452 corresponding to a half sine wave cycle (e.g., half of a single peak to peak cycle or period) of the dither lens movement. The X axis corresponds to dither lens amplitude values during this cycle and the Y axis corresponds to sharpness values. Each of the points, such as point 462a, represents a point at which a frame is obtained using the focus sensor where each frame is obtained at a dither lens amplitude represented by the X axis value of the point and has a sharpness values represented by the Y axis value of the point. Element 465 in the bottom portion 464 represents a curve fitted for the set of sharpness values obtained as represented in portion 462 for the illustrated data points.

Figure 12:
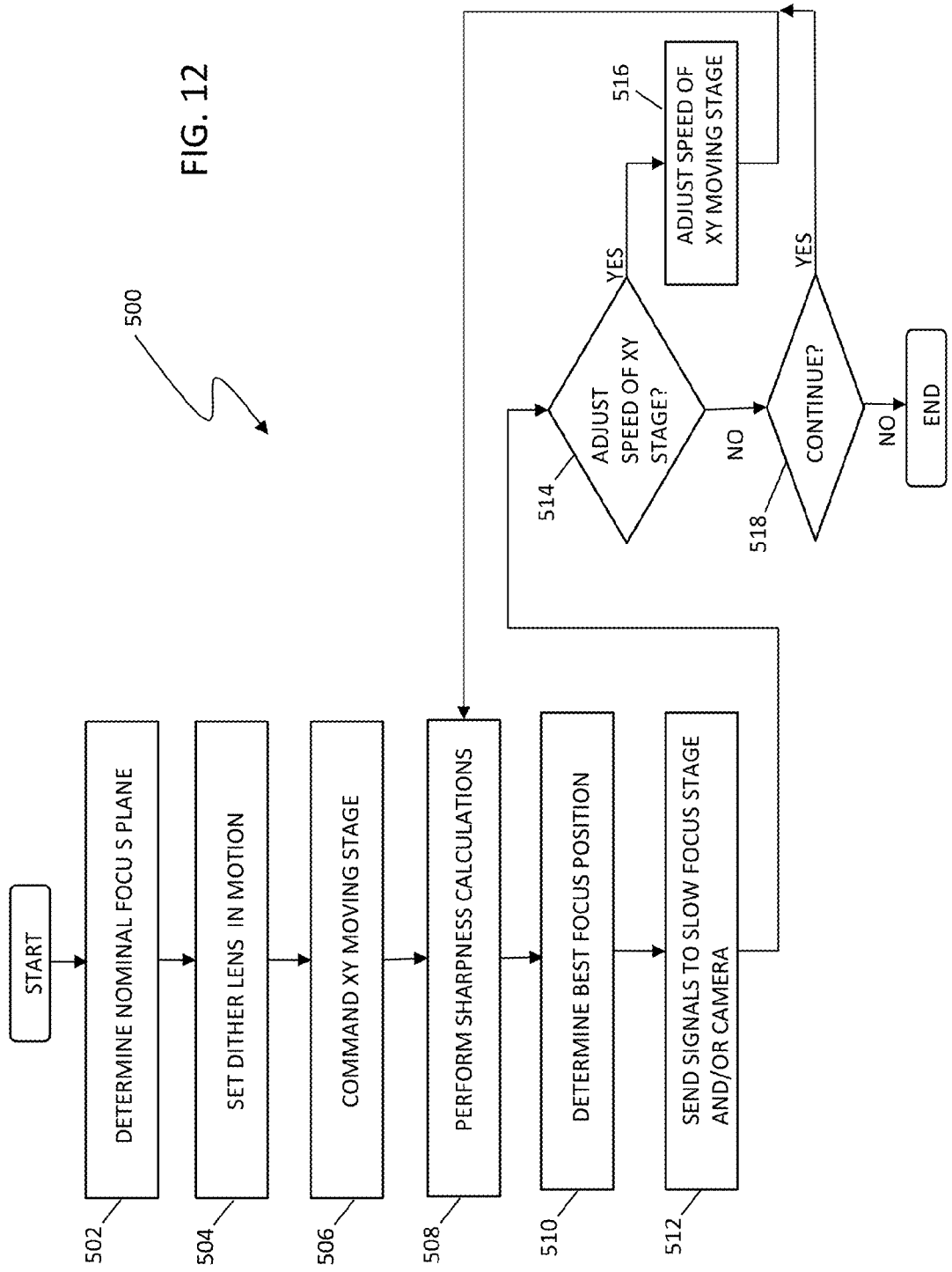
FIG. 12 is a flow diagram showing on-the-fly focus processing during scanning of a specimen under examination according to an embodiment of the system described herein.

FIG. 12 is a flow diagram 500 showing on-the-fly focus processing during scanning of a specimen under examination according to an embodiment of the system described herein. At a step 502, a nominal focus plane or reference plane may be determined for the specimen being examined. After the step 502, processing proceeds to a step 504 where a dither lens, according to the system described herein, is set to move at a particular resonant frequency. After the step 504, processing proceeds to a step 506 where the XY moving stage is commanded to move at a particular speed. It is noted that the order of steps 504 and 506, as with other steps of the processing discussed herein, may be appropriately modified in accordance with the system described herein. After the step 506, processing proceeds to a step 508 where sharpness calculations for focus points with respect to the specimen being examined are performed in connection with the motion (e.g., sinusoidal) of the dither lens according to the system described herein. The sharpness calculations may include use of contrast, chroma and/or other appropriate measures as further discussed elsewhere herein.

After the step 508, processing proceeds to step 510 where a best focus position is determined for position of a microscope objective used in connection with an image sensor to capture an image according to the system described herein. After the step 510, processing proceeds to a step 512 where a control signal concerning the best focus position is sent to a slow focus stage controlling the position (Z-axis) of the microscope objective. Step 512 also may include sending a trigger signal to the camera (e.g., image sensor) to capture an image of the specimen portion under the objective. The trigger signal may be a control signal causing capture of the image by the image sensor such as, for example, after a specific number of cycles (e.g. as related to the dither lens movement). After the step 512, processing proceeds to a test step 514 where it is determined whether the speed of the XY moving stage, holding the specimen under scan, should be adjusted. The determination may be made according to look ahead processing techniques using sharpness and/or other information of multiple zones in a focus field of view, as further discussed in detail elsewhere herein. If, at the test step 514, it is determined that the speed of the XY stage is to be adjusted, then processing proceeds to a step 516 where the speed of the XY moving stage is adjusted. After the step 516, processing proceeds back to the step 508. If, at the test step 514, it is determined that no adjustments to the speed of the XY moving stage are to be made, then processing proceeds to a test step 518 where it is determined whether focus processing is to continue. If processing is to continue, then processing back to the step 508. Otherwise, if processing is not continue (e.g., the scanning of the current specimen is complete), then focus processing is ended and processing is complete.

Figure 13:
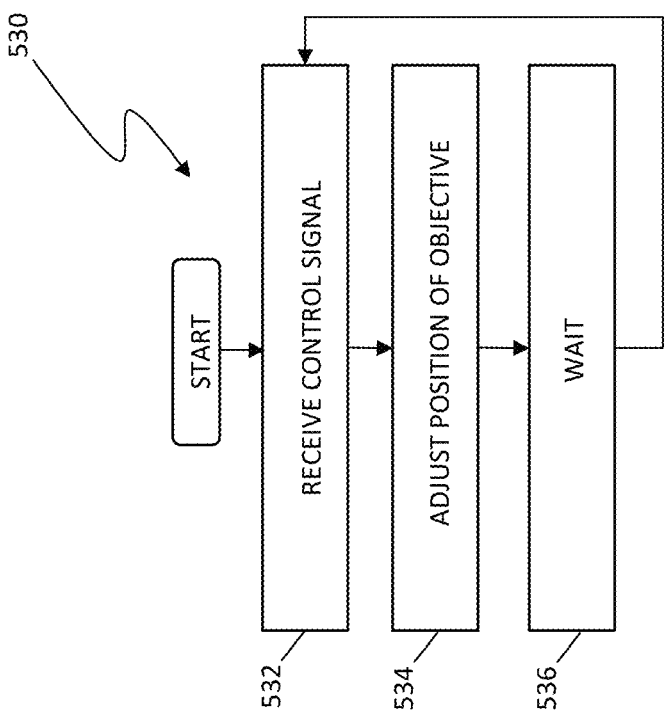
FIG. 13 is flow diagram showing processing at the slow focus stage according to an embodiment of the system described herein.

FIG. 13 is flow diagram 530 showing processing at the slow focus stage according to an embodiment of the system described herein. At a step 532, the slow focus stage, that controls a position (e.g., along the Z-axis) of a microscope objective, receives a control signal with information for adjusting a position of the microscope objective that is examining a specimen. After the step 532, processing proceeds to a step 534 where the slow focus stage adjusts the position of the microscope objective according to the system described herein. After the step 534, processing proceeds to a waiting step 536 where the slow focus stage waits to receive another control signal. After the step 536, processing proceeds back to the step 532.

Figure 14:
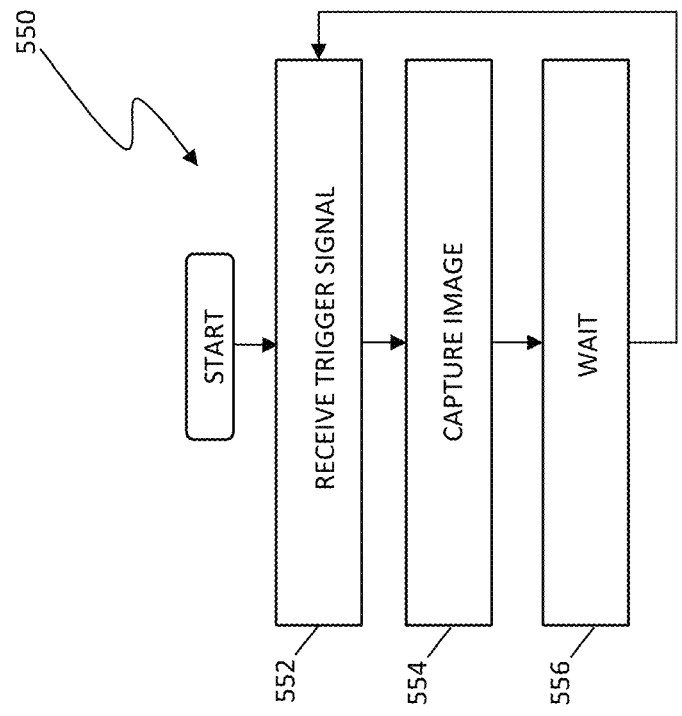
FIG. 14 is a flow diagram showing image capture processing according to an embodiment of the system described herein.

FIG. 14 is a flow diagram 550 showing image capture processing according to an embodiment of the system described herein. At a step 552, an image sensor of a camera receives a trigger signal and/or other instruction that triggers processing to capture an image of a specimen under microscopic examination. In various embodiments, the trigger signal may be received from a control system that controls triggering of the image sensor image capture processing after a specific number of cycles of motion of a dither lens used in focus processing according to the system described herein. Alternatively, the trigger signal may be provided based on a position sensor on the XY moving stage. In an embodiment, the position sensor may be a Renishaw Linear Encoder Model No. T1000-10A. After the step 552, processing proceeds to a step 554, where the image sensor captures an image. As discussed in detail herein, the captured image by the image sensor may be in focus in connection with operation of a focusing system according to the system described herein. Captured images may be stitched together in accordance with other techniques referenced herein. After the step 554, processing proceeds to a step 556 where the image sensor waits to receive another trigger signal. After the step 556, processing proceeds back to the step 552.

Figure 15:
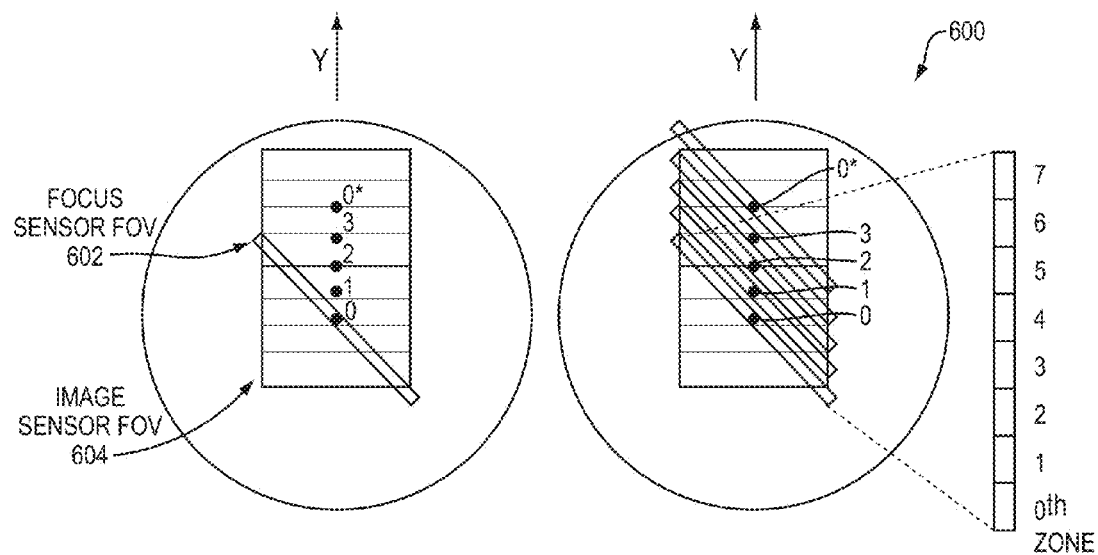
FIG. 15 is a schematic illustration showing an alternative arrangement for focus processing according to an embodiment of the system described herein.

FIG. 15 is a schematic illustration 600 showing an alternative arrangement for focus processing according to an embodiment of the system described herein. A windowed focus sensor may have a frame field of view (FOV) 602 that may be tilted or otherwise positioned to diagonally scan a swath substantially equal to the width of the imaging sensor frame FOV 604. As described herein, the window may be tilted in the direction of travel. For example, the frame FOV 602 of the titled focus sensor may be rotated to 45 degrees which would have an effective width of 0.94×0.707=0.66 mm at the object (tissue). The frame FOV 604 of the imaging sensor may have an effective width of 0.588 mm, therefore, as the XY moving stage holding the tissue moves under the objective, the titled focus sensor frame FOV 602 sees the edges of the swath observed by the image sensor. In the view, multiple frames of the tilted focus sensor are shown superimposed on the image sensor frame FOV 604 at intermediate positions at times 0, 1, 2 and 3. Focus points may be taken at three points between the centers of adjacent frames in the focus column. Focus positions 0, 1, 2, and 3 are used to extrapolate the best focus position for the next snapped frame at position 0*. The scan time for this method would be similar to the methods described elsewhere herein. While the frame FOV 602 of the titled focus sensor has a shorter look ahead, in this case 0.707×(0.94−0.432)/2=0.18 mm or the tilted focus sensor encroaches 42% into the next frame to be acquired, the frame FOV 602 of the tilted focus sensor, being oblique with respect to the image sensor frame FOV 604, sees the tissue on the edges of the scan swath which may be advantageous in certain cases to provide edge focus information.

Figure 16:
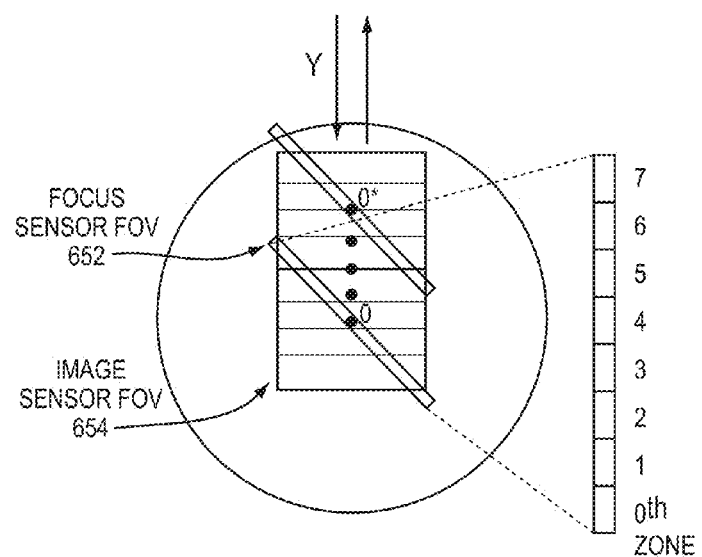
FIG. 16 is a schematic illustration showing an alternative arrangement for focus processing according to another embodiment of the system described herein.

FIG. 16 is a schematic illustration 650 showing an alternative arrangement for focus processing according to another embodiment of the system described herein. As in the illustration 650, the frame FOV 652 of the titled focus sensor and the frame FOV 654 of the image sensor is shown. The frame FOV 652 of the tilted sensor may be used to acquire focus information on the forward pass across the tissue. In the backward pass the imaging sensor snaps frames while the focus stage adjusts using the prior forward pass focus data. If one wanted to take focus data at every image frame skipping intermediate positions 0, 1, 2, 3 in the prior method, the XY moving stage could move 4× the speed in the forward pass given the high rate of focus point acquisition. For example, for a 15 mm×15 mm at 20×, a column of data is 35 frames. Since the focus data is acquired at 120 points per second, the forward pass can be executed in 0.3 seconds (35 frames/120 focus points per second). The number of columns in this example is 26, therefore the focus portion can be done in 26×0.3 or 7.6 seconds. The image acquisition at 30 fps is about 32 seconds. Thus the focus portion of the total scan time is only 20%, which is efficient. Further, if focus were allowed to skip every other frame, the focus portion of the scan time would further drop substantially.

It is noted that, in other embodiments, the focus strip of the focus sensor may be positioned at other locations within the field of view, and at other orientations, to sample adjacent columns of data to provide additional look ahead information that may be used in connection with the system described herein.

The XY moving stage conveying the slide may repeat the best focus points produced on the forward travel with respect to those produced on the backward travel. For a 20×0.75 NA objective where the depth of focus is 0.9 micron, it would be desirable to repeat to about 0.1 micron. Stages may be constructed that meet 0.1 micron forward/backward repeatability and, accordingly, this requirement is technically feasible, as further discussed elsewhere herein.

In an embodiment, a tissue or smear on a glass slide being examined according to the system described herein may cover the entire slide or approximately a 25 mm×50 mm area. Resolutions are dependent on the numerical aperture (NA) of the objective, the coupling medium to the slide, the NA of the condenser and the wavelength of light. For example, at 60×, for a 0.9 NA microscope objective, plan apochromat (Plan APO), in air at green light (532 nm), the lateral resolution of the microscope is about 0.2 um with a depth of focus of 0.5 um.

In connection with operations of the system described herein, digital images may be obtained by moving a limited field of view via a line scan sensor or CCD array over the area of interest and assembling the limited field of views or frames or tiles together to form a mosaic. It is desirable that the mosaic appear seamless with no visible stitch, focus or irradiance anomalies as the viewer navigates across the entire image.

Figure 17:
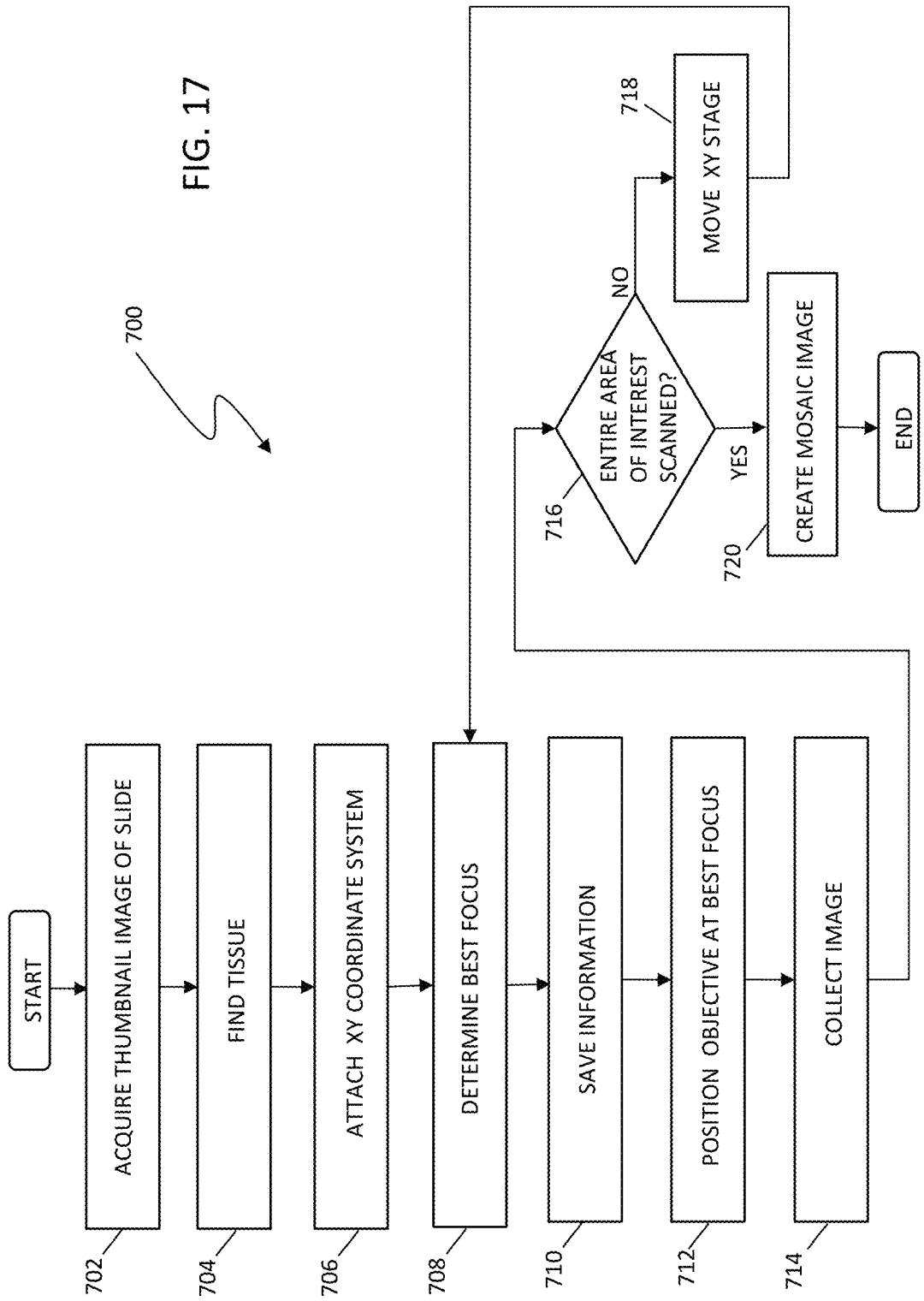
FIG. 17 is a flow diagram showing processing to acquire a mosaic image of tissue on a slide according to an embodiment of the system described herein.

FIG. 17 is a flow diagram 700 showing processing to acquire a mosaic image of tissue on a slide according to an embodiment of the system described herein. At a step 702, a thumbnail image of the slide may be acquired. The thumbnail image may be a low resolution on the order of a 1× or 2× magnification. If a barcode is present on the slide label the barcode may be decoded and attached to the slide image at this step. After the step 702, processing proceeds to a step 704 where the tissue may be found on the slide using standard image processing tools. The tissue may be bounded to narrow the scan region to a given area of interest. After the step 704, processing proceeds to a step 706 where an XY coordinate system may be attached to a plane of the tissue. After the step 706, processing may proceed to a step 708 where one or more focus points may be generated at regular X and Y spacing for the tissue and best focus may be determined using a focus technique, such as one or more of the on-fly-focusing techniques discussed elsewhere herein. After the step 708, processing may proceed to a step 710 where the coordinates of desired focus points, and/or other appropriate information, may be saved and may be referred to as anchor points. It is noted that where frames lie between the anchor points, a focus point may be interpolated.

After the step 710, processing may proceed to a step 712 where the microscope objective is positioned at the best focus position in accordance with the techniques discussed elsewhere herein. After the step 712 processing proceeds to a step 714 where an image is collected. After the step 714, processing proceeds to a test step 716 where it is determined whether an entire area of interest has been scanned and imaged. If not, then processing proceeds to a step 718 where the XY stage moves the tissue in the X and/or Y directions according to the techniques discussed elsewhere herein. After the step 718, processing proceeds back to the step 708. If at the test step 716, it is determined that an entire area of interest has been scanned and imaged, then processing proceeds to a step 720 where the collected image frames are stitched or otherwise combined together to create the mosaic image according to the system described herein and using techniques discussed elsewhere herein (referring, for example, to U.S. Patent App. Pub. No. 2008/0240613). After the step 720, processing is complete. It is noted that other appropriate sequences may also be used in connection with the system described herein to acquire one or more mosaic images.

For advantageous operation of the system described herein, z positional repeatability may be repeatable to a fraction of the depth of focus of the objective. A small error in returning to the z position by the focus motor is easily seen in a tiled system (2D CCD or CMOS) and in the adjacent columns of a line scan system. For the resolutions mentioned above at 60×, a z peak repeatability on the order of 150 nanometer or less is desirable, and such repeatability would, accordingly, be suitable for other objectives, such as 4×, 20× and/or 40× objectives.

According further to the system described herein, various embodiments for a slide stage system including an XY stage are provided for pathology microscopy applications that may be used in connection with the features and techniques for digital pathology imaging that are discussed herein, including, for example, functioning as the XY moving stage 130 discussed elsewhere herein in connection with on-the-fly focusing techniques. According to an embodiment, and as further discussed in detail elsewhere herein, an XY stage may include a stiff base block. The base block may include a flat block of glass supported on raised bosses and a second block of glass having a triangular cross-section supported on raised bosses. The two blocks may be used as smooth and straight rails or ways to guide a moving stage block.

Figure 18:
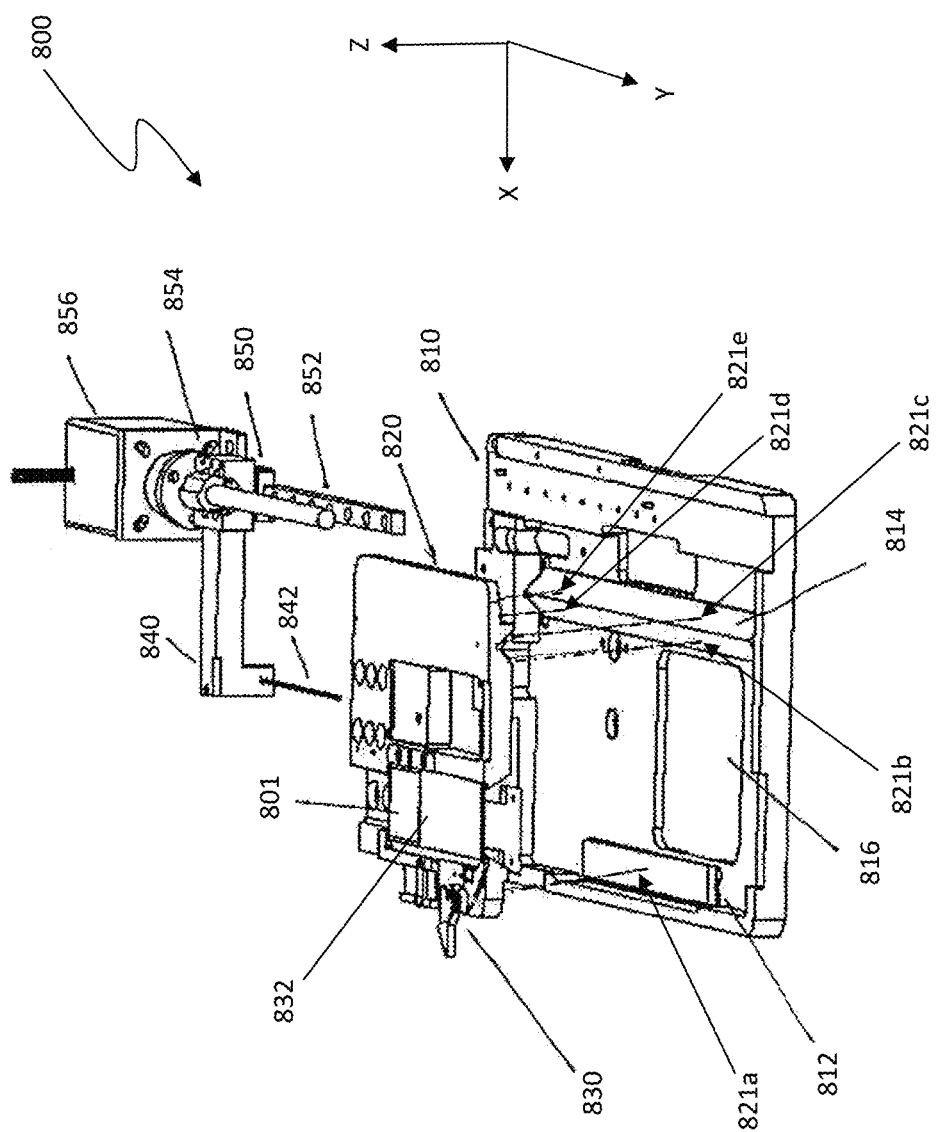
FIG. 18 is a schematic illustration showing an implementation of an precision stage (e.g., a Y stage portion) of an XY stage according to an embodiment of the system described herein.

FIG. 18 is a schematic illustration showing an implementation of a precision stage 800 (e.g., a Y stage portion) of an XY stage according to an embodiment of the system described herein. For example, the precision stage 800 may achieve z peak repeatability on the order of 150 nanometers or less over a 25 mm×50 mm area. As further discussed elsewhere herein, the precision stage 800 may be used in connection with features and techniques discussed elsewhere herein, including, for example, functioning in connection with the XY moving stage 130 discussed with respect to the on-the-fly focusing techniques. The precision stage 800 may include a stiff base block 810 where a flat block 812 of glass is supported on raised bosses. The spacing of these bosses are such that the sag, due to the weight of the precision stage 800, of the glass blocks on the simple supports are minimized. A second block of glass 814 with a triangular cross-section is supported on raised bosses. The glass blocks 812, 814 may be adhesively bonded to the base block 810 with a semi-rigid epoxy which does not strain the glass blocks. The glass blocks 812, 814 may be straight and polished to one or two waves of light at 500 nm. A material of low thermal expansion, such as Zerodur, may be employed as a material for the glass blocks 812, 814. Other appropriate types of glass may also be used in connection with the system described herein. A cut-out 816 may allow light from a microscope condenser to illuminate the tissue on the slide.

The two glass blocks 812, 814 may be used as smooth and straight rails or ways to guide a moving stage block 820. The moving stage block 820 may include hard plastic spherical shaped buttons (e.g., 5 buttons) that contact the glass blocks, as illustrated at positions 821a-e. Because these plastic buttons are spherical, the contact surface may be confined to a very small area <<0.5 mm) determined by the modulus of elasticity of the plastic. For example, PTFE or other thermoplastic blend plus other lubricant additives from GGB Bearing Technology Company, UK may be used and cast into the shape of the contact buttons of approximately 3 mm diameter. In an embodiment, the coefficient of friction between the plastic button and polished glass should be as low as possible, but it may be desirable to avoid using a liquid lubricant to save on instrument maintenance. In an embodiment, a coefficient of frictions between 0.1 and 0.15 may be readily achieved running dry.

Figure 19B:
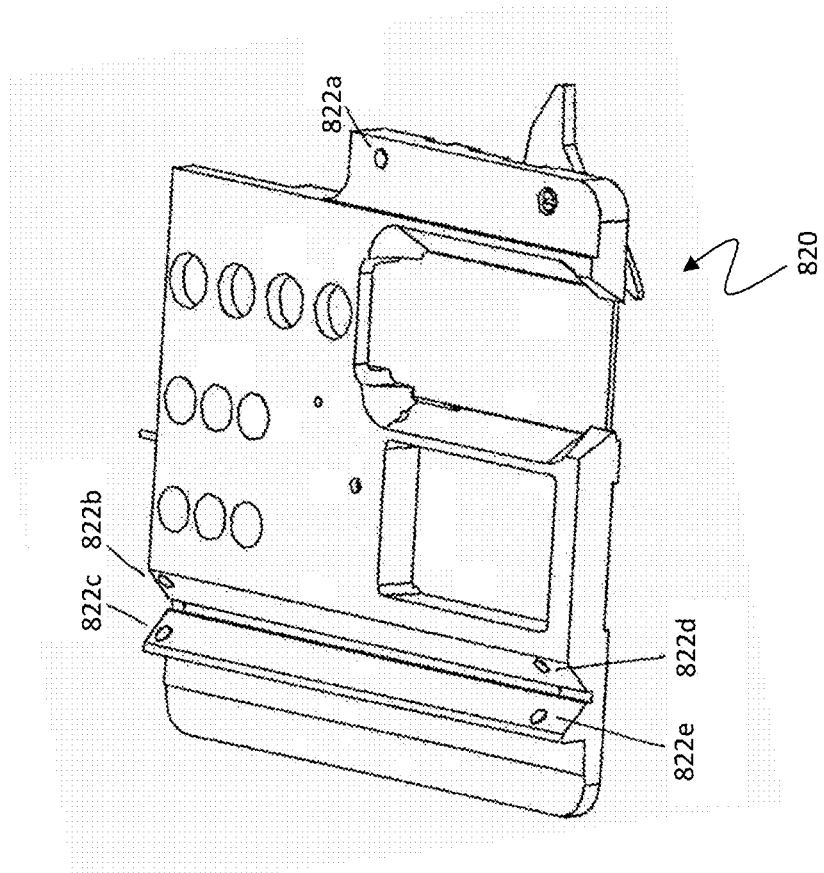
FIGS. 19A and 19B are more detailed views of the moving stage block of the precision stage according to an embodiment of the system described herein
Figure 19A:
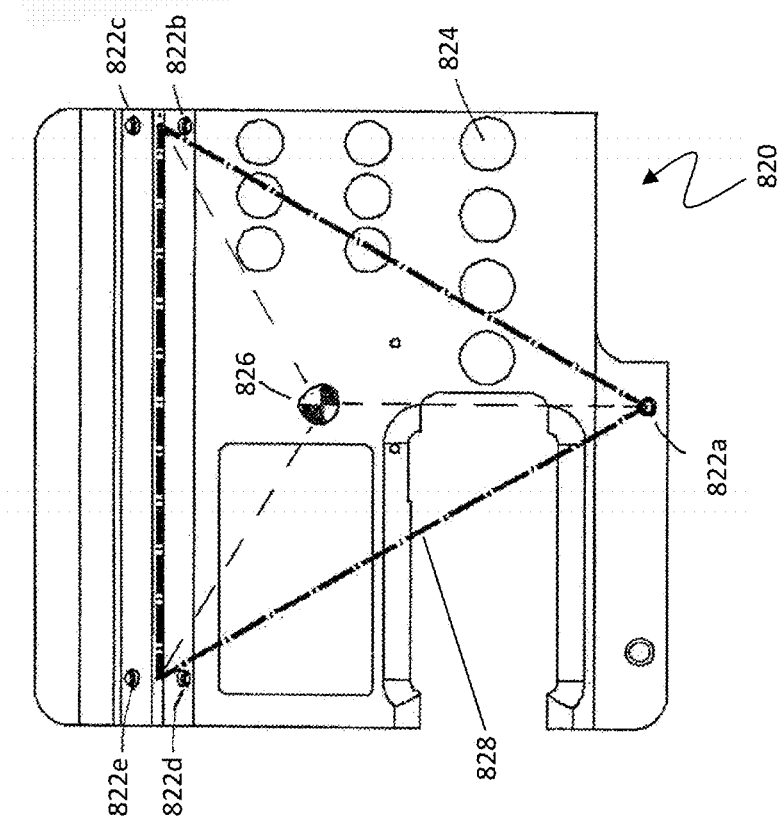

FIGS. 19A and 19B are more detailed views of the moving stage block 820 according to an embodiment of the system described herein showing the spherically shaped buttons 822a-e that contact the glass blocks 810, 812 at the positions 821a-e. The buttons may be arranged in positions that allow for excellent stiffness in all directions other than the driving direction (Y). For example, two plastic buttons may face each other to contact sides of the triangular shape glass block 814 (i.e. 4 buttons 822b-e) and one plastic button 822a is positioned to contact the flat glass block 812. The moving stage block 820 may include one or more holes 824 to be light-weighted and shaped to put the center of gravity at the centroid 826 of the triangle formed by the position of plastic support buttons 822a-e. In this manner, each of the plastic buttons 822a-e at the corners of the triangle 828 may have equal weight at all times during motion of the stage 800.

Referring back to FIG. 18, a slide 801 is clamped via a spring loaded arm 830 in the slide nest 832. The slide 801 may be manually placed in the nest 832 and/or robotically placed in the nest 832 with an auxiliary mechanism. A stiff cantilever arm 840 supports and rigidly clamps the end of small diameter flexural rod 842 that may be made of a high fatigue strength steel. In one example, this diameter may be 0.7 mm. The other end of the rod flexure 842 may be attached to the centroid location 826 on the moving stage 820. The cantilever arm 840 may be attached to a bearing block 850 which may run via a recirculating bearing design on a hardened steel rail 852. A lead screw assembly 854 may be attached to the bearing block 850 and the lead screw assembly 854 may be rotated by a stepper motor 856. Suitable components for the elements noted above may be available through several companies, such as THK in Japan. The lead screw assembly 854 drives the bearing block 850 on the rail 852 which pulls or pushes the moving stage block 820 via the rod flexure 842.

The bending stiffness of the rod flexure 842 may be a factor greater than 6000× less than the stiffness of the moving stage block 820 on its plastic pads (this is a stiffness opposing a force orthogonal to plane of the moving stage in the z direction). This effectively isolates the moving stage block 820 from up down motions of the bearing block 850/cantilever arm 840 produced by bearing noise.

The careful mass balancing and attention to geometry in design of the precision stage 800 described herein minimizes moments on the moving stage block 820 which would produce small rocking motions. Additionally, since the moving stage block 820 runs on polished glass, the moving stage block 820 has z position repeatability of less than 150 nanometer peak sufficient for scanning at 60× magnification. Since the 60× condition is the most stringent, other lower magnifications such as 20× and 40× high NA objectives also show suitable performance similar to the performance obtained under 60× conditions.

Figure 20:
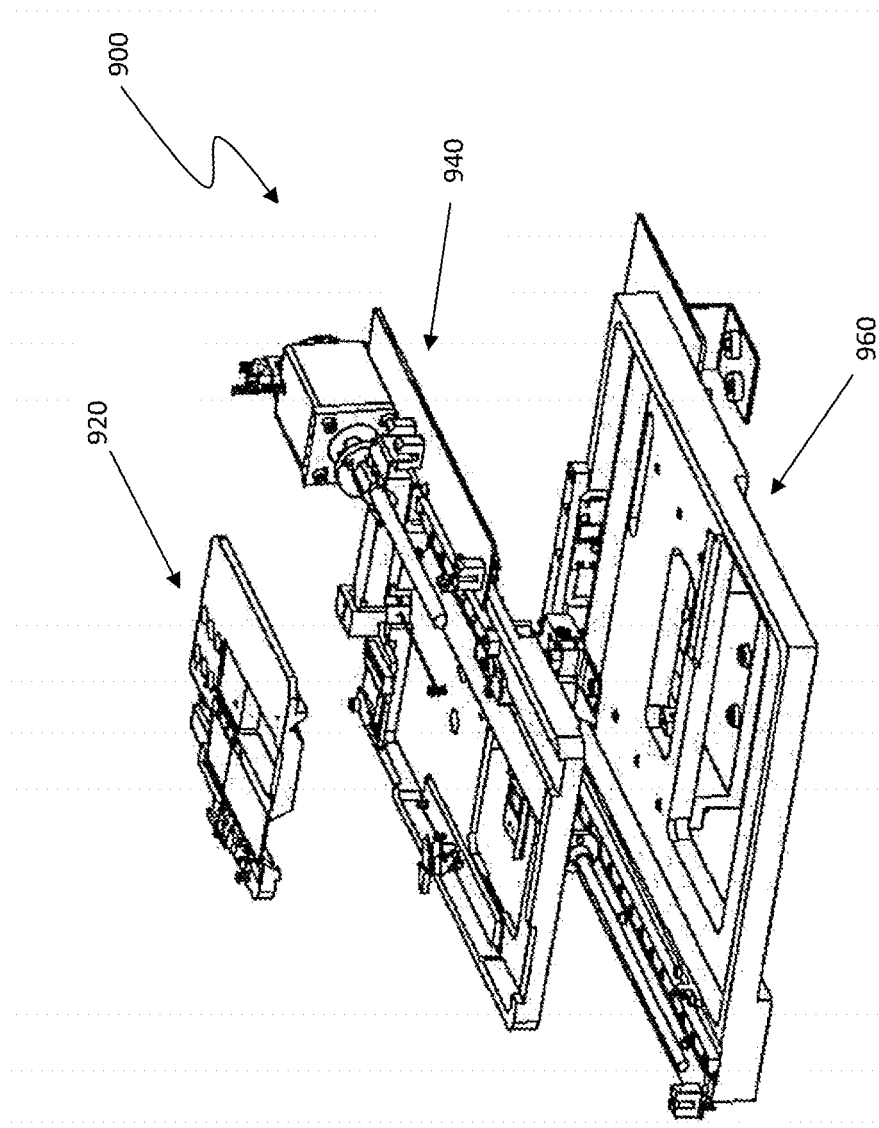
FIG. 20 shows an implementation of an entire XY compound stage according to the precision stage features discussed herein and including a Y stage, an X stage and a base plate according to an embodiment of the system described herein.

FIG. 20 shows an implementation of an entire XY compound stage 900 according to the precision stage features discussed herein and including a Y stage 920, an X stage 940 and a base plate 960 according to an embodiment of the system described herein. In this case, a base block for the Y stage 920 becomes the X stage 940 that is a moving stage in the X direction. A base block for the X stage 940 is the base plate 960 that may be fastened to ground. The XY compound stage 900 provides for repeatability in the Z direction on the order of 150 nanometer and repeatabilities on the order of 1-2 microns (or less) in the X and Y directions according to the system described herein. If the stages include feedback position via a tape-scale, such as those produced by Renishaw of Gloucestershire, England, sub-micron accuracies are achievable according to the system described herein.

The stage design according to the system described herein may be superior to spherical bearing supported moving stages in that an XY stage according to the system described herein does not suffer from repeatability errors due to non-spherical ball bearings or non-cylindrical cross roller bearings. In addition, in recirculating bearing designs, a new ball complement at different size balls may cause non-repeatable motion. An additional benefit of the embodiments described herein is the cost of the stage. The glass elements utilize standard lapping and polishing techniques and are not overly expensive. The bearing block and lead screw assembly do not need to be particularly high quality in that the rod flexure decouples the moving stage from the bearing block.

According further to the system described herein, it is advantageous to reduce and/or otherwise minimize scan times during the scanning of digital pathology slides. In clinical settings, a desirable work flow is to place a rack of slides into a robotic slide scanning microscope, close the door and command the system to scan the slides. It is desirable that no user intervention be needed until all slides are scanned. The batch size may include multiple slides (e.g., 160 slides) and the time to scan all slides is called the batch time. The slide throughput is the number of slides per hour processed. The cycle time is the time between each available slide image that is ready for viewing.

The cycle time may be influenced by the following steps in acquiring an image: (a) robotically pick up the slide; (b) create a thumbnail view or overview image of the slide tissue area and label; (c) calculate an area of interest bounding the slide tissue; (d) pre-scan the bounded tissue area to find a regular array of best focused points on the tissue; (e) scan the tissue according to movement of a stage and/or sensor; (f) create a compressed output image ready for viewing; and (g) deposit the slide, ready for next slide. It is noted that step (d) may not be necessary if dynamic focusing or "on-the-fly" focusing is performed according to the system described herein, and in which scanning/image acquisition time may, accordingly, be reduced as a result of use of the on-the-fly focusing techniques.

The system described herein may further involve eliminating or significantly shortening the time to execute steps (a), (b), (c) and (g). According to various embodiments of the system described herein, these gains may be accomplished, for example, by using a caching concept where above-noted steps (a), (b), (c) and (g) for one slide are overlapped in time with steps (d), (e) and (f) for another slide, as further discussed in detail herein. In various embodiments, the overlapping of steps (a), (b) and (c) for one slide with steps (d), (e) and (f) for another slide may provides a gain of 10%, 25% or even 50% compared to a system wherein steps (a), (b) and (c) for one slide are not overlapped with steps (d), (e) and (f) for another slide.

Figure 21:
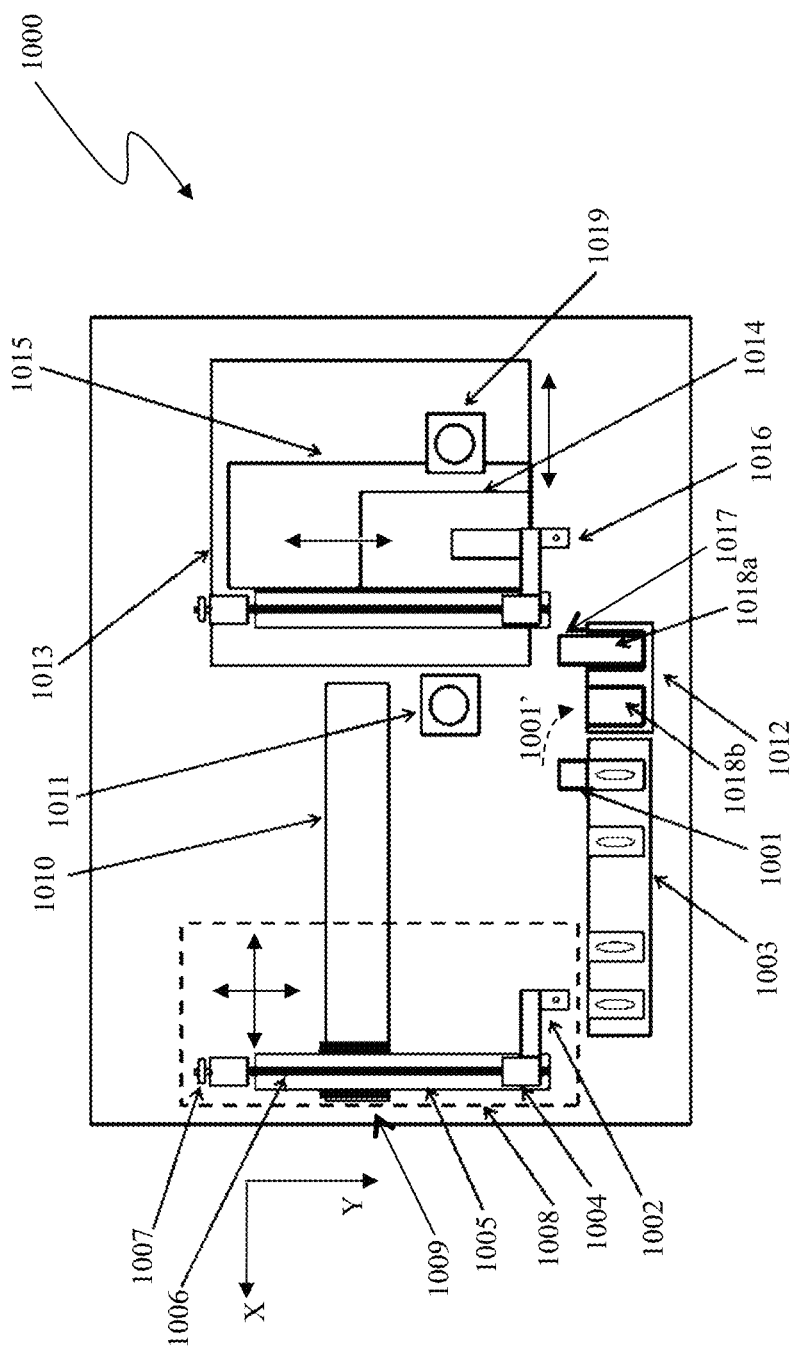
FIG. 21 is a schematic illustration showing a slide caching device according to an embodiment of the system described herein.

FIG. 21 is a schematic illustration showing a slide caching device 1000 according to an embodiment of the system described herein. A slide pickup head 1002 may be positioned to pick up a slide 1001. The pickup head 1002 may use a mechanical device and/or a vacuum device to pick up the slide 1001. The slide 1001 may be one of a collection of slides in the batch, for example, a batch of 160 slides. The collection of slides may be disposed in a slide rack 1003. The pickup head 1002 is attached to a bearing car or block 1004 which travels on a steel rail 1005. The bearing block 1004 is moved by a rotating lead screw 1006. Motor counts may be detected with a rotary encoder 1007 and converted into linear travel to control slide position in the Y-direction. The elements 1002-1007 may comprise a moving assembly referred to as a slide loader/unloader 1008. The slide loader/unloader 1008 may also move on a motorized bearing car or block 1009 in the x direction on rail 1010 which allows the slide loader/unloader 1008 to move in both the X and Y directions.

In operation, a slide, while still held on the pickup head 1002, may be positioned under a low-resolution camera 1011 to obtain the thumbnail view or overview image of the slide tissue area and label (e.g., the above-noted step (b)). Once this operation is completed, step (c) may be executed and the slide is placed into a position on a slide buffer 1012. The slide buffer 1012 may include two (or more) buffer slots or positions 1018a, 1018b, and is shown including a slide 1017 in buffer position 1018a.

In an embodiment, a compound XY stage 1013 may include a stage plate 1014 that moves in the Y direction and which is mounted to a plate 1015 that moves in the x direction. The XY stage 1013 may have features and functionality similar to that discussed elsewhere herein, including, for example, features of the compound XY stage 900 discussed herein. The stage plate 1014 may further include an additional slide pickup head 1016. The pickup head 1016 may be similar to the pickup head 1012 described above. The pickup head 1016 may use a mechanical device and/or a vacuum device to pick up a slide.

The pickup head 1016 of the compound XY stage 1016 may move to the buffer position 1018a and pick up the slide 1017. The slide 1017 may now continue to one or more of the above-noted steps, including steps: (d) prescan, (e) scan and (f) create output image steps. While this processing is being executed, the slide loader/unloader 1008 may pick up another slide (e.g., slide 1001), obtain the thumbnail view of the slide 1001 using the camera 1011, and place the slide 1001 in an empty position 1018b in the slide buffer 1012, shown schematically by dotted line 1001'. When scanning is completed on the preceding slide (slide 1017), the slide pickup head 1016 of the XY compound stage 1013 may place the slide 1017 into the buffer position 1018a and pick up the next slide (slide 1001) from the buffer position 1018b that is ready for scan. The compound XY stage 1013 may move in a regular back and forth scan pattern under a high-resolution optical system microscope optics and camera 1019 to acquire a high resolution image of biological tissue in accordance with features and techniques discussed elsewhere herein. It is further noted that movements and slide selections of the compound XY stage 1013 and/or the slide loader/unloader 1008 may be controlled by one or more processors in a control system.

The slide loader/unloader 1008 may move to the buffer position 1018a and pick up the slide 1017 and deposit the slide 1017 into the slide rack 1003. This slide 1017 has completed all of the steps enumerated above. The slide loader/unloader 1008 may then continue to pick up and load another slide into the slide buffer 1012, and eventually pick up and return the slide 1001 to the slide rack 1003. Processing like that described above may continue until all slides that are in the slide rack 1003 have been scanned.

The slide caching techniques according to the system described herein provide advantageous time savings. For example, in a system at a 20×15 mm×15 mm field, the pickup time is about 25 seconds, the thumbnail acquisition is about 10 seconds, the pre-scan time is about 30 seconds and the scan time is 90 seconds. The output file generation is done concurrently with the scanning process and may add about 5 seconds. The deposit of the slide is about 20 seconds. Adding all of these times together indicates a 180 second cycle time. The XY compound stage still needs time to pick up and deposit the scanned slide which may account for about 10 seconds. Accordingly, the reduction in scan time is therefore about 1−(180−55+10)/180=25%. For systems using dynamic focus techniques, such as on-the-fly focusing as further discussed elsewhere herein, the prescan time may be eliminated, and with high data rate cameras the times not associated with pickup and deposit may reduce to 20-30 seconds. The reduction in scan time in using slide caching in this case may be about 1−(75−55+10)/75=50%.

Figures 22A, 22B:
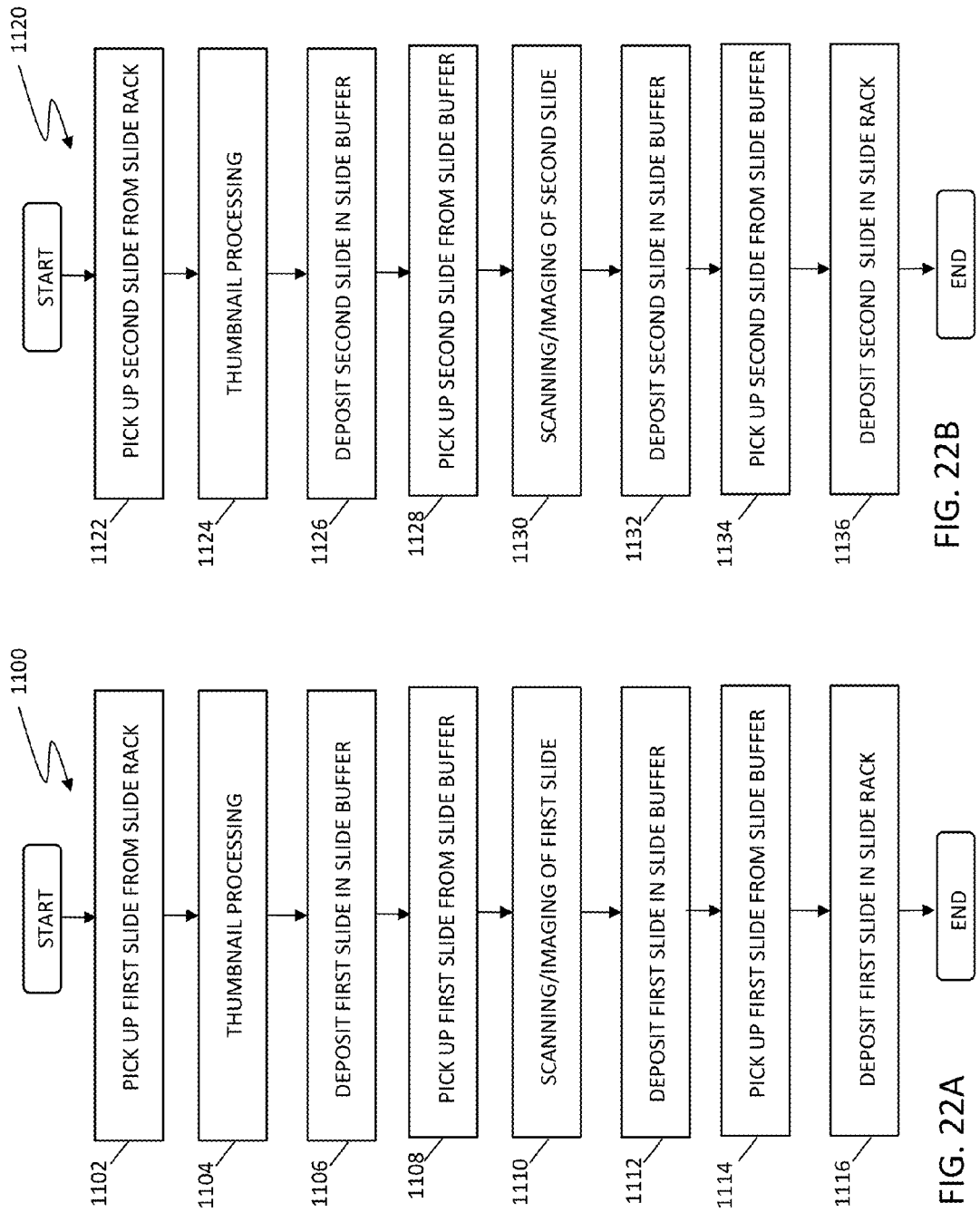
FIG. 22A is a flow diagram showing slide caching processing according to an embodiment of the system described herein in connection with a first slide.
FIG. 22B is a flow diagram showing slide caching processing according to an embodiment of the system described herein in connection with a second slide.

FIG. 22A is a flow diagram 1100 showing slide caching processing according to an embodiment of the system described herein in connection with a first slide. At a step 1102, the first slide is picked up from a slide rack. After the step 1102, processing proceeds to a step 1104 where a thumbnail image is obtained and/or other thumbnail processing, that may include determining an area of interest of tissue on the slide, is performed for the first slide. After the step 1104, processing proceeds to a step 1106 where the first slide is deposited into a slide buffer. After the step 1106, processing proceeds to a step 1108 where the first slide is picked up from the slide buffer. After the step 1108 processing proceeds to a step 1110 where the first slide is scanned and imaged according to techniques like that further discussed elsewhere herein. It is noted that in various embodiments the scanning and imaging techniques may include pre-scanning focusing steps and/or using dynamic focusing techniques, such as an on-the-fly focusing technique. After the step 1110 processing proceeds to a step 1112 where the first slide is deposited in the slide buffer. After the step 1112, processing proceeds to a step 1114 where first slide is picked up from the slide buffer. After the step 1114, processing proceeds to a step 1116 where the first slide is deposited in the slide rack. After the step 1116, processing is complete with respect to the first slide.

FIG. 22B is a flow diagram 1120 showing slide caching processing according to an embodiment of the system described herein in connection with a second slide. As discussed further herein, various steps of the flow diagram 1120 may be performed in parallel with steps of the flow diagram 1100. At a step 1122, the second slide is picked up from a slide rack. After the step 1102, processing proceeds to a step 1124 where a thumbnail image is obtained and/or other thumbnail processing, that may include determining an area of interest of tissue on the slide, is performed for the second slide. After the step 1124, processing proceeds to a step 1126 where the second slide is deposited into a slide buffer. After the step 1126, processing proceeds to a step 1128 where the second slide is picked up from the slide buffer. After the step 1128 processing proceeds to a step 1130 where the second slide is scanned and imaged according to techniques like that further discussed elsewhere herein. It is noted that in various embodiments the scanning and imaging techniques may include pre-scanning focusing steps and/or using dynamic focusing techniques, such as an on-the-fly focusing technique. After the step 1130 processing proceeds to a step 1132 where the second slide is deposited in the slide buffer. After the step 1132, processing proceeds to a step 1134 where second slide is picked up from the slide buffer. After the step 1134, processing proceeds to a step 1136 where the second slide is deposited in the slide rack. After the step 1136, processing is complete with respect to the second slide.

In accordance with an embodiment of the system described herein addressing slide caching, steps of the flow diagram 1100 with respect to the first slide may be performed by a slide caching device in parallel with the steps of the flow diagram 1120 with respect to the second slide in order to reduce cycle time. For example, the steps 1122, 1124, 1126 of the flow diagram 1120 for the second slide (e.g., the steps in connection with picking up the second slide from the slide rack, thumbnail image processing and depositing the second slide into the slide buffer) may overlap with the steps 1108, 1110, and 1112 of the flow diagram 1100 with respect to the first slide (e.g., the steps in connection with picking up the first slide from the slide buffer, scanning and imaging the first slide and depositing the first slide back in the slide buffer). Further, the steps 1134 and 1136 (e.g., steps in connection with picking up the second slide from the slide buffer and depositing the slide into the slide rack) may also overlap with the scanning steps of the first slide. Time gains of up to 50% may be obtained according to the parallel slide processing techniques according to the system described herein compared with processing one slide at a time, with additional gains possible using other aspects of the system and techniques described herein.

Figure 23A:
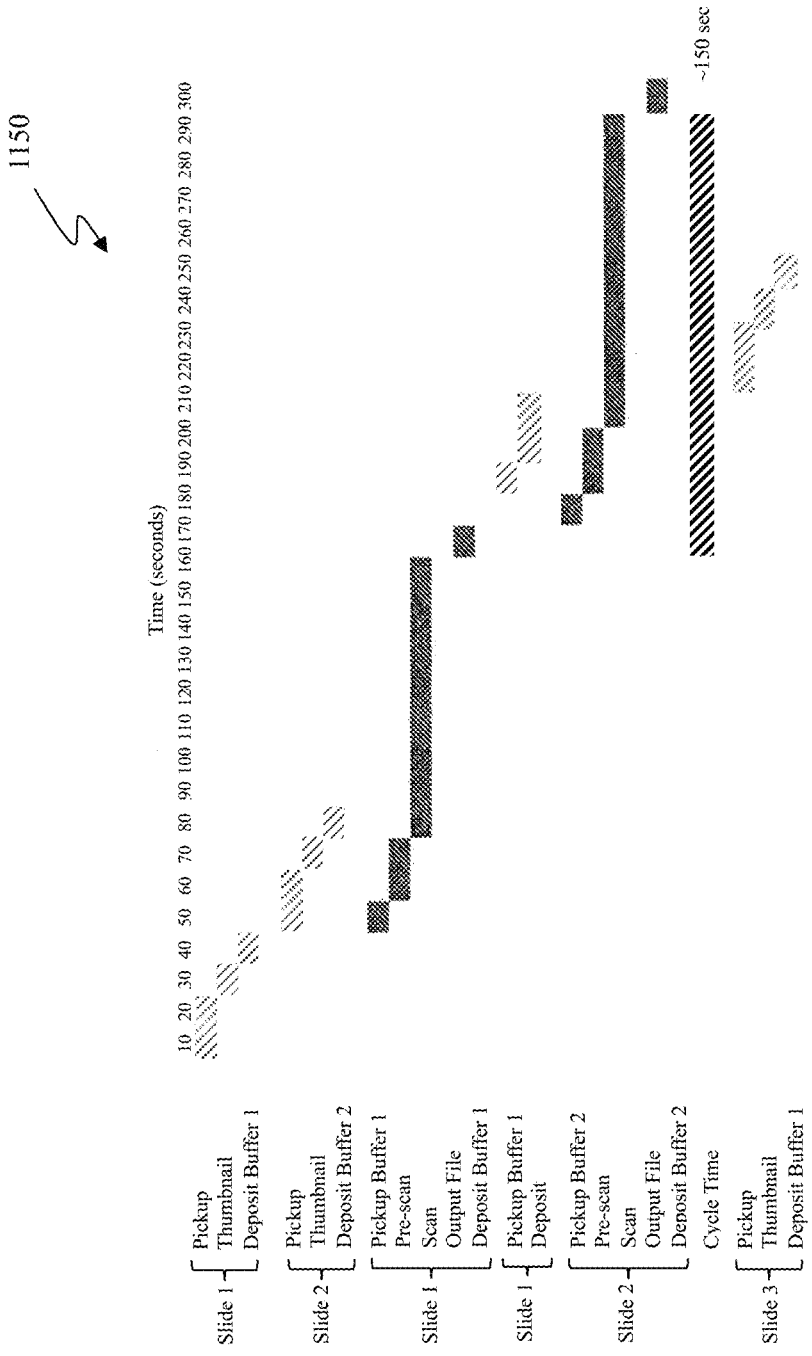
FIGS. 23A and 23B show timing diagrams using slide caching techniques according to embodiments of the system described herein and illustrating time savings according to various embodiments of the system described herein.
Figure 23B:
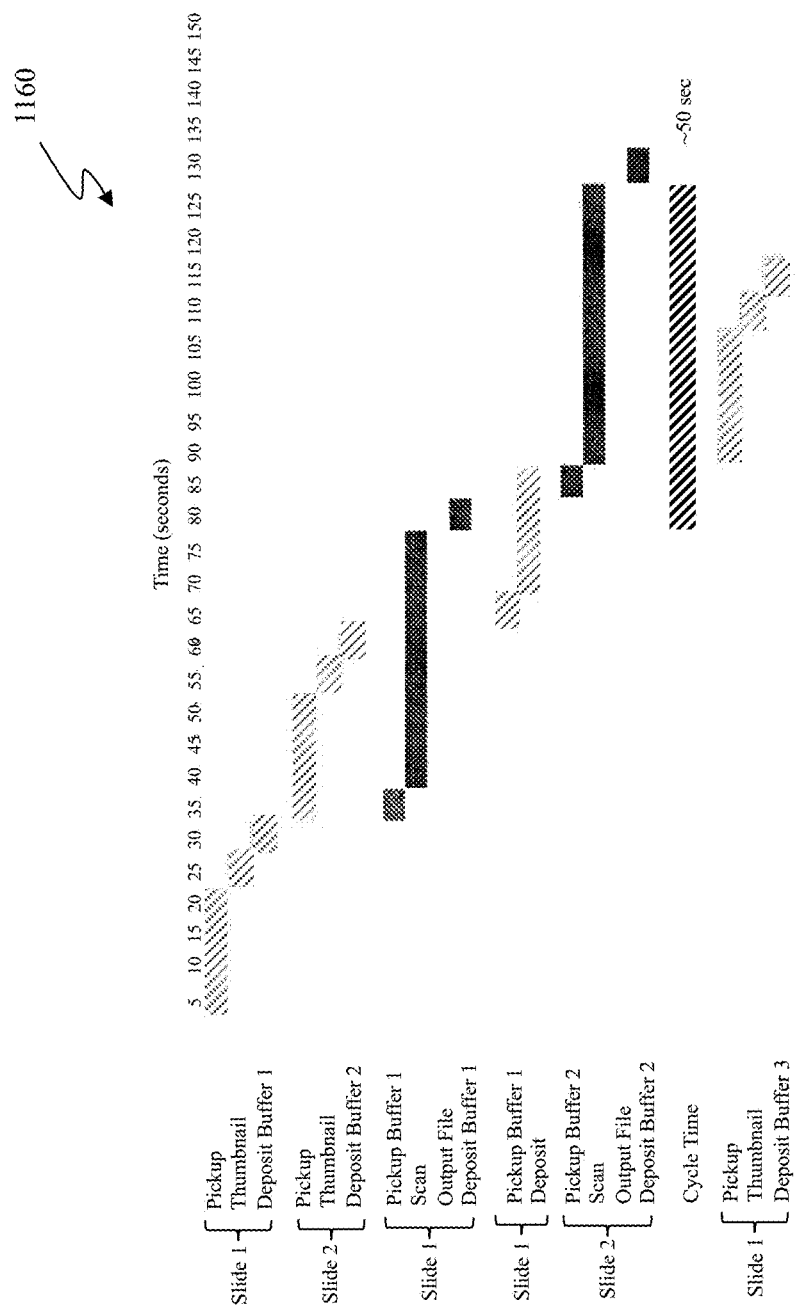

FIGS. 23A and 23B show timing diagrams using slide caching techniques according to embodiments of the system described herein and illustrating time savings according to various embodiments of the system described herein.

FIG. 23A shows the timing diagram 1150 for the scenario in which a pre-scan step is used. The timing diagram shows the timing for three slides (Slides 1, 2 and 3) over a span of approximately 300 seconds in connection with performing slide processing steps using slide caching including pickup of a slide from a slide rack, thumbnail image processing, depositing slides in the buffer, pickup from the buffer, pre-scanning, scanning slides and outputting files, depositing into the buffer and depositing into the slide rack. As illustrated, in an embodiment, the cycle time for the illustrated processing may be approximately 150 seconds.

FIG. 23B shows the timing diagram 1160 for a scenario in which an on-the-fly focusing technique is used (no pre-scan). The timing diagram shows the timing for three slides (Slides 1, 2 and 3) over a span of approximately 150 seconds in connection with performing slide moving and scanning steps using slide caching including pickup of a slide from a slide rack, thumbnail image processing, depositing slides in the buffer, pickup from the buffer, scanning slides and outputting files, depositing into the buffer and depositing into the slide rack. As illustrated, in an embodiment, the cycle time for the illustrated processing may be approximately 50 seconds.

Figure 24:
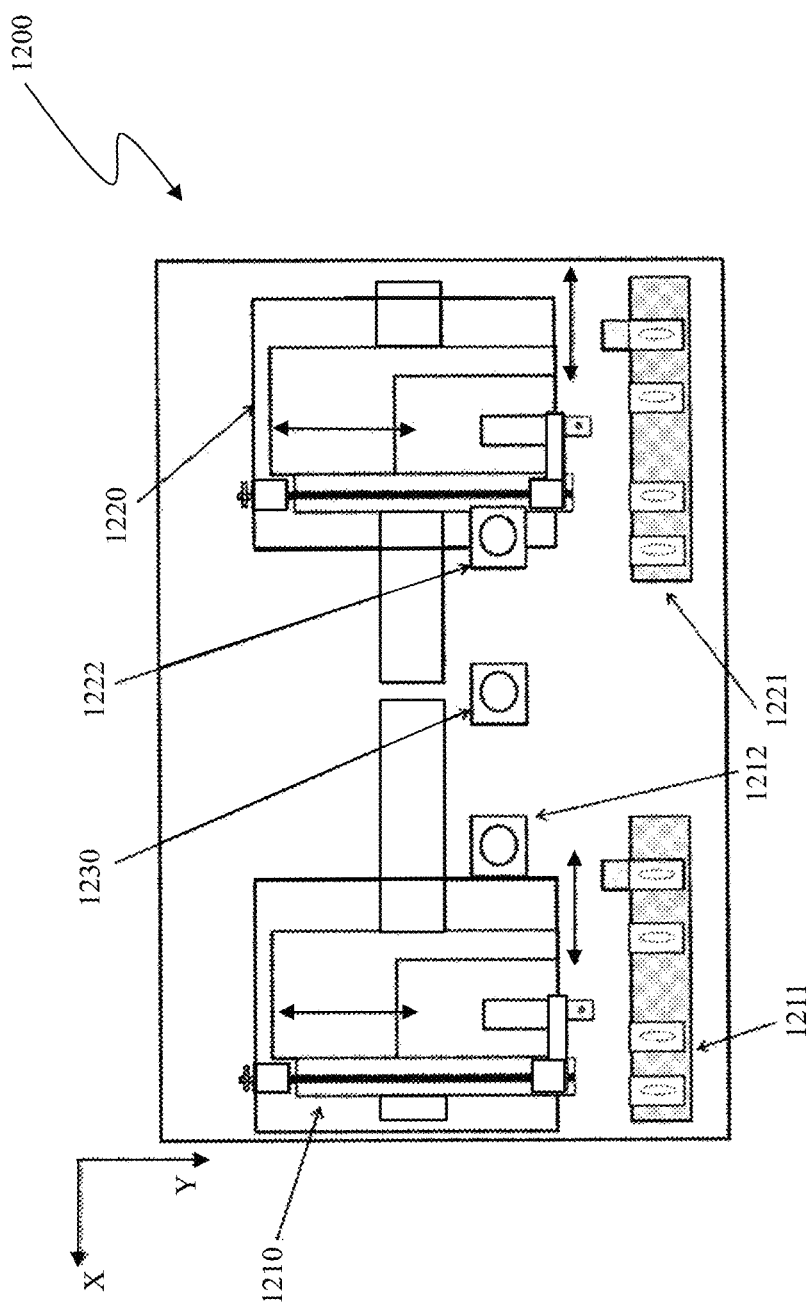
FIG. 24 is a schematic illustration showing a slide caching device according to another embodiment of the system described herein.

FIG. 24 is a schematic illustration showing a slide caching device 1200 according to another embodiment of the system described herein. In the illustrated embodiment, no buffer is required, and pickup, thumbnail and deposit times may be eliminated from the cycle time using the slide caching device 1200. The slide caching device 1200 may include two XY compound stages 1210, 1220 which operate independently. Each of the XY compound stages 1210, 1220 may have features similar to those discussed herein with respect to the XY compound stage 1013. A first slide rack 1211 may be positioned an end of the stage 1210 and a second slide rack 1221 may be positioned at an end of the stage 1220. It is noted that in connection with another embodiment of the system described herein, the first slide rack 1211 and the second slide rack 1211 may refer instead to portions of one slide rack. Two thumbnail cameras 1212, 1222 may serve each of the XY compound stages 1210, 1220. Each of the slide racks 1211, 1221 may serve slides to its companion XY compound stage 1210, 1220 with a corresponding pickup head. One microscope optical train 1230 may serve both XY compound stages 1210, 1220. For example, while one of the XY compound stages (e.g., stage 1210) is scanning a slide, the other (e.g., stage 1220) is performing its pickup, thumbnail and deposit functions with another slide. These functions may be overlapped with the scanning time. Accordingly, the cycle time may be determined by the scan time of a slide, and pickup, thumbnail and deposit times are therefore eliminated from the cycle time according to the illustrated embodiment of the system described herein.

Figures 25A, 25B:
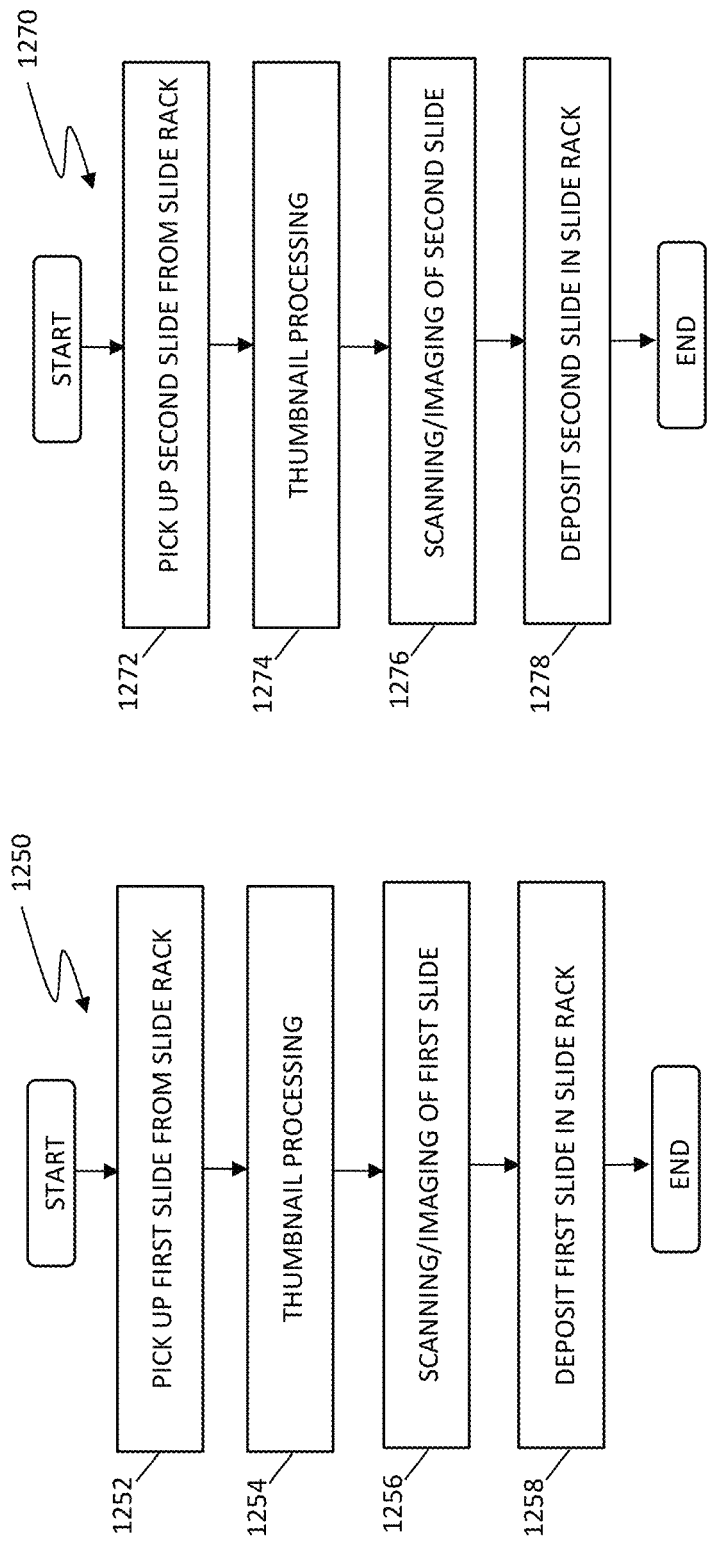
FIG. 25A is a flow diagram showing slide caching processing in connection with a first slide according to an embodiment of the system described for a slide caching device having two XY compound stages for slide processing.
FIG. 25B is a flow diagram showing slide caching processing in connection with a second slide according to an embodiment of the system described for the slide caching device having two XY compound stages for slide processing.

FIG. 25A is a flow diagram 1250 showing slide caching processing in connection with a first slide according to an embodiment of the system described for a slide caching device having two XY compound stages for slide processing. At a step 1252, the first slide is picked up from a slide rack. After the step 1252, processing proceeds to a step 1254 where the thumbnail processing is performed on the first slide. After the step 1254, processing proceeds to a step 1256 where the first slide is scanned and imaged according to techniques like that further discussed elsewhere herein. It is noted that in various embodiments the scanning and imaging techniques may include pre-scanning focusing steps and/or using dynamic focusing techniques, such as an on-the-fly focusing technique. After the step 1256, processing proceeds to a step 1258 where the first slide is deposited back into the slide rack. After the step 1258, processing is complete with respect to the first slide.

FIG. 25B is a flow diagram 1270 showing slide caching processing in connection with a second slide according to an embodiment of the system described for a slide caching device having two XY compound stages for slide processing. At a step 1272, the second slide is picked up from a slide rack. After the step 1272, processing proceeds to a step 1274 where the thumbnail processing is performed on the second slide. After the step 1274, processing proceeds to a step 1276 where the second slide is scanned and imaged according to techniques like that further discussed elsewhere herein. It is noted that in various embodiments the scanning and imaging techniques may include pre-scanning focusing steps and/or using dynamic focusing techniques, such as an on-the-fly focusing technique. After the step 1276, processing proceeds to a step 1278 where the second slide is deposited back into the slide rack. After the step 1278, processing is complete with respect to the second slide.

In accordance with an embodiment of the system described herein involving slide caching, steps of the flow diagram 1250 concerning the first slide may be performed by the slide caching device in parallel with the steps of the flow diagram 1270 concerning the second slide in order to reduce cycle time. For example, the steps 1272, 1274 and 1278 for the second slide (e.g., pickup, thumbnail processing and deposit) may overlap the step 1256 of the first slide (e.g., scanning/imaging of the first slide), and vice versa, such that the times for pickup, thumbnail processing and deposit are eliminated from the cycle time. The cycle time is accordingly determined by only the scan time of a slide according to an embodiment of the system described herein.

Figure 26:
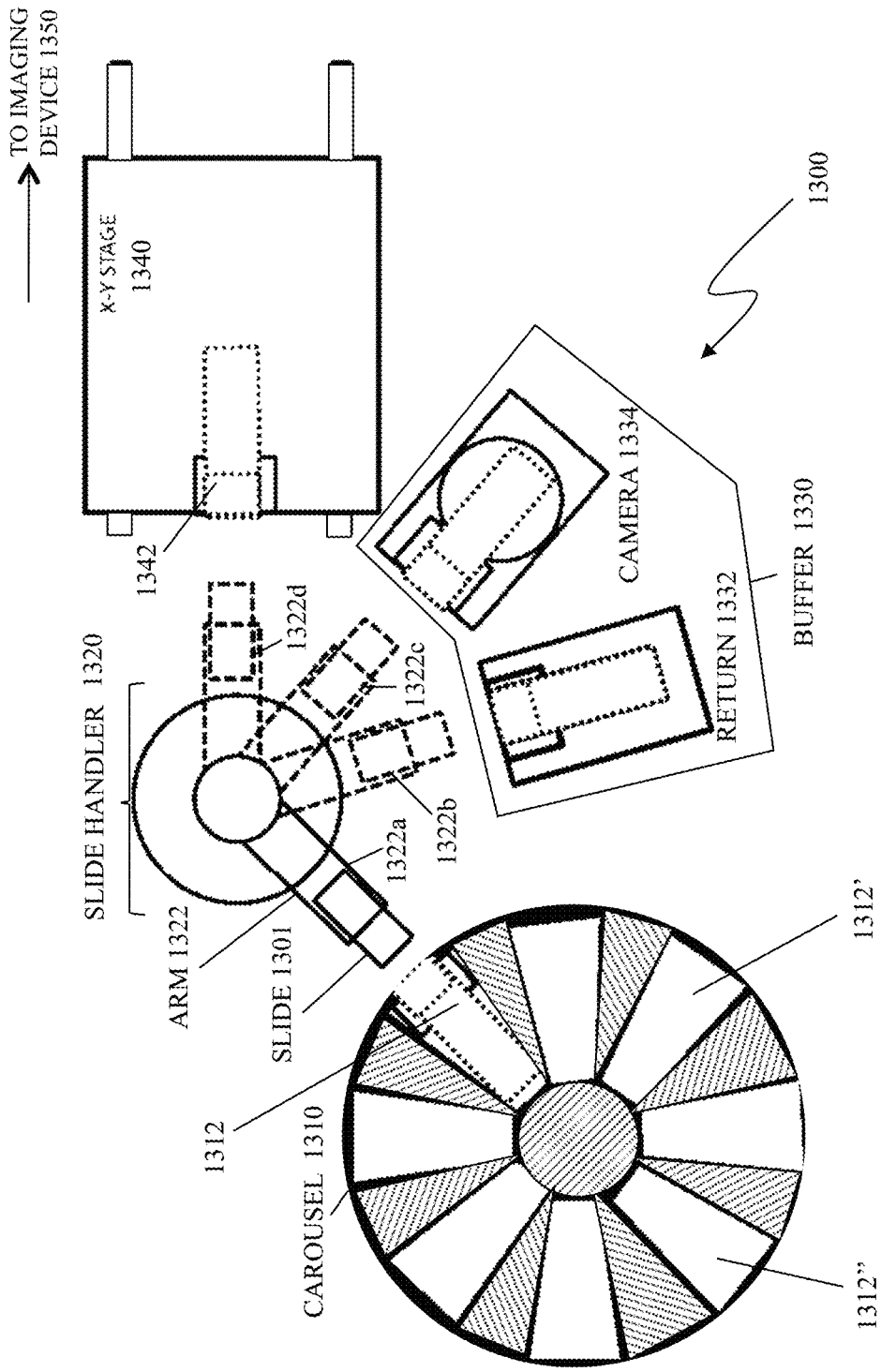
FIG. 26 is a schematic illustration showing a slide caching device according to another embodiment of the system described herein.

FIG. 26 is a schematic illustration showing a slide caching device 1300 according to another embodiment of the system described herein. The slide caching device 1300 may include a slide rack configured as a carousel 1310, a slide handler 1320, a buffer 1330 and an XY stage 1340. The carousel 1310 may include one or more positions 1312, 1312', 1312" in which slides, such as slide 1301, may placed before and/or after being imaged by an imaging device 1350 that may have features and functionality like that discussed elsewhere herein. The positions 1312, 1312', 1312" are shown as an array of wedges (e.g., 8 wedges) and, as further discussed elsewhere herein, the carousel 1310 may have a height such that multiple slide positions extend below each of the top level wedge positions 1312, 1312', 1312" that are shown. The slide handler 1320 may include an arm 1322 that acts as pickup head and may include mechanical and/or vacuum devices to pick up a slide. The arm 1322 on the slide handler 1320 may move between positions 1322a-d to move slides among the carousel 1310, the buffer 1330 and the XY stage 1340.

The buffer 1330 may include multiple buffer positions 1332, 1334. One buffer position 1332 may be designated as a return buffer position 1332 in which slides being returned from the imaging device 1350 via the XY stage 1340 may be positioned before being moved, by the slide handler 1320, back to the carousel 1310. Another buffer position 1334 may be designated as a camera buffer position 1334 in which a slide that is to be sent to the imaging device 1350 may first have a thumbnail image captured of the slide according to the techniques discussed elsewhere herein. After a thumbnail image of the slide is captured at the camera buffer position 1334, the slide may be moved to a position 1342 on the XY stage 1340 that transports the slide to the imaging device 1350 for scanning and imaging according to the techniques discussed elsewhere herein.

Figure 27:
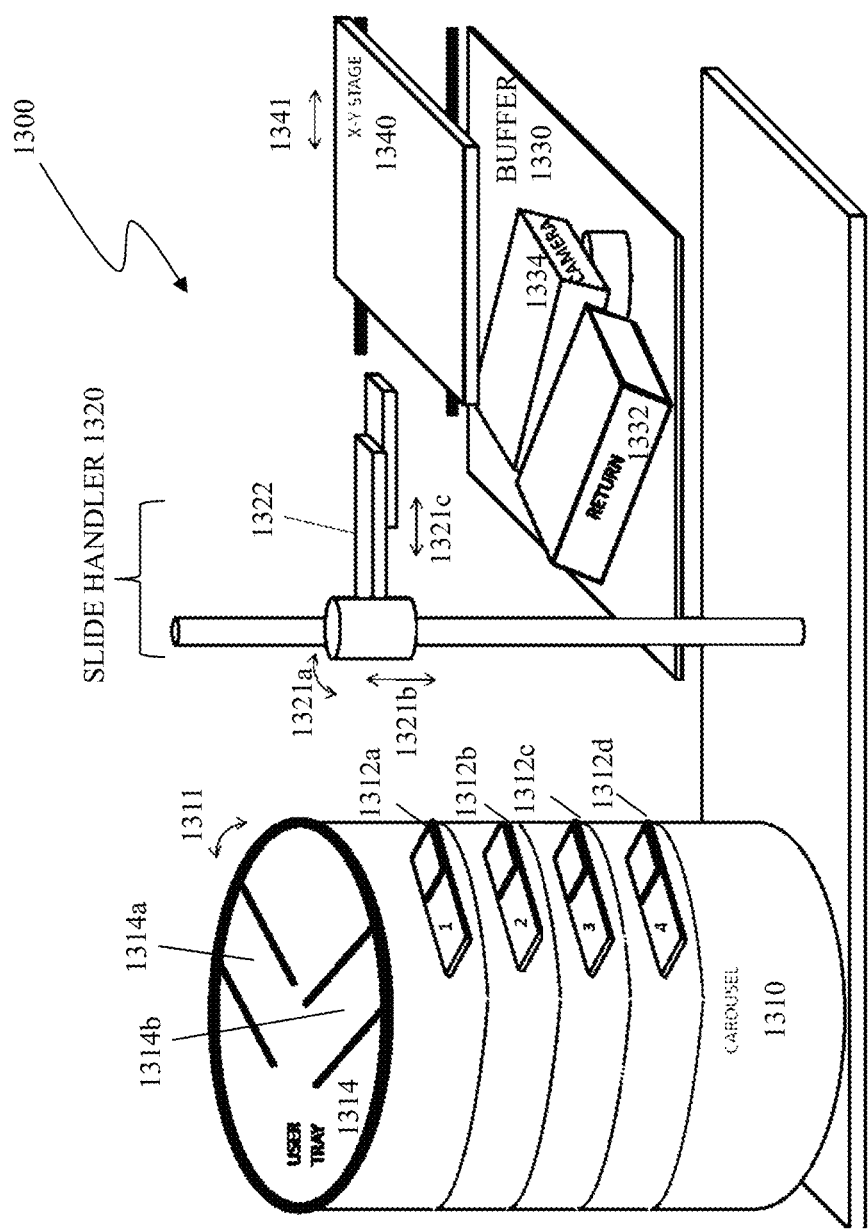
FIG. 27 is a schematic illustration showing another view of the slide caching device according to FIG. 26.

FIG. 27 is a schematic illustration showing another view of the slide caching device 1300. The components of the slide caching device 1300 may have functionality to operate with various movements and with multiple degrees of freedom of movement. For example, the carousel 1310 may be rotatable in a direction 1311 and may include multiple slide positions 1312a-d at multiple height positions at each rotational position to accommodate multiple slides (shown as Slides 1, 2, 3 and 4). In an embodiment, the multiple slide positions 1312a-d in each of the wedge positions 1312, 1312', 1312" may include positions for 40 slides, for example, positioned equidistantly within the height of the carousel 1310 that may measure, in one embodiment, 12 inches. Further, the carousel 1310 may also include a user tray 1314 having one or more slide positions 1314a,b at which a user may insert a slide to be imaged in addition to other slides in the carousel 1310. Interaction of a slide into the user tray 1314, for example lifting a cover of the user tray 1314 and/or inserting the slide into one of the positions 1314a,b of the user tray 1314, may act to trigger a by-pass mode in which a slide from the user tray 1314 is processed instead of the next slide from the wedge positions of the carousel 1310.

The arm 1322 of the slide handler 1320 is shown having at least three degrees of freedom in motion. For example, the arm 1322 may rotate in a direction 1321a in order to engage each of the carousel 1310, the buffer 1330 and the XY stage 1340. Additionally, the arm 1322 may be adjustable in a direction 1321b corresponding to different heights of positions 1312a-d of the carousel 1310. Additionally, the arm 1322 may extend in direction 1321c in connection with loading and unloading slides from the carousel 1310, the buffer 1330 and the XY stage 1340. In an embodiment, it is advantageous to minimize the arc distance that the arm 1322 rotates and/or minimize other distances traversed by the arm 1322 and/or slide handler 1320 in order to minimize dead times of the slide caching device 1300, as further discussed below. Movements of the carousel 1310, slide handler 1320, and XY stage 1340 may be controlled, in various embodiments, by a control system like that which discussed elsewhere herein. It is also noted that, in an embodiment, the buffer 1330 and the XY stage 1340 may be at the same height.

FIGS. 28A-28J are schematic illustrations showing slide caching operations of the slide caching device of FIGS. 26 and 27 according to an embodiment of the system described herein. According to an embodiment, the slide operations discussed herein minimize dead times of the system, that is, the times during slide pickup and transfer operations that do not overlap with slide scanning and imaging operations. Dead times may include, for example, a park time where the XY stage 1340 moves to a position to allow the slide handler 1320 to pick up the slide. Other contributions to dead time include moving the slide to the return position of the buffer 1330 and reloading the XY stage 1340 with a slide.

Figure 28A:
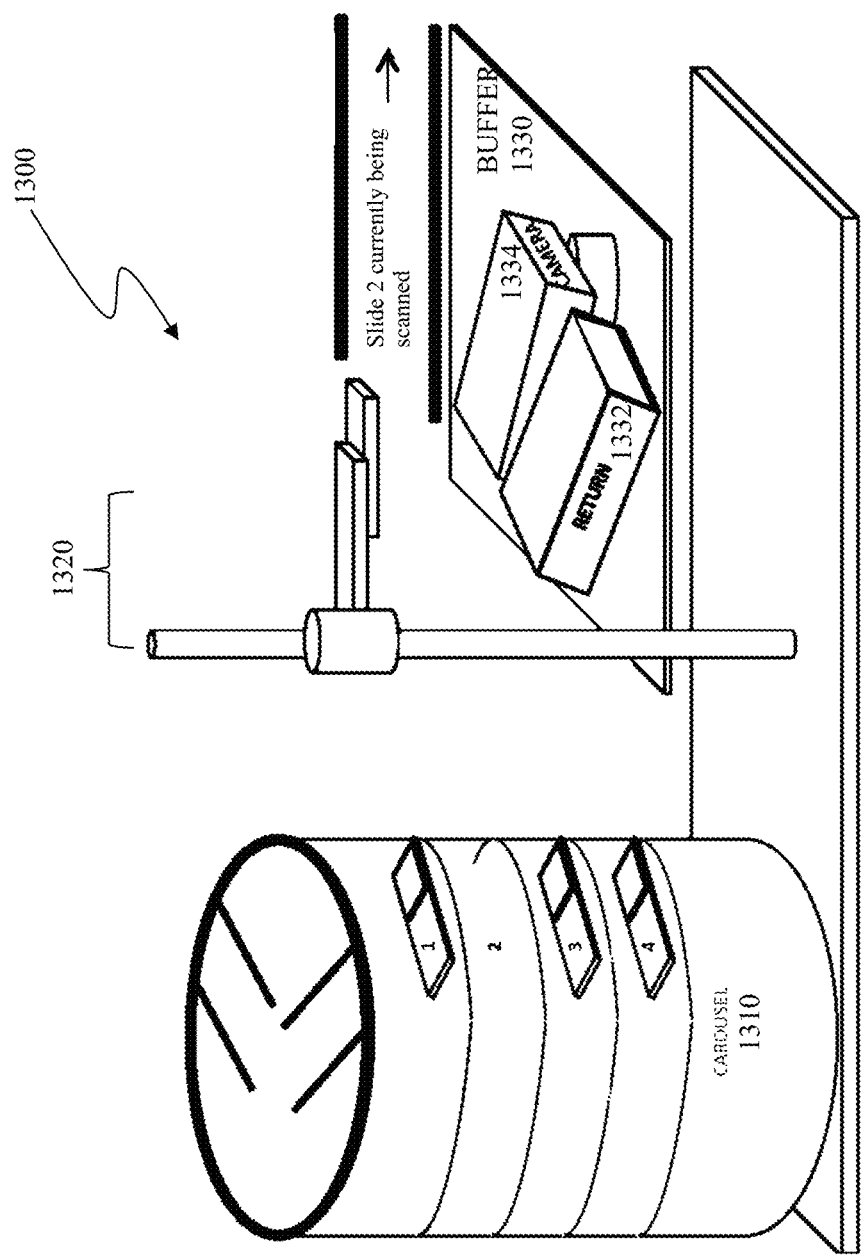
FIGS. 28A-28J are schematic illustrations showing slide caching operations of the slide caching device of FIGS. 26 and 27 according to an embodiment of the system described herein.
Figure 28B:
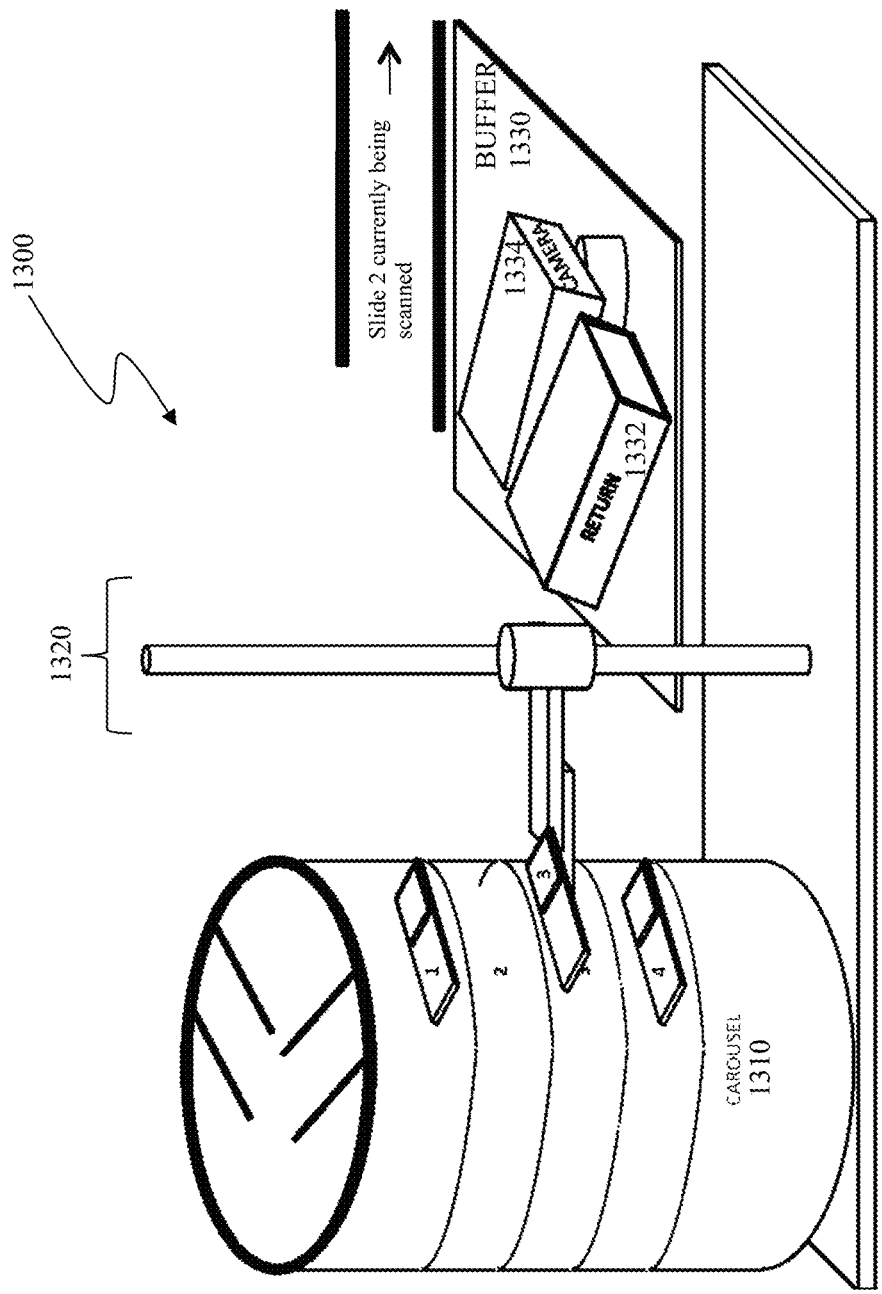
Figure 28C:
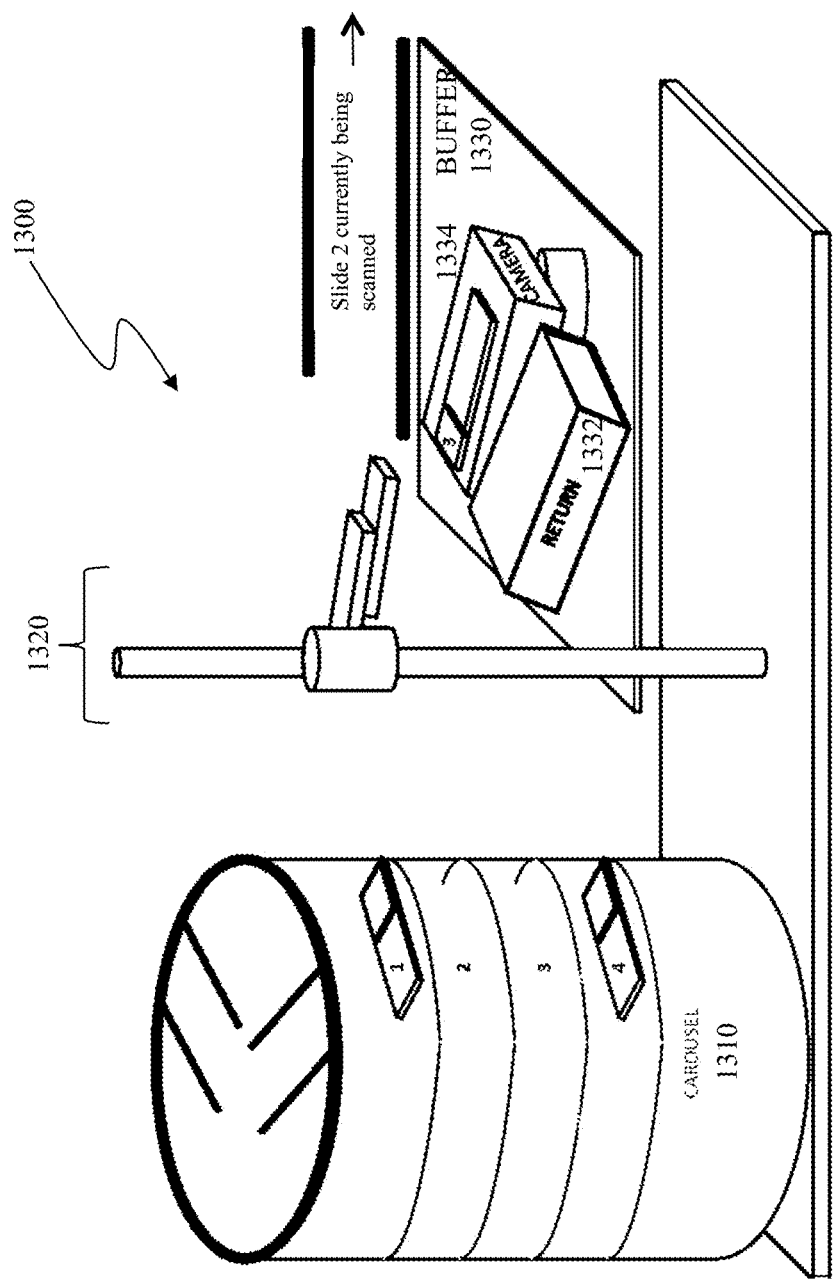
Figure 28D:
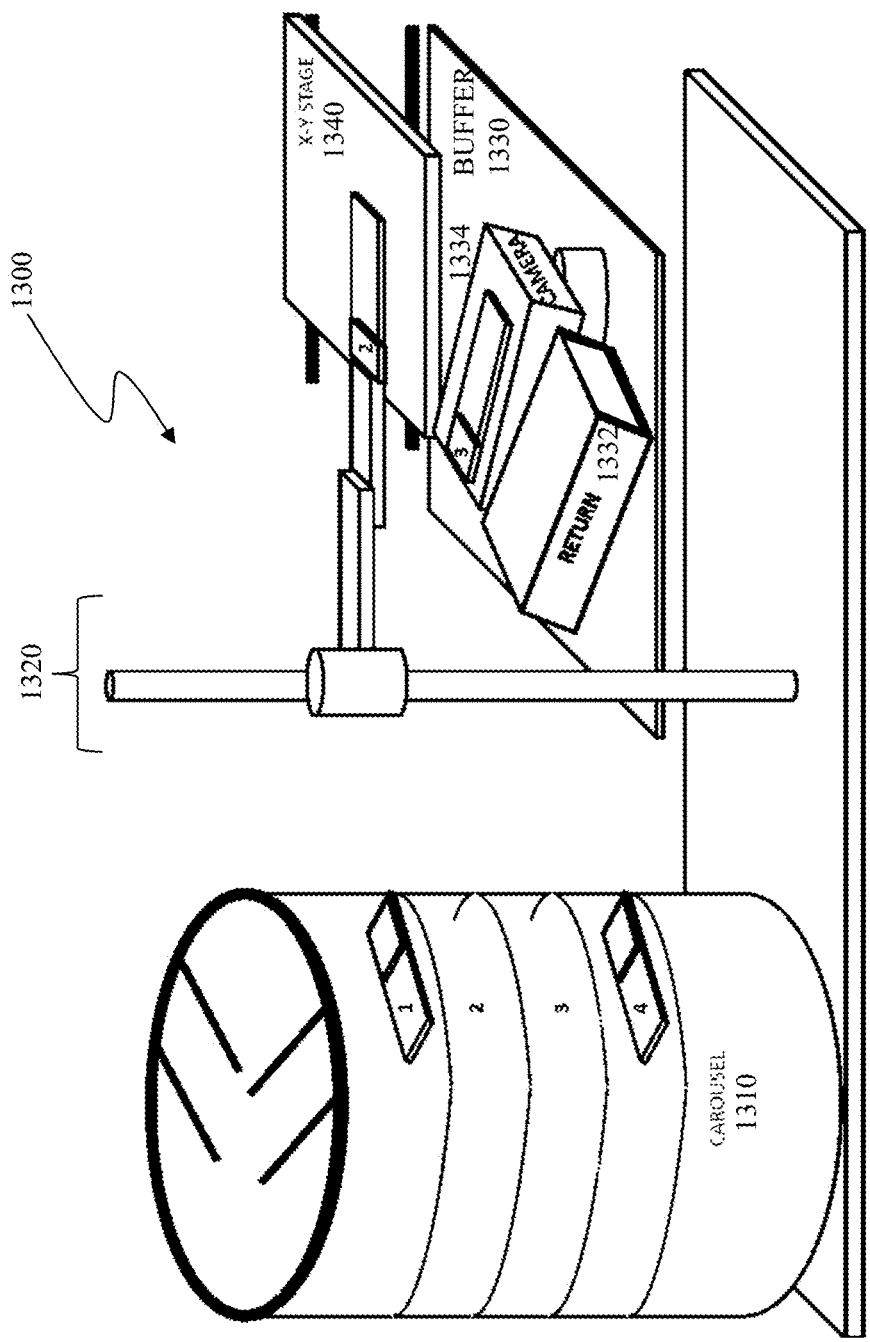

FIG. 28A begins the illustrated sequence in which a slide 2 is currently being scanned and imaged at the imaging device 1350. Slides 1, 3 and 4 are waiting to be scanned and imaged in the carousel 1310, and the slide handler 1320 is in the position for having delivered the slide 2 to the XY stage 1340. FIG. 28B shows that the slide handler 1320 rotates and descends to load the next slide (slide 3) to be scanned and imaged, while slide 2 continues to be scanned and imaged. FIG. 28C shows that the slide handler 1320 transports slide 3 to the camera buffer position 1334 of the buffer 1330 in order for a thumbnail image to be obtained of the slide 3. FIG. 28D shows that the slide handler 1320 is positioned to unload the slide 2 from the XY stage 1340 that is returning from the image device 1350 after scanning of slide 2 has completed. It is noted that the time as the XY stage 1340 moves into position to be unloaded is an example of slack time. The time after the XY stage 1340 is in position to be unloaded with the slide 2 waiting thereon to be unloaded, and slide 3 waiting to be loaded onto the XY stage 1340 is an example of park time.

Figure 28E:
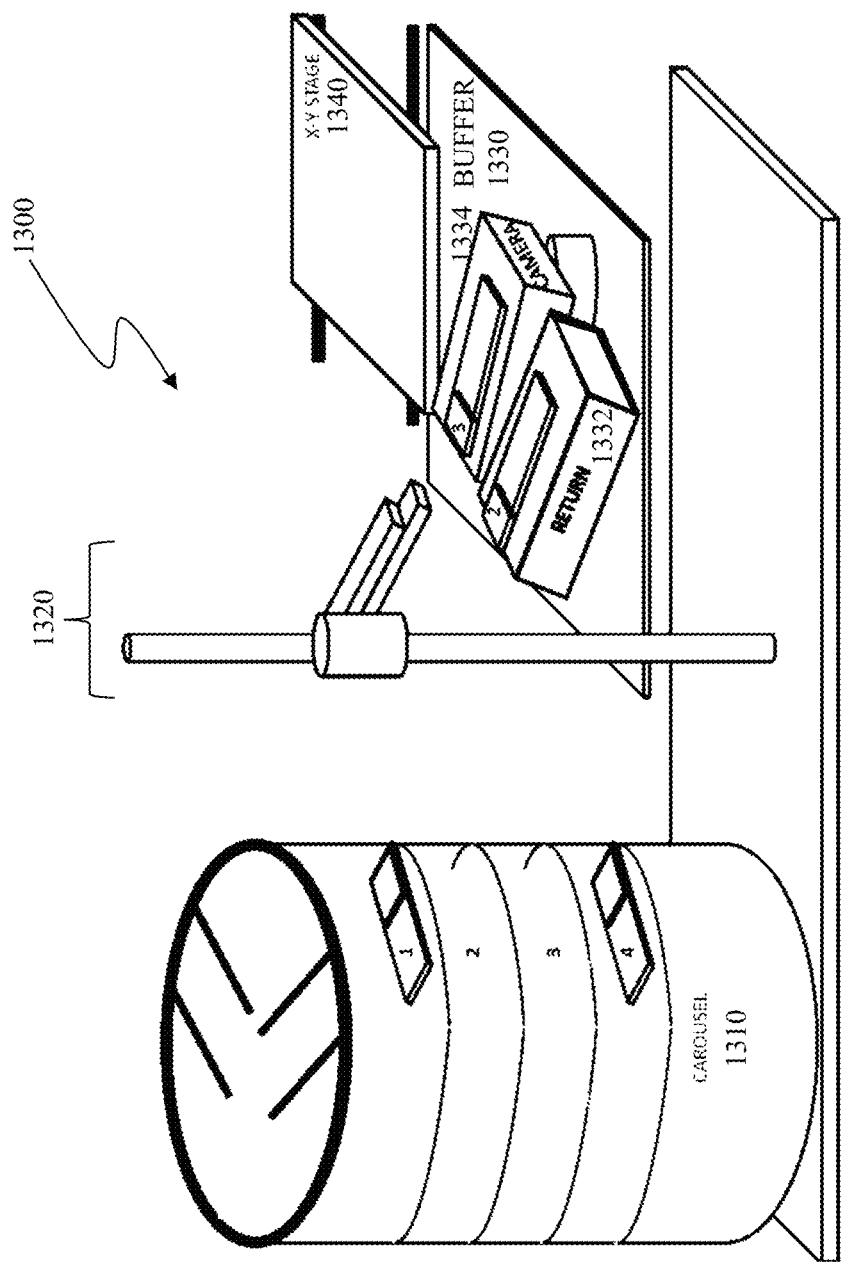
Figure 28F:
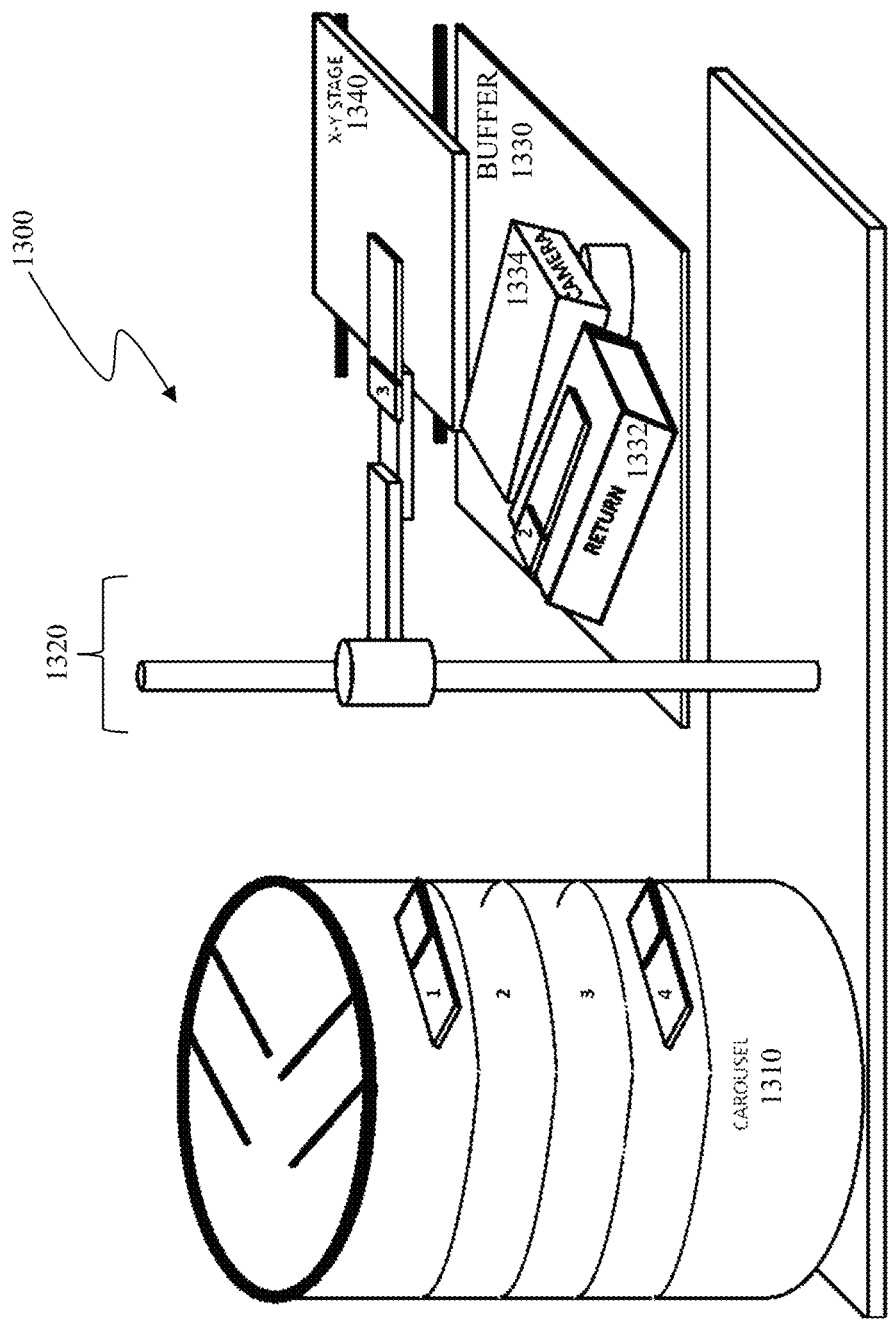
Figure 28G:
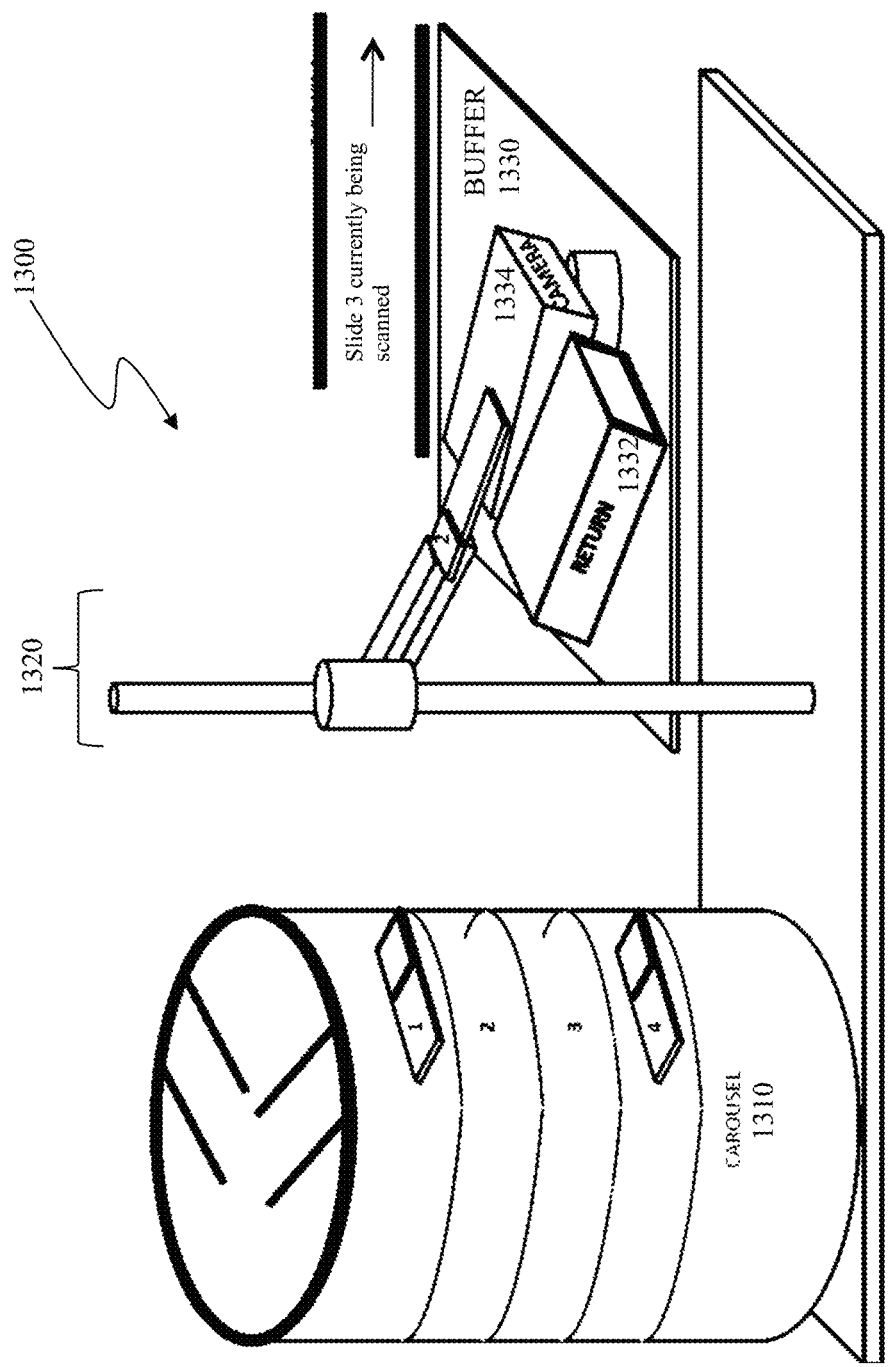
Figure 28H:
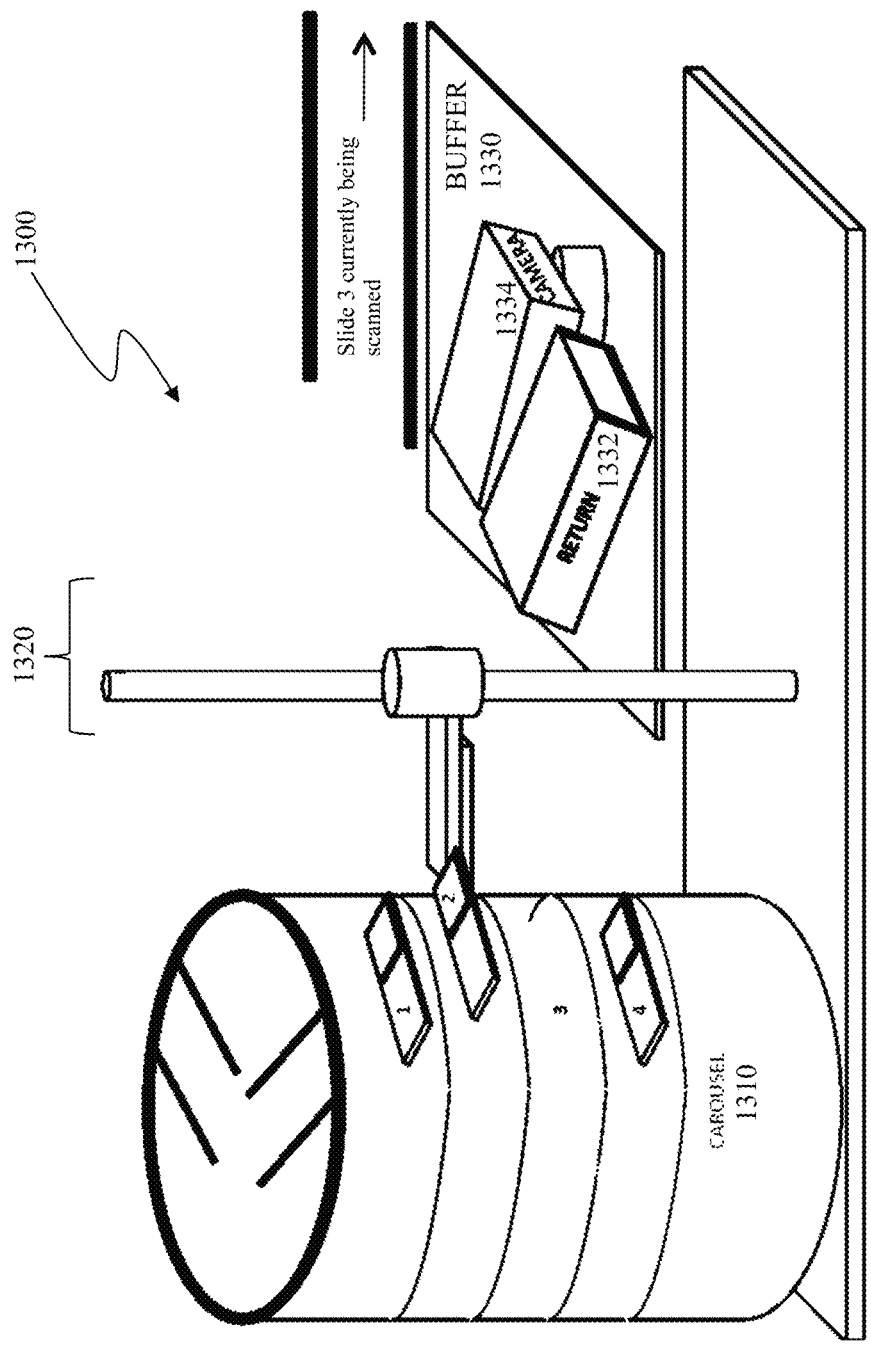
Figure 28I:
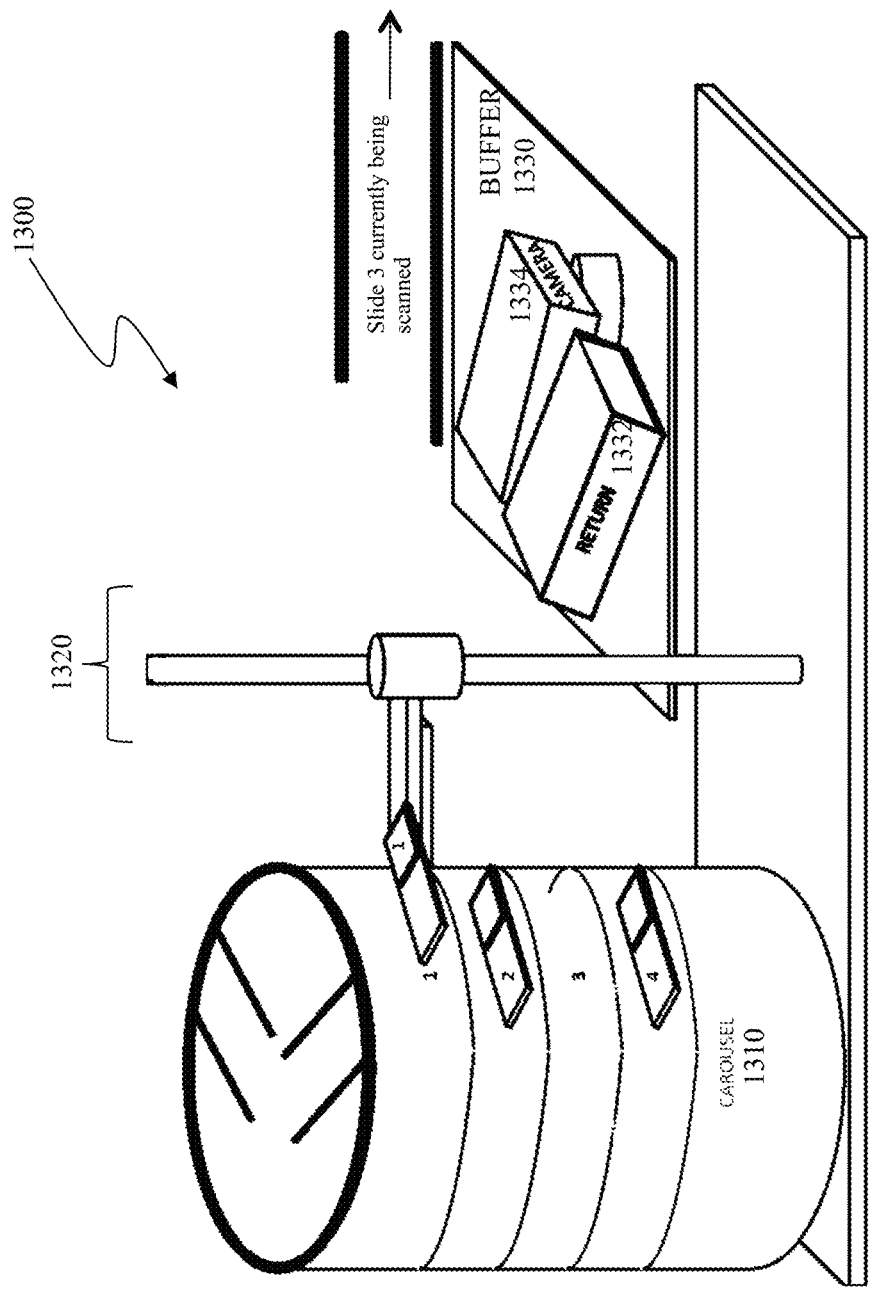
Figure 28J:
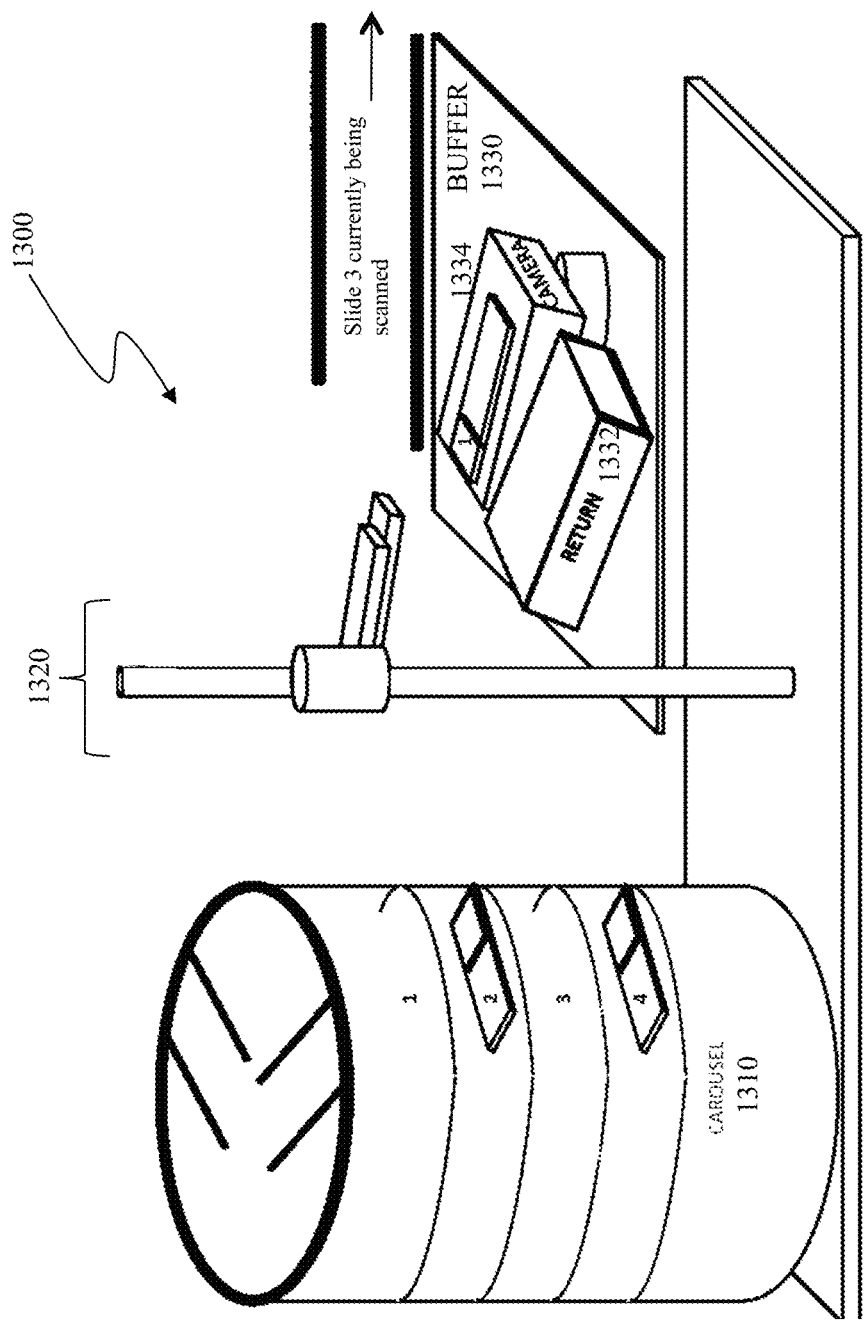

FIG. 28E shows that the slide 2 is transported by the slide handler 1320 from the XY stage 1340 to the return position 1332 of the buffer 1330. The slide handler 1320 then proceeds to the position to pick up the slide 3 from the camera buffer position 1334. FIG. 28F shows that the slide 3 is picked up from the camera buffer position 1334 and unloaded onto the XY stage 1340. FIG. 28G shows that the slide 3 is currently being scanned while slide 2 is being pickup from the return buffer position 1332 by the slide handler 1310. FIG. 28H shows that the slide 2 is returned to its position in the carousel 1310 by the slide handler 1310 that rotates and moves translationally to the proper position. FIG. 28I shows that the slide handler 1310 moves translationally to the proper position to pick up slide 1 from the carousel 1310. FIG. 28J shows that the slide handler 1310 transports and unloads the slide 1 at the camera buffer position where the thumbnail image of slide 1 is obtained, while slide 3 is still currently being scanned. Further iterations, similar to that discussed above in connection with the illustrated sequencing, may be performed with respect to any remaining slides (e.g., slide 4) on the carousel 1310 and/or for any user slides inserted by the user into the user tray 1314 to initiate the by-pass mode operation discussed herein.

According further to the system described herein, an illumination system may used in connection with microscopy embodiments that are applicable to various techniques and features of the system described herein. It is known that microscopes may commonly use Köhler illumination for brightfield microscopy. Primary features of Köhler illumination are that the numerical aperture and area of illumination are both controllable via adjustable irises such that illumination may be tailored to machine a wide range of microscope objectives with varying magnification, field of view and numerical aperture. Köhler illumination offers desirable results but may require multiple components which occupy a significant volume of space. Accordingly, various embodiments of the system described herein further provide features and techniques for advantageous illumination in microscopy applications that avoid certain disadvantages of known Köhler illumination systems while maintaining the advantages of Köhler illumination.

Figure 29:
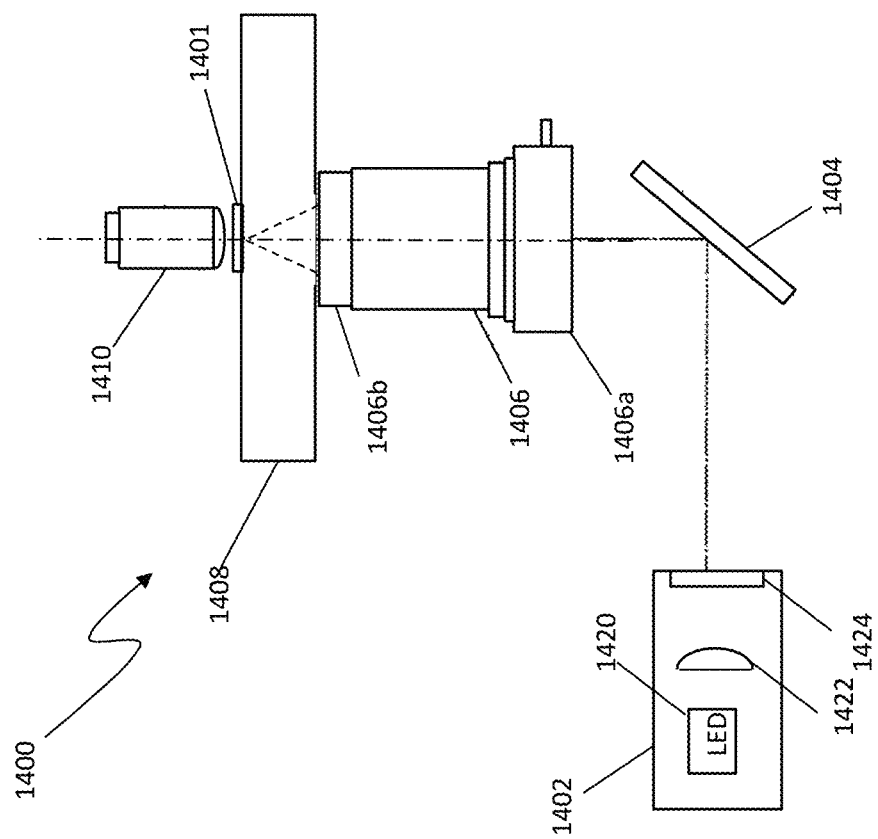
FIG. 29 is a schematic illustration showing an illumination system for illuminating a slide using a light-emitting diode (LED) illumination assembly according to an embodiment of the system described herein.

FIG. 29 is a schematic illustration showing an illumination system 1400 for illuminating a slide 1401 using a light-emitting diode (LED) illumination assembly 1402 according to an embodiment of the system described herein. The LED illumination assembly 1402 may have various features according to multiple embodiments as further discussed herein. Light from the LED illumination assembly 1402 is transmitted via a mirror 1404 and/or other appropriate optical components to a condenser 1406. The condenser 1406 may be a condenser having a suitable working distance (e.g., at least 28 mm) to accommodate any required working distance of an XY stage 1408, as further discussed elsewhere herein. In an embodiment, the condenser may be condenser SG03.0701 manufactured by Motic having a 28 mm working distance. The condenser 1406 may include an adjustable iris diaphragm that controls the numerical aperture (cone angle) of light that illuminates the specimen on the slide 1402. The slide 1401 may be disposed on the XY stage 1408 under a microscope objective 1410. The LED illumination assembly 1402 may be used in connection with scanning and imaging the specimen on the slide 1401, including, for example, operations in relation to movement of an XY stage, slide caching and/or dynamic focusing, according to the features and techniques of the system described herein.

The LED illumination assembly 1402 may include an LED 1420, such as a bright white LED, a lens 1422 that may be used as a collector element, and an adjustable iris field diaphragm 1424 that may control the area of illumination on the slide 1401. The emitting surface of the LED 1420 may be imaged by the lens 1422 onto an entrance pupil 1406a of the condenser 1406. The entrance pupil 1406a may be co-located with an NA adjusting diaphragm 1406b of the condenser 1406. The lens 1422 may be chosen to collect a large fraction of the output light of the LED 1420 and also to focus an image of the LED 1420 onto the NA adjusting diaphragm 1406b of the condenser 1406 with appropriate magnification so that the image of the LED 1402 fills the aperture of the NA adjusting diaphragm 1406b of the condenser 1406.

The condenser 1406 may be used to focus the light of the LED 1420 onto the slide 1401 with the NA adjusting diaphragm 1406b. The area of illumination on the slide 1401 may be controlled by the field diaphragm 1424 mounted in the LED illumination assembly 1402. The field diaphragm, and/or spacing between the condenser 1406 and the field diaphragm 1424, may be adjusted to image the light from the LED 1420 onto the plane of the slide 1401 so that the field diaphragm 1424 may control the area of the slide 1401 that is illuminated.

Since an image sensor acquires frames while a Y stage containing a slide is moving, the LED 1420 may be pulsed on and off (e.g., strobed) to allow very high brightness over a short time. For example, for a Y stage moving at about 13 mm/sec, to maintain no more than 0.5 pixel (0.250 micron/pixel) blur, the LED 1420 may be pulsed to be on for 10 microseconds. The LED light pulse may be triggered by a master clock locked to the dither lens resonant frequency in accordance with the focus system and techniques further discussed elsewhere herein.

Figure 30:
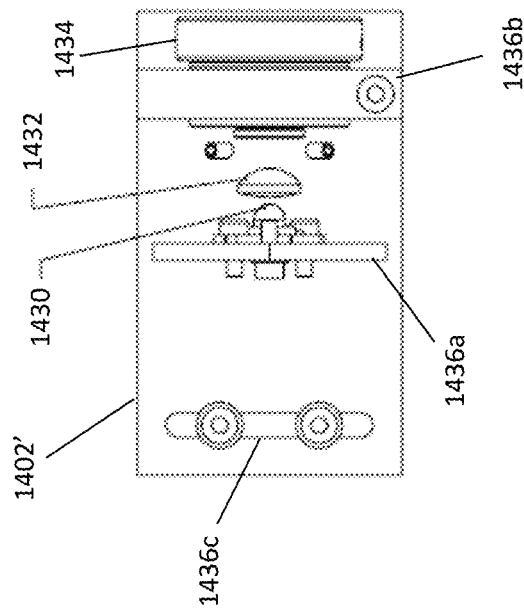
FIG. 30 is a schematic illustration showing a more detailed view of an embodiment for a LED illumination assembly according to the system described herein.

FIG. 30 is a schematic illustration showing a more detailed side view of an embodiment for a LED illumination assembly 1402' according to the system described herein and corresponding to the features described herein with respect to the LED illumination assembly 1402. An implementation and configuration of an LED 1430, a lens 1432, and a field diaphragm 1434 are shown with respect to and in connection with other structural support and adjustment components 1436.

Figure 31:
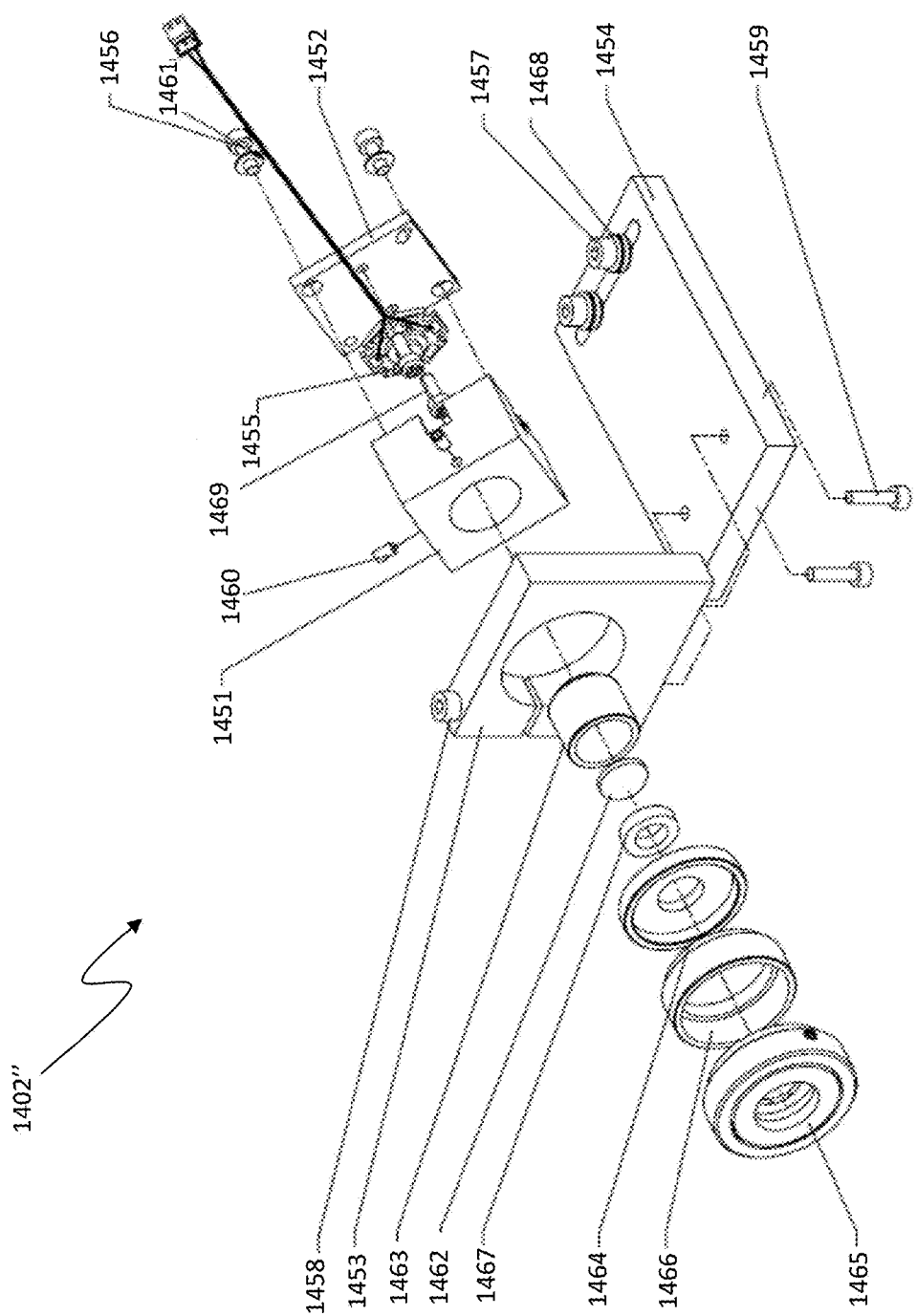
FIG. 31 is a schematic showing an exploded view of a specific implementation of an LED illumination assembly according to an embodiment of the system described herein.

FIG. 31 is a schematic illustration showing an exploded view of a specific implementation of an LED illumination assembly 1402" according to an embodiment of the system described herein having features and functions like that discussed with respect to the LED illumination assembly 1402. An adapter 1451, mount 1452, clamp 1453, and mount 1454 may be used to securely mount and situate an LED 1455 in the LED illumination assembly 1402" so as to be securely positioned with respect to a lens 1462. Appropriate screw and washer components 1456-1461 may be further used to secure and mount the LED illumination assembly 1402". In various embodiments, the LED 1455 may be a Luminus, PhlatLight White LED CM-360 Series this is a bright white LED having an optical output of 4,500 lumens and long life of 70,000 hours and/or a suitable LED made by Luxeon. The lens 1462 may be an MG 9P6 mm, 12 mm OD (outer diameter) lens. A tube lens component 1463, adapter 1464, stack tube lens component and retaining ring 1467 may be used to position and mount the lens 1462 with respect to the adjustable field diaphragm component 1465. The adjustable field diaphragm component 1465 may be a Ring-Activated Iris Diaphragm, part number SM1D12D by Thor Labs. The stack tube lens 1466 may be a P3LG stack tube lens by Thor Labs. The tube lens 1463 may be a P50D or P5LG tube lens by Thor Labs. Other washer 1468 and screw components 1469 may be used, where appropriate, to further secure and mount elements of the LED illumination assembly 1402".

According further to the system described herein, devices and techniques are provided for high speed slide scanning for digital pathology applications according to various embodiments of the system described herein. In an embodiment, a slide holder for a pathology microscope may include: (i) a tray in the form of a disk and (ii) a plurality of recesses formed in the tray in which each recess is adapted to receive a slide and the recesses are disposed circumferentially in the tray. The tray may include a central spindle hole and two lock holes wherein the lock holes adapted to pick up on a drive adapted to rotate at high speed around an axis normal to the tray. The recesses may be recesses milled at distinct angular positions in the tray. The recesses may have semi-circular protrusions to touch the slide but not overly constrain the slide thereby allowing the slide to be substantially strain-free. The recesses may also have a cutout that allows a finger hold to place and extract the slide from the recess by an operator. In various embodiments, the slide holder, and operation thereof, may be used in connection with the features and techniques discussed elsewhere herein for an imaging system.

Figure 32:
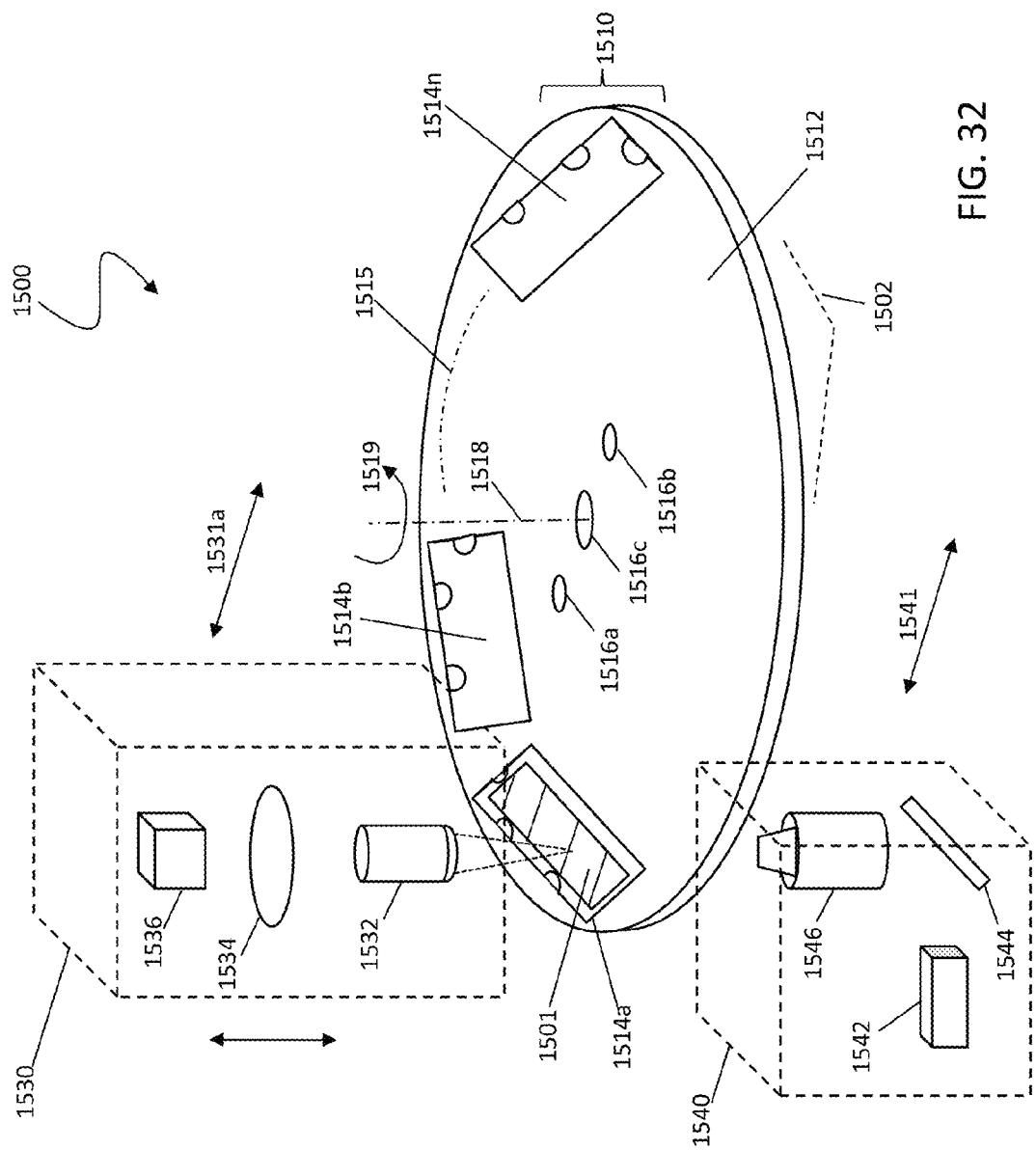
FIG. 32 is a schematic illustration showing a high speed slide scanning device according to an embodiment of the system described herein that may be used in connection with digital pathology imaging.

FIG. 32 is a schematic illustration showing a high speed slide scanning device 1500 according to an embodiment of the system described herein that may be used in connection with digital pathology imaging. A slide holder 1510 may include a tray 1512 with recesses 1514a,b . . . n disposed in angular positions of a circumferential or annular ring 1515 on the tray 1512, and the recesses 1514a-n may each be sized to hold a slide 1501. The tray 1512 is illustrated as a circular disk and may be manufactured to hold a desired number slides. For example, to hold 16 slides, the tray 1512 may measure approximately 13 inches in diameter. It is noted that other configurations of slides and of the size and shape of the tray may be used, as appropriate, in connection with the system described herein, and the orientation and configuration of the recesses 1514a-n and may be appropriately modified. A slide may be placed in each recess 1514a-n of the tray 1512, such as the placing of slide 1501 in the recess 1514a, and the tray 1512 may be placed into the high speed slide scanning device 1500. The tray 1512 may include a central spindle hole 1516c and two lock holes 1516a and 1516b which may engage with a drive which rotates the slide holder 1510 at high speed around axis 1518 in rotational direction 1519. The tray 1512 may be placed into a low profile drawer, shown representationally as 1502, that may retract the tray 1512 into the device 1500.

Figure 33:
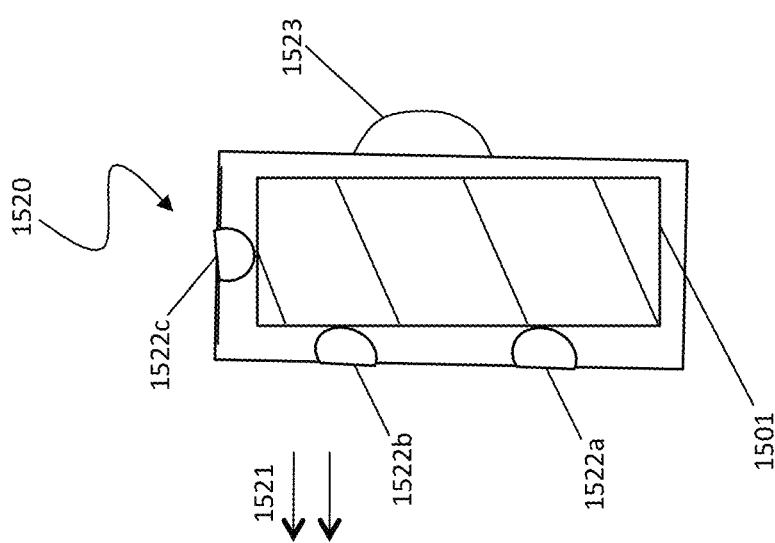
FIG. 33 is a schematic illustration showing a recess on a tray of the high speed slide scanning device in more detail according to an embodiment of the system described herein.

FIG. 33 is a schematic illustration showing a recess 1520 on a tray of the high speed slide scanning device in more detail according to an embodiment of the system described herein. The recess 1520 may be any of the recesses 1514a-n. The recess 1520 may include a plurality of semi-circular protrusions, such as three protrusions 1522a-c, to touch the slide 1501 but not overly constrain the slide 1501, thereby allowing the slide 1501 to be substantially strain-free. A cutout 1523 allows a finger hold to place and extract the slide 1501 from the recess 1520 by an operator. Centripetal accelerations, shown schematically by arrows 1521, produced by the slide holder 1510/tray 1512 as it revolves around the axis 1518 may apply a small holding force to the slide 1501 to keep the slide 1501 in place while imaging occurs. The holding force may be designed to be at least 0.1 g's initially by rotating the tray 1512 at rates greater than 100 rpm to register the slide 1501 against the semi-circular protrusions 1522a-c. Once the slide 1501 is registered, the rotation rate may be reduced consistent with imaging rates of the system like that discussed elsewhere herein. At lower rates, even a slight holding force would stabilize the slide 1501 against the protrusions 1522a-c.

Referring again to FIG. 32, a microscope imaging system 1530, like that discussed in detail elsewhere herein, may be disposed above the rotating tray 1512 to image areas of the circumferential ring 1515 where the slides are placed. The imaging system 1530 may include a high NA microscope objective 1532, for example 0.75 NA with a large working distance, an intermediate lens 1534 and a CCD or CMOS 2D array image sensor 1536 placed at the appropriate distance to magnify objects on the slide 1501 to the image sensor 1536. The image sensor 1536 may have a high frame rate, such as greater than 100 frames/sec. For example, the image sensor 1536 may be part of a Dalsa Falcon 1.4M100 camera operating at 100 frames/sec or the equivalent. The imaging system 1530 may be rigidly mounted to a t-axis motorized drive which may be constructed from components such as DC motors or stepper motors, ball or lead screws and/or linear guides. One axis, the radial axis 1531a may move the imaging system 1530, or at least one component thereof, radially through small moves, for example 1 mm steps with a resolution of 10 micron to image one or more rings on the spinning tray 1512 below. The other axis, the focus axis 1531b, moves in small moves 5-10 micron with resolution of 0.1 micron. The focus axis may be constructed to execute moves at high speed, for example executing a small move in a few milliseconds. Movement of the microscope objective 1534 may be controlled by a control system and may be used in connection with dynamic focusing techniques like that discussed elsewhere herein.

An illumination system 1540 may be placed below the revolving tray 1502 and include a light source 1542, such as a high brightness white LED, one or more optical path components such as a mirror 1544, and a condenser 1546, similar to illumination components discussed elsewhere herein. In an embodiment, the condenser and imaging paths of the microscope may be connected together and move as a rigid body, such a direction 1541 of movement of the illumination system 1540 is in the same direction as the radial direction 1531a of the imaging system 1530. In the focus direction 1531b, the imaging path may be decoupled from the condenser path, such that the one or more components of the imaging system 1530 may include independent movement in the focus direction 1531b to execute high speed focus moves.

Figure 34:
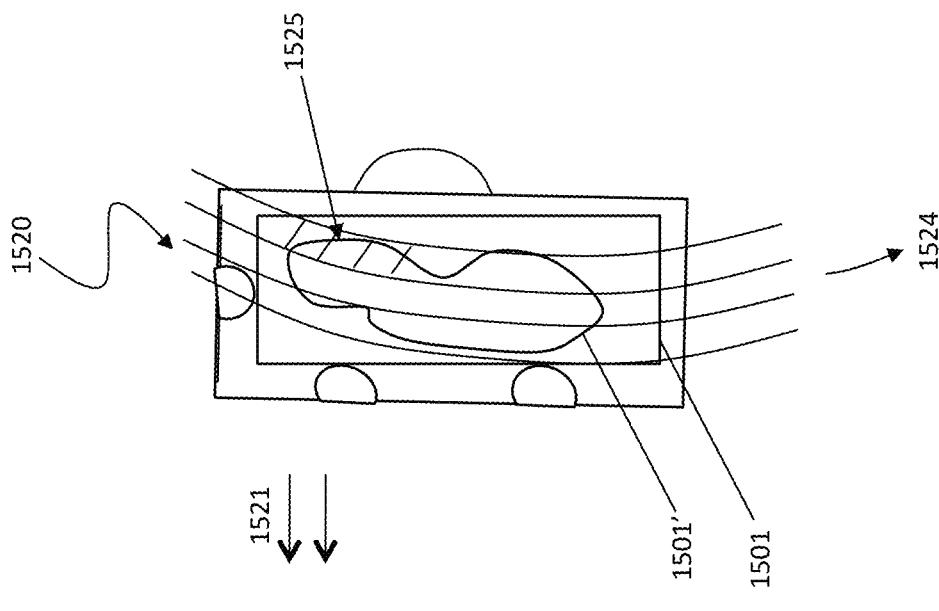
FIG. 34 is a schematic illustration showing an imaging path starting at a first radial position with respect to the slide for imaging an specimen on the slide in the recess.

FIG. 34 is a schematic illustration showing an imaging path starting at a first radial position with respect to the slide 1501 for imaging an specimen 1501' on the slide 1501 in the recess 1520. The recess 1520 with slide 1501 rotates with the slide holder 1510 in the rotational direction 1524. Images may be captured for frames (e.g., frames 1525) according to the image capture techniques discussed elsewhere herein. As shown, image are captured for a row of frames (e.g., frames 1525) for each slide on the slide holder 1510 as the tray 1512 rotates under the imaging system 1530. After one complete revolution of the tray 1512, the radial position of the imaging system 1530 is incremented to capture images for another row of frames for each slide. Each frame is acquired at high rate temporarily freezing the scene below. The bright-field illumination may be sufficiently radiant to allow such short exposures. These exposures may be in a time frame of a few 10's to a few hundred microseconds. The process is continued until the entire area of interest for each slide in the slide holder 1510 is imaged. In connection with this embodiment, processing of the collected images into a mosaic image of an area of interest requires suitable organization mechanisms and/or image tagging to correctly correlate the multiple rows of frames between the multiple slides that are rotated on the tray 1512. Suitable imaging processing techniques may be used to tag images so as to correlate captured images to the proper slide, since the arced motion of the collection of image tiles may be addressed by known stitching software and can be transformed to views that a pathologist would understand while looking under a standard microscope As an example, with a tray in the form of disk of 13.2 inches in diameter revolving at 6 rpm, a 20× microscope objective of NA=0.75 produces a field of view of about 1 mm square. This arced field of view is traversed in about 10 msec. For a tissue section within a 15 mm square active area and assuming 25% overlap between fields, 20 fields would need to be incremented along the radial axis. If frame transfer was short enough not to limit acquisition time, 20 complete revolutions would be sufficient to image 16 slides on the disk. This would occur at 6 rpm in 200 seconds or a throughput of 1 slide every 12.5 seconds.

FIGS. 35A and 35B are schematic illustrations showing an alternative arrangement of slides on a rotating slide holder according to another embodiment of the system described herein. FIG. 35A shows a tray 1512' with recesses 1514' configured such that the longer dimension of the slide 1501 is oriented along the radius of the disk-shaped tray 1512' that rotates in direction 1519'. In this configuration, more slides (e.g., 30 slides) may fit on the tray 1512'. FIG. 35B is a schematic view showing an imaging path for the slide 1501 in a recess 1520' that is configured as noted above. In the illustrated embodiment, the slide 1501 is maintained in the recess 1520' according to centripetal forces shown in the direction 1521' and the protrusions 1522a'-c'. The direction of rotation 1524' over which the image processing is performed is shown for collection of images for frames 1525' for the specimen 1501'. The radial position of the imaging system 1530 is incremented to in length-wise increments of the slides to capture images for successive rows of frames for each slide. In an example, for a 15 mm×15 mm active area and assuming a 25% overlap between fields. Twenty fields would need to be incremented along the radial axis. Again, 20 revolutions at 6 rpm would provide complete imaging in 200 seconds but with more efficient scanning given the orientation of the slides and therefore throughput would increase to one slide every 6.67 seconds.

Figure 36:
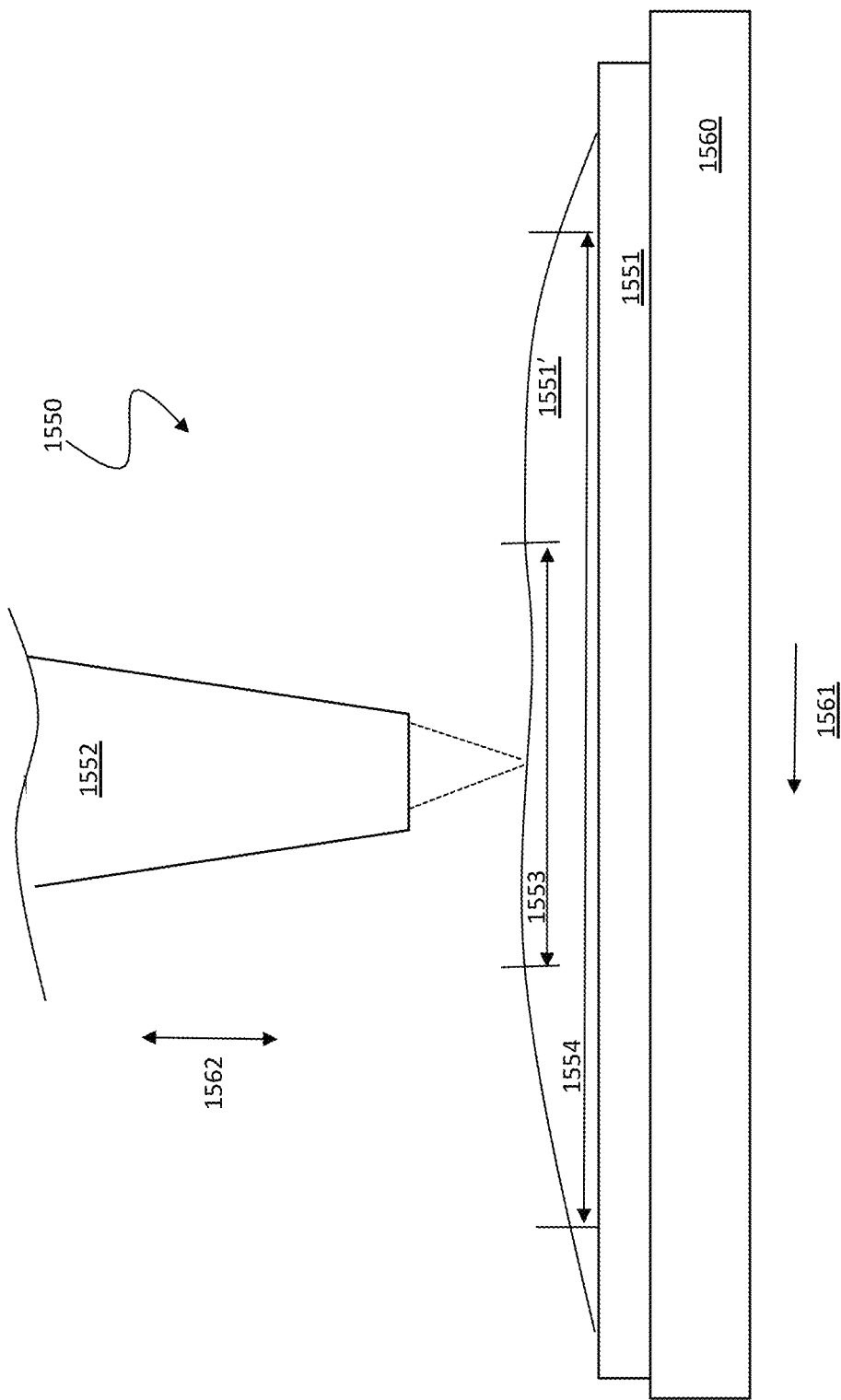
FIG. 36 is a schematic illustration showing an imaging system according to an embodiment of the system described herein that includes an objective disposed to examine a specimen on a slide.

FIG. 36 is a schematic illustration showing an imaging system 1550 according to an embodiment of the system described herein that includes an objective 1552 disposed to examine a specimen 1551' on a slide 1551. In an embodiment, focus positions may be pre-determined through a prior slower rotation of the disk before image acquisition. Budgeting as much as 20 seconds per slide for autofocus would make total scan time under 30 seconds per slide—an order of magnitude faster than current state of the art systems. As a tray 1560, on which the slide 1551 is disposed, rotates in direction 1561, the objective 1552 may make undergo minute movements in the direction 1562 to be positioned at best focus as determined according to the system described herein. Distinct autofocus values would not need to be set for each field of view 1553 but apply to distinct larger zones 1554 on the slide 1551, for example 3×3 fields of view or subframes due to the larger spatial frequencies of slide warp or tissue thickness. The autofocus values would be interpolated applying best focus while slide moves under the camera in its arc path.

Alternatively, a dynamic focusing technique, such as on-the-fly focusing techniques described elsewhere herein, may be advantageously employed in connection with the high speed scanning systems provided herein. It is noted that the times for acquiring focus points (e.g. 120 focus points per second) enable use of the on-the-fly focusing along with the high speed rotational scanning techniques discussed above. It is further noted that it is well within the field of control systems to control a rotating disk to speeds within 1 part in 10,000, allowing open loop sampling of each image without relying on rotational feedback of the disk.

Generally, a low resolution thumbnail image is produced of the slide. This may be accomplished by setting up a low resolution camera over an angular position of the disk so as not to interfere with the high resolution microscope just described For extremely high volume applications the disk format lends itself to robotic handling. Semi-conductor wafer robots handling 300 mm (~12") disks may be used to move disks from a buffer stock to the high speed scanning device. Further, most technologies position the slide under the microscope objective through linear stages in a step and repeat motion. These motions dominate the image acquisition times. The system described herein using a rotary motion is efficient and highly repeatable. The autofocus and image acquisition times are an order of magnitude smaller than the current state of the art products.

Most systems also require clamping mechanisms or spring hold-downs to hold the slide in place during the stop and go motions of the stage. The system described herein does not require a hold-down mechanism in that the rotational motion creates centripetal acceleration which pushes the slide into a pre-determined location in a recess cut into the disk. This makes construction of the slide holder simpler and more reliable. In addition, slide hold downs may warp or strain the slide complicating autofocus processes and are advantageously avoided according to the system described herein.

Current systems have peak speeds of 2-3 minutes for a 15 mm active area per slide. The systems and methods provided herein allow the same active area to scanned under 30 seconds, for the example outlined above. Many pathology labs look to scan from 100 slides to 200 slides per day. With these high rates of image acquisition an operator could work through a daily inventory of slides in an hour including the added steps of loading and unloading disks, barcode reading, pre-focus. This allows faster time to result and enhanced economics for the lab.

Figure 37:
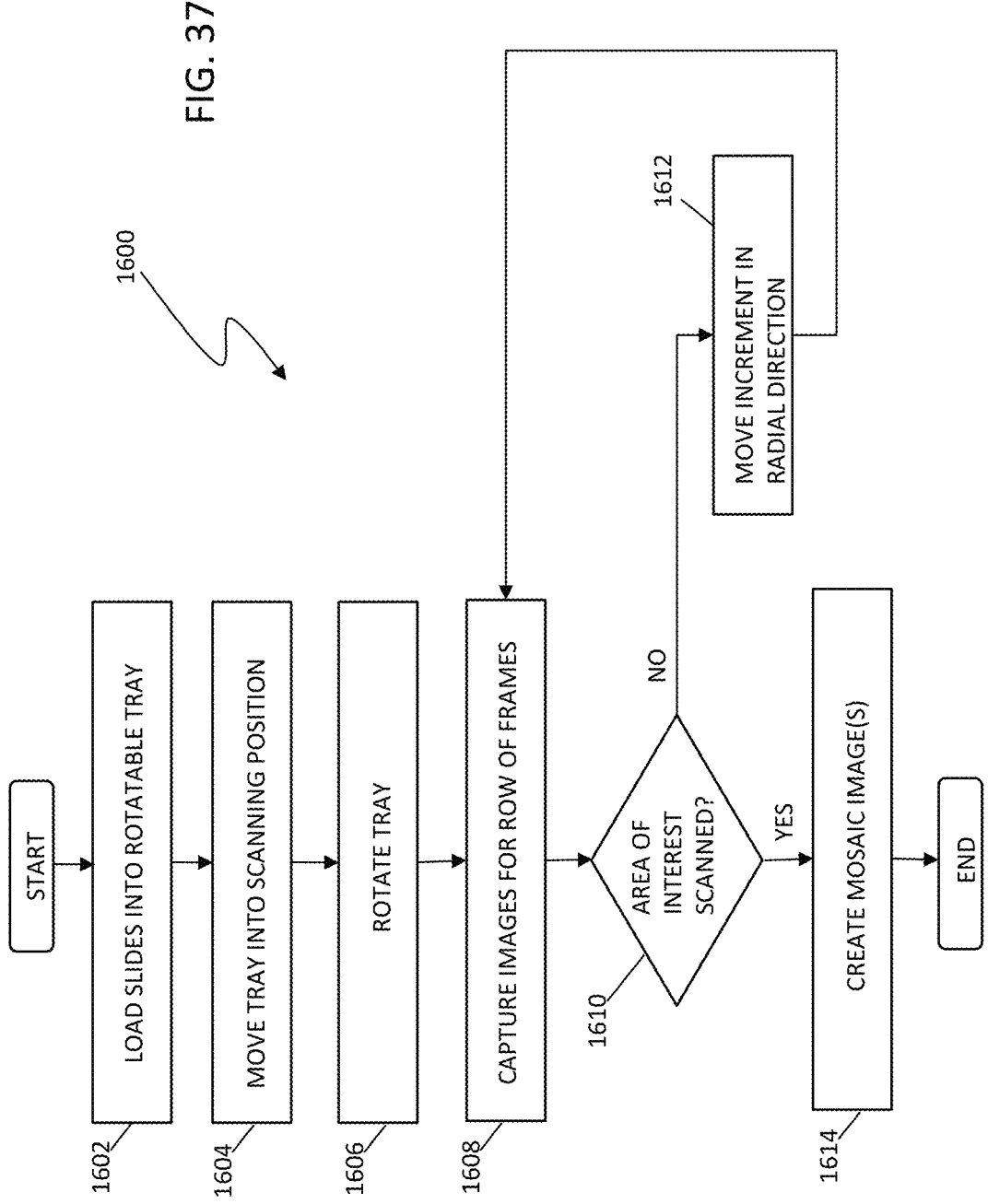
FIG. 37 is a flow diagram showing high speed slide scanning using a rotatable tray according to an embodiment of the system described herein.

FIG. 37 is a flow diagram 1600 showing high speed slide scanning using a rotatable tray according to an embodiment of the system described herein. At a step 1602, slides are located into recesses of the rotatable tray. After the step 1602, processing proceeds to a step 1604 where the rotatable tray is moved into a slide scanning position with respect a scanning and imaging system. After the step 1604, processing proceeds to a step 1606 where rotation of the rotatable tray is initiated. As discussed above, the rotation of the rotatable tray causes centripetal forces acting on the slides to maintain the slides in a desired imaging position. After the step 1606, processing proceeds to a step 1608 where the imaging system captures images, according to systems and techniques described herein and including dynamic focusing techniques, for a row of frames for each slide on a circumferential ring of the rotatable tray. After the step 1608, processing proceeds to a test step 1610 where it is determined whether a desired area of interest on each slide on the rotatable tray has been scanned and imaged. If not, then processing proceeds to a step 1612 where the imaging system and/or certain components thereof, are moved one increment in a radial direction of the rotatable tray. After the step 1612, processing proceeds back to the step 1608. If, at the test step 1610, it is determined that the area of interest on each slide has been scanned and imaged, processing proceeds to a step 1614 where one or more mosaic images are created corresponding to the areas of interest imaged for each slide. After the step 1614, processing is complete.

According further to the system described herein, an optical doubling device and technique may be provided and used in connection with the imaging system features described herein. In an embodiment, the system described herein may sample a resolution element produced by a 20×0.75 NA Plan Apo objective. This resolution element is about 0.5 micron at a wavelength of 500 nm. To obtain further sampling of this resolution element, the tube lens in front of the imaging sensor may be changed. An approximate calculation for computing the focal length of the tube lens given the objective lens (f_tube lens=focal length of tube lens in front of image sensor) is:
pix_sensor=pixel size on CCD or CMOS image sensor
pix_object=pixel size on object or tissue
f_tube lens=pix_object/pix_sensor*9 mm.

To obtain a pixel size at the object of 0.25 micron for the Dalsa Falcon 4M30/60 (7.4 micron sensor pixel), the focal length of the tube lens should be about 266 mm. For a pixel size at the object of 0.125 micron, the focal length of the tube lens should be about 532 mm. It may be desirable to switch between these two object pixel sizes and this may be accomplished by mounting two or more tube lenses to a stage that shuttles in front of the imaging sensor. Given the different path lengths associated with each new focal length, fold mirrors will also need to be added to fold the path for a fixed image sensor position.

Figure 38:
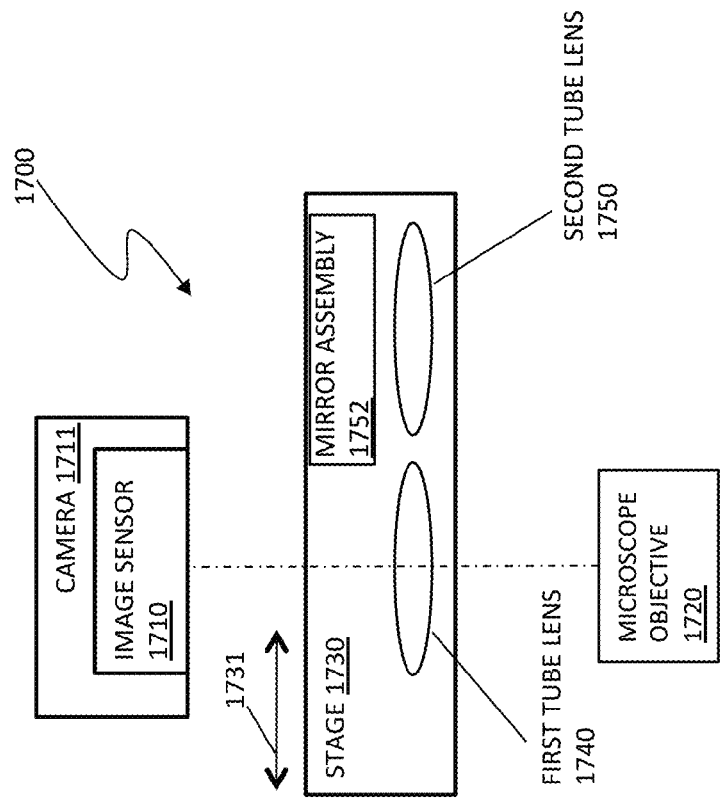
FIG. 38 is a schematic illustration showing an optical doubling image system according to an embodiment of the system described herein.

FIG. 38 is a schematic illustration showing an optical doubling image system 1700 according to an embodiment of the system described herein. The optical doubling image system 1700 may include an image sensor 1710 of a camera 1711 and a microscope objective 1720 as described elsewhere herein. It is noted that other components in connection with the system and techniques discussed herein, such as an on-the-fly focusing system, may also be used with the illustrated optical doubling image system 1700. To achieve two or more object pixel sizes, a plurality of tube lenses, e.g., a first tube lens 1740 and a second tube lens 1750, may be provided in connection with the system described herein. A stage 1730 may shuttle the first tube lens 1740 and the second tube lens 1750, respectively, in front of the imaging sensor. In an embodiment, the stage 1730 may be a linearly actuated stage that moves in a direction 1731, although it is noted that other types of stages and movement thereof may be used in connection with the system described herein. A mirror assembly 1752 is shown with respect to the second tube lens 1750 that may include one or more fold mirrors to adjust the light path from the second tube lens 1750 to the image sensor 1710.

Figure 39A:
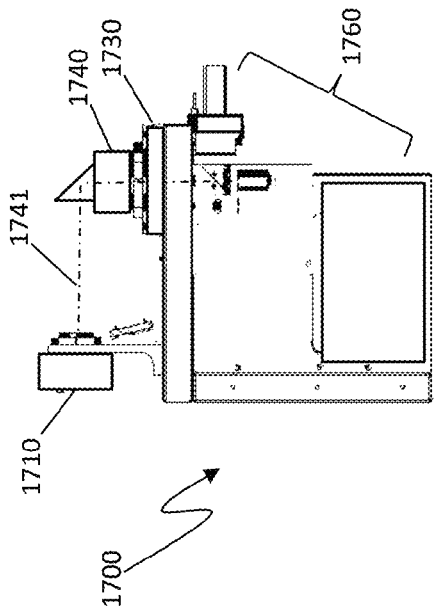
FIGS. 39A and 39B are schematic illustrations of the optical doubling image system showing the shuttling of the first tube lens and the second tube lens in front of the image sensor according to an embodiment of the system described herein.
Figure 39B:
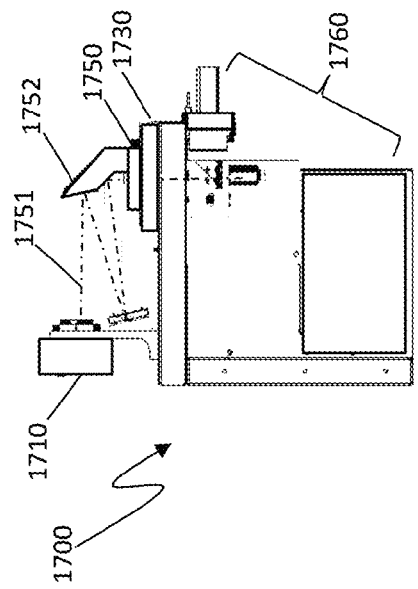

FIGS. 39A and 39B are schematic illustrations of the optical doubling image system 1700 showing the shuttling of the first tube lens 1740 and the second tube lens 1750 in front of the image sensor 1710 according to an embodiment of the system described herein. FIG. 39A shows a light path 1741 for the first tube lens 1740 positioned in front of the image sensor 1710 on the stage 1730. FIG. 39B shows a light path 1751 for the second tube lens 1750 after being shuttled in front of the image sensory 1710 via the stage 1730. As illustrated, the light path 1751 has been increased using one or more mirrors of the mirror assembly 1752. In both figures, it is noted that the optical doubling image system 1700 may include other appropriate structural and optical components 1760 like that discussed in detail elsewhere herein.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a computer readable storage medium and executed by one or more processors. The computer readable storage medium may include a computer hard drive, ROM, RAM, flash memory, portable computer storage media such as a CD-ROM, a DVD-ROM, a flash drive and/or other drive with, for example, a universal serial bus (USB) interface, and/or any other appropriate tangible storage medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A device for slide scanning, comprising:
   a rotatable tray; and
   a plurality of recesses disposed in the rotatable tray, wherein each recess of the plurality of recesses is sized to receive a slide, and wherein said each recess stabilizes the slide in a scanning position as a result of rotation of the rotatable tray, wherein said each recess includes a plurality of protrusions configured to touch multiple sides of the slide when in said each recess, wherein said plurality of protrusions are configured to stabilize the slide and have the multiple sides of the slide register against the plurality of protrusions when the rotatable tray is rotated.

2. The device according to claim 1, wherein the plurality of recesses are disposed on a circumferential ring of the rotatable tray.

3. The device according to claim 1, further comprising:
   an imaging system, wherein at least one component of the imaging system moves in a radial direction of the rotatable tray, and wherein the at least one component of the imaging system moves incrementally in the radial direction corresponding to one complete rotation of the rotatable tray.

4. The device according to claim 1, wherein the at least one recess of the plurality of recesses is sized to receive a slide having a length that is greater than a width of the slide, and wherein the length of the slide is oriented in a radial direction of the rotatable tray or the width of the slide is oriented in a radial direction of the rotatable tray.

5. The device of claim 1, wherein said each recess includes a cut out configured to allow placement and extraction of the slide by an operator.

6. The device of claim 1, wherein the plurality of protrusions are three protrusions.

7. The device of claim 1, wherein the plurality of protrusions extend from two sides of said each recess.

8. A method for scanning a slide, comprising:
   disposing the slide in a first recess of a plurality of recesses of a rotatable tray; and
   rotating the rotatable tray wherein the first recess is sized to receive the slide, and wherein the first recess stabilizes the slide in a scanning position as a result of rotation of the rotatable tray, wherein the first recess includes a plurality of protrusions configured to touch multiple sides of the slide when in the first recess, wherein said plurality of protrusions are configured to stabilize the slide and have the multiple sides of the slide register against the plurality of protrusions when the rotatable tray is rotated.

9. The method according to claim 8, wherein plurality of recesses are disposed on a circumferential ring of the rotatable tray.

10. The method according to claim 8, further comprising:
    providing an imaging system; and
    moving at least one component of the imaging system in a radial direction of the rotatable tray, and wherein the at least one component of the imaging system is moved incrementally in the radial direction corresponding to one complete rotation of the rotatable tray.

11. The method according to claim 8, wherein at least one recess of the plurality of recesses is sized to receive a slide having a length that is greater than a width of the slide, and wherein the length of the slide is oriented in a radial direction of the rotatable tray or the width of the slide is oriented in a radial direction of the rotatable tray.

12. The method of claim 8, wherein the first recess includes a cut out configured to allow placement and extraction of the slide by an operator.

13. The method of claim 8, wherein the plurality of protrusions are three protrusions.

14. The method of claim 8, wherein the plurality of protrusions extend from two sides of the first recess.

15. A device for slide scanning, comprising:
    a rotatable tray; and
    at least one recess disposed in the rotatable tray, wherein the at least one recess is sized to receive a slide, and wherein the at least one recess stabilizes the slide in a scanning position as a result of rotation of the rotatable tray, wherein the at least one recess includes a plurality of protrusions configured to touch sides of the slide when in the at least one recess, wherein said plurality of protrusions are configured to stabilize the slide and have the slide register against the plurality of protrusions when the rotatable tray is rotated, wherein each of the plurality of protrusions is a semicircular protrusion.

16. A method for scanning a slide, comprising:

disposing the slide in at least one recess of a rotatable tray; and rotating the rotatable tray wherein the at least one recess is sized to receive a slide, and wherein the at least one recess stabilizes the slide in a scanning position as a result of rotation of the rotatable tray, wherein the at least one recess includes a plurality of protrusions configured to touch sides of the slide when in the at least one recess, wherein said plurality of protrusions are configured to stabilize the slide and have the slide register against the plurality of protrusions when the rotatable tray is rotated, wherein each of the plurality of protrusions is a semicircular protrusion.

* * * * *